United States Patent
Zeiller et al.

(10) Patent No.: US 8,063,067 B2
(45) Date of Patent: *Nov. 22, 2011

(54) HEXENOIC ACID DERIVATIVES, PROCESSES FOR THE PREPARATION THEREOF, PHARMACEUTICAL COMPOSITIONS COMPRISING THEM, AND THERAPEUTIC APPLICATIONS THEREOF

(75) Inventors: Jean Jacques Zeiller, Lyons (FR); Hervè Dumas, Vaulx Milieu (FR); Valérie Guyard-Dangremont, Saint Maurice de Gourdans (FR); Isabelle Berard, Villard les Bombes (FR); Francis Contard, Lyons (FR); Daniel Guerrier, Saint Genis Laval (FR); Gérard Ferrand, Lyons (FR); Yves Bonhomme, Charbonnières les Bains (FR)

(73) Assignee: Merck Patent GmbH, Darmstadt (DE)

( * ) Notice: Subject to any disclaimer, the term of this patent is extended or adjusted under 35 U.S.C. 154(b) by 130 days.

This patent is subject to a terminal disclaimer.

(21) Appl. No.: 12/507,880

(22) Filed: Jul. 23, 2009

(65) Prior Publication Data

US 2009/0286776 A1 Nov. 19, 2009

Related U.S. Application Data

(63) Continuation of application No. 11/579,361, filed as application No. PCT/EP2005/003606 on Apr. 6, 2005, now Pat. No. 7,632,846.

(30) Foreign Application Priority Data

May 3, 2004 (FR) ..................... 04/04713

(51) Int. Cl.
*A61K 31/192* (2006.01)
*A61K 31/426* (2006.01)
*A61K 31/42* (2006.01)
*A61K 31/41* (2006.01)
*A61K 31/4152* (2006.01)
*C07D 231/08* (2006.01)
*C07D 277/20* (2006.01)
*C07D 263/58* (2006.01)
*C07D 285/06* (2006.01)
*C07D 333/28* (2006.01)
*C07D 333/52* (2006.01)
*C07C 59/115* (2006.01)

(52) U.S. Cl. ........ 514/311; 514/438; 514/433; 514/571; 514/365; 514/367; 514/378; 514/407; 514/361; 514/375; 548/221; 548/127; 548/146; 548/152; 548/240; 548/366.1; 546/152; 549/79; 549/80; 549/81; 549/49; 549/58; 562/465

(58) Field of Classification Search .................. None
See application file for complete search history.

(56) References Cited

U.S. PATENT DOCUMENTS

| 4,335,249 | A | 6/1982 | Johnson et al. |
| 4,562,287 | A | 12/1985 | Del Vecchui et al. |
| 7,465,752 | B2 | 12/2008 | Zeiller et al. |

*Primary Examiner* — Yong Chu
(74) *Attorney, Agent, or Firm* — Millen, White, Zelano & Branigan, P.C.

(57) ABSTRACT

Compounds of the formula (I): in which R, $R^1$, $R^2$ and $R^3$ are as defined in the description, the use thereof for the treatment of dyslipidaemia, atherosclerosis and diabetes, pharmaceutical compositions comprising them, and processes for the preparation of these compounds.

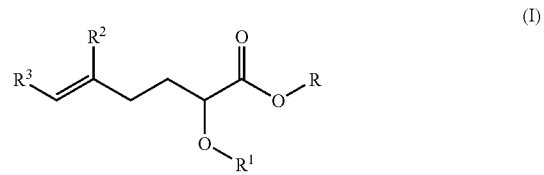

(I)

18 Claims, No Drawings

HEXENOIC ACID DERIVATIVES, PROCESSES FOR THE PREPARATION THEREOF, PHARMACEUTICAL COMPOSITIONS COMPRISING THEM, AND THERAPEUTIC APPLICATIONS THEREOF

This application is a continuation application of U.S. Ser. No. 11/579,361, filed on Nov. 2, 2006 now U.S. Pat. Np. 7,632,846, which is a 371 of PCT/EP05/03606, filed Apr. 6, 2005, which claims priority to FR 04/04713, filed May 3, 2004.

The present invention relates to unsaturated carboxylic acid derivatives that can be used in the treatment of dyslipidaemia, atherosclerosis and diabetes, to pharmaceutical compositions comprising them, and to processes for the preparation of these compounds.

The invention also relates to the use of these compounds for the preparation of medicaments for the treatment of dyslipidaemia, atherosclerosis and diabetes.

In most countries, cardiovascular disease remains one of the major diseases and the main cause of death. About one third of men develop a major cardiovascular disease before the age of 60, with women showing a lower risk (ratio of 1 to 10). With advancing years (after the age of 65, women become just as vulnerable to cardiovascular diseases as men), this disease increases even more in scale. Vascular diseases, such as coronary disease, strokes, restenosis is and peripheral vascular disease remain the prime cause of death and handicap worldwide.

Whereas the diet and lifestyle can accelerate the development of cardiovascular diseases, a genetic predisposition leading to dyslipidaemia is a significant factor in cardiovascular accidents and death.

The development of atherosclerosis appears to be linked mainly to dyslipidaemia, which means abnormal levels of lipoproteins in the blood plasma. This dysfunction is particularly evident in coronary disease, diabetes and obesity.

The concept intended to explain the development of atherosclerosis was mainly focused on the metabolism of cholesterol and on the metabolism of triglycerides.

However, since the studies of Randle et al. (Lancet, (1963), 785-789), a novel concept has been proposed: a glucose-fatty acid cycle or Randle cycle, which describes the regulation of the equilibrium between the metabolism of lipids in terms of triglycerides and cholesterol, and the oxygenation of glucose. Following this concept, the inventors have developed a novel programme, the aim of which is to find novel compounds acting simultaneously on lipid metabolism and glucose metabolism.

Fibrates are well-known therapeutic agents with a mechanism of action via the "Peroxisome Proliferator Activated Receptors". These receptors are the main regulators of lipid metabolism in the liver (PPARα isoform). In the last 10 years, thiazolidinediones have been described as powerful hypoglycaemiant agents in man and animals. It has been reported that thiazolidinediones are powerful selective activators of another isoform of PPARs: PPARγ (Lehmann et al., J. Biol. Chem. (1995), 270, 12953-12956).

The inventors have discovered a novel class of compounds that are powerful activators of the PPARα and PPARγ isoforms. As a result of this activity, these compounds have a substantial hypolipidaemiant and hypoglycaemiant effect.

More specifically, the invention relates to compounds derived from hexenoic acid, of the formula (I) below:

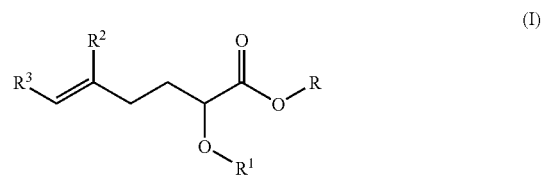

in which:
$R^1$ is chosen from:
a $(C_6-C_{18})$aryl radical optionally substituted by and/or optionally fused to a saturated or unsaturated monocyclic or polycyclic 5- to 8-membered nucleus optionally containing one or more hetero atoms chosen from O, N and S, the said nucleus itself being optionally substituted, and
a saturated, unsaturated or aromatic monocyclic 5- to 8-membered heterocyclic radical, optionally substituted and containing one or more hetero atoms chosen from O, N and S;
$R^2$ and $R^3$ each represent a hydrogen atom or together form a $C_3-C_7$ alkylene chain; and
R is chosen from a hydrogen atom and a $C_1-C_{10}$ alkyl radical;
the optical isomers thereof, and also the pharmaceutically acceptable addition salts thereof with acids or bases.

The acids that can be used to form the salts of the compounds of the formula (I) are mineral or organic acids. The resulting salts are, for example, the hydrochlorides, hydrobromides, sulfates, hydrogen sulfates, dihydrogen phosphates, citrates, maleates, fumarates, 2-naphthalenesulfonates and pare-toluenesulfonates.

The bases that can be used to form the salts of the compounds of the formula (I) are mineral or organic bases. The resulting salts are, for example, the salts formed with metals and especially alkali metals, alkaline-earth metals and transition metals (such as sodium, potassium, calcium, magnesium or aluminium), or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

The invention especially covers the pharmaceutically acceptable salts, but also the salts that allow a suitable separation or crystallization of the compounds of the formula (I), such as the salts obtained with chiral amines.

The invention also covers the stereoisomers of the compounds of the formula (I), and also mixtures of stereoisomers in all proportions.

The compounds of the formula (I) above also include the prodrugs of these compounds.

The term "prodrugs" means compounds which, once administered to the patient, are chemically and/or biologically converted by the live organism into compounds of the formula (I).

According to the invention, the term "aryl radical" means a monocyclic or polycyclic carbocyclic aromatic group preferably containing from 6 to 18 carbon atoms. Aryl radicals that may be mentioned include phenyl, naphthyl, anthryl and phenanthryl groups.

The term "alkyl" means a linear or branched hydrocarbon-based chain containing from 1 to 10 carbon atoms and better still from 1 to 6 carbon atoms, for example from 1 to 4 carbon atoms.

Examples of alkyl radicals are methyl, ethyl, propyl, isopropyl, butyl, isobutyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl and 7,7-dimethyloctyl.

The heterocyclic radicals are monocyclic or polycyclic radicals comprising hetero atoms generally chosen from O, S and N, optionally in oxidized form (in the case of S and N).

Preferably, at least one of the monocycles constituting the heterocycle comprises from 1 to 4 endocyclic hetero atoms and better still from 1 to 3 hetero atoms.

According to the invention, the polycyclic heterocyclic nucleus consists of one or more monocycles, each of which is 5- to 8-membered.

Examples of 5- to 8-membered monocyclic aromatic heterocyclic groups are heteroaryls, such as pyridine, furan, thiophene, pyrrole, imidazole, thiazole, isoxazole, isothiazole, furazane, pyridazine, pyrimidine, pyrazine, thiazines, oxazole, pyrazole, oxadiazole, triazole and thiadiazole.

Preferred heteroaryl radicals that may be mentioned include pyridyl, pyrimidinyl, triazolyl, thiadiazolyl, oxazolyl, thiazolyl and thienyl radicals.

The saturated or unsaturated heterocyclic radicals are heterocyclic groups bearing no unsaturation, or comprising one or more unsaturations derived from the aromatic heterocyclic groups defined above, respectively.

When $R^2$ and $R^3$ together represent a $C_3$-$C_7$ alkylene chain, it is preferred for $R^2$, $R^3$ and the carbons to which they are attached to form a cyclopentene or a cyclohexene.

The aryl and heterocyclic radicals are optionally substituted by one or more of the following radicals G:

trifluoromethyl; styryl; a halogen atom; a monocyclic, bicyclic or tricyclic aromatic heterocyclic radical comprising one or more hetero atoms chosen from O, N and S; and optionally substituted by one or more radicals T as defined below; a group Het-CO— in which Het represents an aromatic heterocyclic radical as defined above optionally substituted by one or more radicals T; a $C_1$-$C_6$ alkylenediyl chain; a $C_1$-$C_6$ alkylenedioxy chain; nitro; cyano; ($C_1$-$C_{10}$)alkyl; ($C_1$-$C_{10}$)alkylcarbonyl; ($C_1$-$C_{10}$)alkoxycarbonyl-A- in which A represents ($C_1$-$C_6$)-alkylene, ($C_2$-$C_6$)alkenylene or a bond; ($C_3$-$C_{10}$)cycloalkyl; trifluoromethoxy; di-($C_1$-$C_{10}$)alkylamino; ($C_1$-$C_{10}$)alkoxy($C_1$-$C_{10}$)alkyl; ($C_1$-$C_{10}$)alkoxy, ($C_6$-$C_{11}$)aryl optionally substituted by one or more radicals T; ($C_6$-$C_{18}$)aryl($C_1$-$C_{10}$)alkoxy-(CO)$_n$— in which n is 0 or 1 and aryl is optionally substituted by one or more radicals T; ($C_6$-$C_{18}$)aryloxy(CO)$_n$— in which n is 0 or 1 and in which aryl is optionally substituted by one or more radicals T; ($C_6$-$C_{18}$)arylthio in which aryl is optionally substituted by one or more radicals T; ($C_6$-$C_{18}$)aryloxy($C_1$-$C_{10}$)alkyl(CO)$_n$— in which n is 0 or 1 and in which aryl is optionally substituted by one or more radicals T; a saturated or unsaturated, monocyclic 5- to 8-membered heterocycle comprising one or more hetero atoms chosen from O, N and S, optionally substituted by one or more radicals T; ($C_6$-$C_{18}$)arylcarbonyl optionally substituted by one or more radicals T; ($C_6$-$C_{18}$)arylcarbonyl-B—(CO)$_n$— in which n is 0 or 1; B represents ($C_1$-$C_6$)alkylene or ($C_2$-$C_6$)alkenylene and aryl is optionally substituted by one or more radicals T; ($C_6$-$C_{18}$)aryl-C—(CO)$_n$— in which n is 0 or 1, C represents ($C_1$-$C_6$)alkylene or ($C_2$-$C_6$)alkenylene and aryl is optionally substituted by one or more radicals T; ($C_6$-$C_{18}$)aryl fused to a saturated or unsaturated heterocycle as defined above, optionally substituted by one or more radicals T; ($C_2$-$C_{10}$)alkynyl; T is chosen from a halogen atom; ($C_6$-$C_{18}$)aryl; ($C_1$-$C_6$)alkyl; ($C_1$-$C_6$)alkoxy; ($C_1$-$C_6$)alkoxy($C_6$-$C_{18}$)aryl; nitro; carboxy; ($C_1$-$C_6$)alkoxycarboxyl; and T may represent oxo in the case where it substitutes a saturated or unsaturated heterocycle; or T represents ($C_1$-$C_6$)alkoxycarbonyl($C_1$-$C_6$)alkyl; or ($C_1$-$C_6$)alkylcarbonyl(($C_1$-$C_6$)alkyl)$_n$—, in which n is 0 or 1.

The term "halogen atom" means a chlorine, bromine, iodine or fluorine atom. The monocyclic, bicyclic or tricyclic aromatic heterocyclic radicals preferably comprise one or more hetero atoms generally chosen from O, S and N, optionally in oxidized form (in the case of S and N). Preferably, at least one of the monocycles constituting the heterocycle comprises from 1 to 4 endocyclic hetero atoms and better still from 1 to 3 hetero atoms.

Preferably, the heterocycle consists of one or more monocycles, each of which is 5- to 8-membered.

Examples of 5- to 8-membered monocyclic heteroaryls are especially pyridine, furan, thiophene, pyrrole, imidazole, thiazole, isoxazole, isothiazole, furazane, pyridazine, pyrimidine, pyrazine, thiazines, oxazole, pyrazole, oxadiazole, triazole and thiadiazole.

Examples of bicyclic heteroaryls in which each monocycles is 5- to 8-membered are chosen from indolizine, indole, isoindole, benzofuran, benzothiophene, indazole, benzimidazole, benzothiazole, benzofurazane, benzothiofurazane, purine, quinoline, isoquinoline, cinnoline, phthalazine, quinazoline, quinoxaline, naphthyridines, pyrazolotriazine (such as pyrazolo-1,3,4-triazine), pyrazolopyrimidine and pteridine.

Preferred heteroaryl radicals that may be mentioned include quinolyl, pyridyl, benzothiazolyl and triazolyl radicals.

The tricyclic heteroaryls in which each monocycle is 5- to 8-membered are chosen, for example, from acridine, phenazine and carbazole.

The term "alkylenediyl chain" means a divalent radical of linear or branched aliphatic hydrocarbon-based type derived from the alkyl groups defined above by stripping out a hydrogen atom. Preferred examples of alkylenediyl chains are chains —(CH$_2$)$_k$—, in which k represents an integer chosen from 2, 3, 4, 5 and 6 and >C(CH$_3$)$_2$ and —CH$_2$—C(CH$_3$)$_2$—CH$_2$— chains. The alkylenedioxy chains denote —O-Alk-O— chains, in which Alk represents linear or branched alkylene, it being understood that alkylene is as defined above for alkylenediyl. Preferred meanings of —O-Alk-O— are, for example, —O—C(CH$_3$)$_2$—O or —O—CH$_2$—CH$_2$O—.

The term "alkenylene" defines an unsaturated alkylene chain containing one or more ethylenic unsaturations, preferably one to three ethylenic unsaturations. Examples of alkylene chains are —CH═CH— or —CH═CH—CH═CH—.

Examples of $C_3$-$C_{10}$ cycloalkyl radicals are especially cyclopropyl, cyclobutyl, cyclopentyl, cyclohexyl, cycloheptyl, cyclooctyl or cyclodecyl radicals.

Saturated or unsaturated, monocyclic 5- to 8-membered heterocycles are saturated, or unsaturated, derivatives of aromatic heterocycles.

Mention may be made more particularly of morpholine, piperidine, thiazolidine, oxazolidine, tetrahydrothienyl, tetrahydrofuryl, pyrrolidine, isoxazolidine, imidazolidine or pyrazolidine.

The term "alkynyl" means an aliphatic hydrocarbon-based group containing one or more unsaturations of acetylenic type. A preferred example is H$_3$C≡C— [sic].

A first preferred group of compounds of the invention consists of compounds for which:

$R^1$ represents a $(C_6-C_{18})$aryl radical, preferably a $(C_6-C_{10})$ aryl, optionally substituted by and/or fused to a monocyclic carbocyclic or heterocyclic 5- to 8-membered nucleus containing from 0 to 4 hetero atoms chosen from O, N and S, which is itself optionally substituted;

$R^2$ and $R^3$ each represent hydrogen or together form a $C_3-C_7$ alkylene chain; and R is chosen from a hydrogen atom and a $C_1-C_{10}$ alkyl radical.

Another even more preferred group of compounds of the invention consists of compounds for which, when $R^1$ represents a substituted $(C_6-C_{10})$-aryl radical, the aryl nucleus is substituted by one or more of the radicals G chosen from:

trifluoromethyl; a halogen atom; styryl; a monocyclic, bicyclic or tricyclic aromatic heterocyclic radical comprising one or more hetero atoms chosen from O, N and S; and optionally substituted by one or more radicals T as defined below; a group Het-CO—, in which Het represents an aromatic heterocyclic group as defined above, optionally substituted by one or more radicals T; a $C_1-C_6$ alkylenediyl chain; a $C_1-C_6$ alkylenedioxy chain; amino; nitro; cyano; $(C_1-C_{10})$-alkyl radical; $(C_2-C_6)$alkynyl radical; $(C_1-C_{10})$alkylcarbonyl radical; $(C_1-C_{10})$alkoxy-carbonyl-A-radical, in which A represents $(C_1-C_6)$alkylene, $(C_2-C_6)$alkenylene radical or a bond; $(C_3-C_{10})$cycloalkyl radical; trifluoromethoxy radical; di$(C_1-C_{10})$-alkylamino radical; $(C_1-C_{10})$alkoxy$(C_1-C_{10})$ alkyl radical; $(C_1-C_{10})$alkoxy radical; $(C_6-C_{18})$aryl radical optionally substituted by one or more radicals T; $(C_6-C_{18})$-aryl$(C_1-C_{10})$alkoxy-$(CO)_n$— radical, in which n is 0 or 1 and in which aryl is optionally substituted by one or more radicals T; $(C_6-C_{18})$aryloxy$(CO)_n$— radical, in which n is 0 or 1 and in which aryl is optionally substituted by one or more radicals T; $(C_6-C_{18})$aryloxy$(CO)_n$—$(C_2-C_6)$alkenyl radical, in which n is 0 or 1; $(C_6-C_{18})$arylthio radical, in which aryl is optionally substituted by one or more radicals T; $(C_6-C_{18})$aryloxy$(C_1-C_{10})$alkyl$(CO)_n$—, in which n is 0 or 1 and in which aryl is optionally substituted by one or more radicals T; a saturated or unsaturated, monocyclic 5- to 8-membered heterocycle comprising one or more hetero atoms chosen from O, N and S, optionally substituted by one or more radicals T; $(C_6-C_{18})$ arylcarbonyl radical optionally substituted by one or more radicals T; $(C_6-C_{18})$arylcarbonyl-B—$(CO)_n$— radical, in which n is 0 or 1; B represents $(C_1-C_6)$-alkylene or $(C_2-C_6)$ alkenylene and aryl is optionally substituted by one or more radicals T; $(C_6-C_{18})$aryl-C—$(CO)_n$— radical, in which n is 0 or 1, C represents $(C_1-C_6)$alkylene or $(C_2-C_6)$alkenylene and aryl is optionally substituted by one or more radicals T; $(C_6-C_{18})$aryl radical fused to a saturated or unsaturated heterocycle as defined above, optionally substituted by one or more radicals T; $(C_2-C_{10})$alkynyl radical; T is chosen from a halogen atom; $(C_6-C_{18})$aryl; $(C_1-C_6)$-alkyl; $(C_1-C_6)$alkoxy; nitro; carboxyl; $(C_1-C_6)$alkoxycarboxyl; and T may represent oxo in the case where it substitutes a saturated or unsaturated heterocycle; or alternatively T represents $(C_1-C_6)$alkoxycarbonyl$((C_1-C_6)$alkyl; or $(C_1-C_6)$alkyl-carbonyl$((C_1-C_6)$ alkyl$)_n$- in which n is 0 or 1.

More preferably, when $R^1$ is $C_6-C_{10}$ aryl, $R^1$ represents phenyl.

Another preferred group of compounds of the invention consists of compounds for which $R^2$ and $R^3$ together represent a $C_3-C_7$ alkylene chain and more preferably $R^2$ and $R^3$ together represent an alkylene chain —$(CH_2)_3$— or —$(CH_2)_4$—.

Another even more preferred group of compounds of the invention consists of compounds for which, with $R^1$ being substituted and/or fused aryl, as defined above, $R^2$ and $R^3$ together represent a $C_3-C_7$ alkylene chain and more preferably $R^2$ and $R^3$ together represent an alkylene chain —$(CH_2)_3$— or —$(CH_2)_4$—; and R is a hydrogen atom.

Another preferred group of compounds of the invention consists of compounds for which $R^2$ and R each represent a hydrogen atom.

More particularly, the preferred compounds of the formula (I) are those chosen from:

2-(4'-methoxybiphenyl-4-yloxy)hex-5-enoic acid;
2-(4-fluorobiphenyl-4-yloxy)hex-5-enoic acid;
2-(4'-phenoxyphenoxy)hex-5-enoic acid;
4-cyclohex-1-enyl-2-[4-(2-methylthiazol-4-yl)phenoxy] butanoic acid;
4-cyclohex-1-enyl-2-[4-(trifluoromethyl)phenoxy]butanoic acid;
4-cyclohex-1-enyl-2-(4'-methoxy-1,1'-biphenyl-4-yloxy) butanoic acid;
2-[4-(5-chlorothiophen-2-yl)phenoxy]-4-cyclohex-1-enylbutanoic acid;
2-(4-chlorophenoxy)-4-cyclohex-1-enylbutanoic acid;
2-(4-benzo[b]thiophen-2-ylphenoxy)-4-cyclohex-1-enylbutanoic acid;
a 2-(4-benzo[b]thiophen-3-ylphenoxy)hex-5-enoic acid;
2-(3'-fluorobiphenyl-4-yloxy)hex-5-enoic acid;
2-(4-trifluoromethylphenoxy)hex-5-enoic acid;
2-[4-(2-methylthiazol-4-yl)phenoxy]hex-5-enoic acid;
2-(2',5'-dimethylbiphenyl-4-yloxy)hex-5-enoic acid;
2-(4'-trifluoromethoxybiphenyl-4-yloxy)hex-5-enoic acid;
2-(4'-chlorobiphenyl-4-yloxy)hex-5-enoic acid; and
2-[3-(quinolin-2-ylmethoxy)phenoxy]hex-5-enoic acid.

The invention also relates to pharmaceutical compositions comprising a pharmaceutically effective amount of at least one compound of the formula (I) as defined above in combination with one or more pharmaceutically acceptable vehicles.

These compositions can be administered orally in the form of tablets, gel capsules or granules with immediate release or controlled release, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrating agent, a lubricant, a colorant or a flavour enhancer, and by forming the mixture into a tablet a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly (vinyl ether), ethylcellulose, methylcellulose, acacia, gum tragacanth, gelatine, shellac, hydroxypropylcellulose, hydroxy-propylmethylcellulose, calcium citrate, dextrin and pectin. Examples of lubricants include magnesium stearate, talc, polyethylene glycol, silica and hardened plant oils. The colorant can be any of those permitted for used in medicaments. Examples of flavour enhancers include cocoa powder, mint in herb form, aromatic powder, mint in oil form, borneol and cinnamon powder. Obviously, the tablet or granule can be suitably coated with sugar, gelatine or the like.

An injectable form comprising the compound of the present invention as active principle is prepared, where appropriate, by mixing the said compound with a pH regulator, a buffer agent, a suspension agent, a solubilizer, a stabilizer, an isotonic agent and/or a preserving agent, and by converting the mixture into a form for intravenous, subcutaneous or intramuscular injection, according to a standard process. Where appropriate, the injectable form obtained can be freeze-dried via a standard process.

Examples of suspension agents include methylcellulose, polysorbate 80, hydroxyethylcellulose, acacia, powdered gum tragacanth, sodium carboxymethylcellulose and polyethoxylated sorbitan monolaurate.

Examples of solubilizers include castor oil solidified with polyoxyethylene, polysorbate 80 nicotinamide, polyethoxylated sorbitan monolaurate and the ethyl ester of castor oil fatty acid.

In addition, the stabilizer encompasses sodium sulfite, sodium metasulfite and ether, while the preserving agent encompasses methyl p-hydroxybenzoate, ethyl p-hydroxybenzoate, sorbic acid, phenol, cresol and chlorocresol.

The present invention also relates to the use of a compound of the formula (I) of the invention for the preparation of a medicament for the prevention of or treating dyslipidaemia, atherosclerosis and diabetes.

The effective administration doses and posologies of the compounds of the invention, intended for the prevention or treatment of a disease, disorder or condition caused by or associated with modulation of PPAR activity, depends on a large number of factors, for example on the nature of the inhibitor, the size of the patient, the aim of the desired treatment, the nature of the pathology to be treated, the specific pharmaceutical composition used and the observations and the conclusions of the treating physician.

For example, in the case of an oral administration, for example a tablet or a gel capsule, a possible suitable dosage of the compounds of the formula (I) is between about 0.1 mg/kg and about 100 mg/kg of body weight per day, preferably between about 0.5 mg/kg and about 50 mg/kg of body weight per day, more preferably between about 1 mg/kg and about 10 mg/kg of body weight per day and more preferably between about 2 mg/kg and about 5 mg/kg of body weight per day of active material.

If representative of body weights of 10 kg and 100 kg are considered in order to illustrate the oral daily dosage range that can be used and as described above, suitable dosages of the compounds of the formula (I) will be between about 1-10 mg and 1000-10000 mg per day, preferably between about 5-50 mg and 500-5000 mg per day, more preferably between about 10.0-100.0 mg and 100.0-1000.0 mg per day and even more preferably between about 20.0-200.0 mg and about 50.0-500.0 mg per day of active material comprising a preferred compound.

These dosage ranges represent total amounts of active material per day for a given patient. The number of administrations per day at which a dose is administered can vary within wide proportions depending on pharmacokinetic and pharmacological factors, such as the half-life of the active material, which reflects its rate of catabolism and clearance, and also the minimum and optimum levels of the said active material, in blood plasma or in other bodily fluids, which are reached in the patient and which are required for therapeutic efficacy.

Many other factors should also be taken into consideration when determining the number of daily administrations and the amount of active material that should be administered in a single dosage intake. Among these other factors, and not the least of which, is the individual response of the patient to be treated.

The present invention also relates to a general process for the preparation of the compounds of the formula (I), by reacting a compound of the formula (II) with an alcohol of the formula $R^1$—$OH_1$ according to the following reaction scheme:

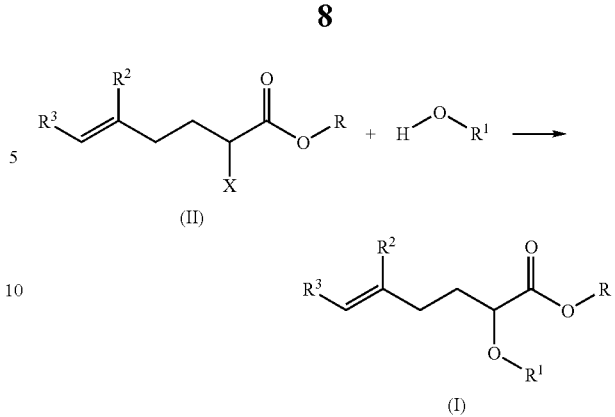

in which reaction scheme $R^1$, $R^2$, $R^3$ and R are as defined above for formula (I) and X represents —OH or a halogen atom, such as chlorine.

When X represents —OH, this reaction is preferably performed in a polar aprotic solvent, such as a linear or cyclic ether, for example diethyl ether, di-tert-butyl ether, diisopropyl ether or dimethoxyethane, or alternatively, such as dioxane or tetrahydrofuran, tetrahydrofuran and dimethoxyethane being preferred.

According to one preferred embodiment of the invention, the molar ratio of the compound of the formula (II) to the alcohol $R^1$—OH ranges between 0.9 and 1.5, an approximately stoichiometric ratio of between 0.9 and 1.3 and preferably between 0.9 and 1.1 being desirable.

In order to facilitate the reaction, it is desirable to add to the medium a coupling agent, such as a lower alkyl (i.e. $C_1$-$C_6$ alkyl) azodicarboxylate, for example ethyl azodicarboxylate.

When it is present in the reaction medium, the coupling agent is incorporated into the medium in a proportion of from 1 to 5 equivalents and better still in a proportion of from 1 to 3 equivalents, for example in a proportion of from 1 to 2 molar equivalents relative to the initial amount of compound of the formula (II).

Preferably, it is also recommended to introduce a phosphine into the reaction medium, such as triphenylphosphine. In this case, the molar ratio of triphenylphosphine to the compound of the formula (II) is preferably maintained between 1 and 5, for example between 1 and 3 and especially between 1 and 2.

When X represents a halogen atom, the solvent is preferably of ketonic type and a base, preferably a mineral base chosen from sodium hydroxide, potassium hydroxide, sodium hydrogen carbonate, potassium hydrogen carbonate, sodium carbonate and potassium carbonate, is introduced into the reaction medium.

Usually, the molar ratio of the base to the compound of the formula (II) ranges between 1 to 5 and better still between 1 to 3.

When X represents a halogen atom, the reaction temperature generally ranges between 10° C. and 120° C., for example between 60° C. and 100° C. and better still between 70° C. and 90° C.

When X represents —OH, the reaction temperature generally ranges between −15° C. and 50° C., it being understood that temperatures of between −15° C. and 10° C. are desirable in the presence of a coupling agent.

The compounds of the formula (I) in which R represents H can advantageously be obtained by saponification of the corresponding compounds of the formula (I) in which R represents a $C_1$-$C_{10}$ alkyl radical. The saponification can be performed via the action of a base, such as a mineral base chosen from lithium hydroxide, potassium hydroxide, sodium hydroxide, sodium hydrogen carbonate, potassium hydrogen carbonate, sodium carbonate and potassium carbonate. The molar amount of base to be used generally ranges from 1 to 20 equivalents and preferably from 1 to 12 equivalents depending on the strength of the selected base.

More particularly, in the case of lithium hydroxide (LiOH), it is preferred to react together from 8 to 12 equivalents of base relative to the amount of ester of the formula (I) present in the reaction medium.

The reaction is preferably performed in a solvent of polar protic type and more preferably in a mixture of lower ($C_1$-$C_4$) alkanol and water, such as a mixture of ethanol and water or of methanol and water.

The reaction temperature advantageously ranges between 35° C. and 120° C. and better still between 40° C. and 100° C.

Methods A to D below are variants of the general process described above.

Method A

When X represents OH, a preferred embodiment of the general preparation process according to the invention follows the reaction scheme below:

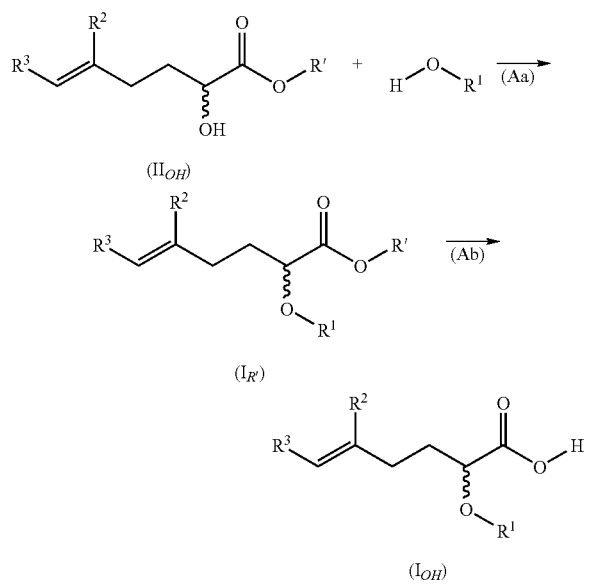

(Aa): THF/PPh$_3$/DEAD/room temp.
(Ab): EtOH/KOH/H$_2$O reflux in which reaction scheme $R^1$, $R^2$ and $R^3$ are as defined above for formula (I), R' represents R as defined above, with the exception of hydrogen, the compound ($II_{OH}$) being the compound of the formula (II) in which X represents —OH, the compound ($I_{R'}$) being the compound of the formula (I) in which R' represents an alkyl radical and the compound ($I_{OH}$) being the compound of the formula (I) in which R represents hydrogen. THF means tetrahydrofuran, PPh$_3$ means triphenylphosphine, DEAD means diethyl azodicarboxylate, "room temp." means room temperature, ETOH is ethanol and KOH is potassium hydroxide.

In the above reaction scheme, the saponification reaction step (Ab) is optional, i.e. it is performed only in the case where the desired compound of the formula (I) is a carboxylic acid (R=H).

This embodiment and the compounds of the formula (I) thereby obtained are illustrated in Examples 1 and 2.

Method B

According to one embodiment of the process according to the invention, the compounds of the formula ($I_G$), which is a special case of the compounds of the formula (I) in which $R^1$ represents an aryl radical substituted by a radical G, as defined above, can advantageously be prepared according to the following reaction scheme:

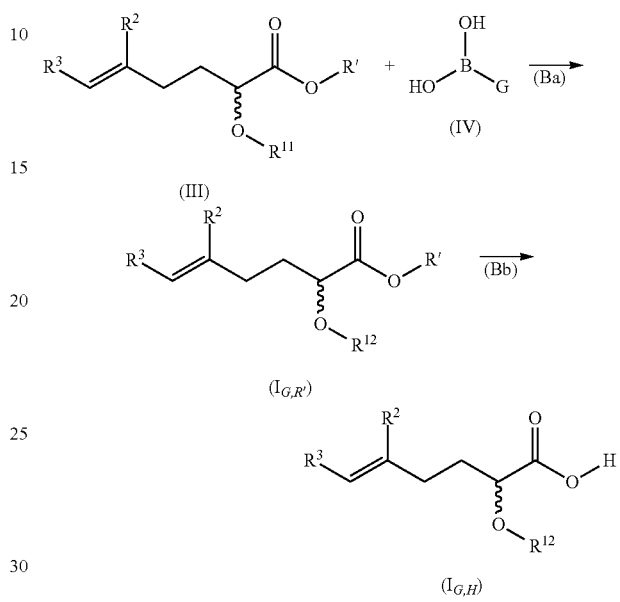

(Ba): CH$_3$OCH$_2$CH$_2$OCH$_3$/Pd(PPh$_3$)$_4$/Na$_2$CO$_3$/H$_2$O
(Bb): EtOH/KOH/H$_2$O/reflux in which reaction scheme:
$R^2$ and $R^3$ are as defined above for formula (I);
R' represents R, as defined above, with the exception of hydrogen;
$R^{11}$ represents $R^1$, as defined above, bearing a group that is reactive with the derivative of the formula (IV) and chosen especially from a bromine or iodine atom and a CF$_3$SO$_3$— radical, bromine and iodine being the preferred reactive groups; and
$R^{12}$ represents $R^{11}$, in which the group that is reactive with the derivative of the formula (IV) has been substituted by the radical G.

As indicated in the above reaction schemes, the saponification step (Bb) is optional. The compounds of the formulae ($I_{G, R'}$) and ($I_{G, H}$) form the set of compounds of the formula ($I_G$), which is a special case of the compounds of the formula (I) in which $R^1$ represents an aryl radical substituted by a radical G.

Thus, the compounds of the formula (I) in which $R^1$ represents aryl substituted by a monocyclic, bicyclic or tricyclic aromatic heterocyclic group comprising one or more hetero atoms chosen from O, N and S, and optionally substituted by one or more radicals T as defined above, or alternatively in which $R^1$ represents an aryl group optionally substituted by one or more radicals T, can be prepared by reaction of the corresponding compound of the formula (I) in which $R^1$ represents aryl substituted by a halogen atom, such as chlorine, bromine or iodine, with a compound of the formula (IV) defined in the above reaction scheme, in which G represents a monocyclic, bicyclic or tricyclic aromatic heterocyclic group comprising one or more hetero atoms chosen from O, N and S, and optionally substituted by one or more radicals T as defined above when $R^1$, in the final compound, represents aryl substituted by such a heterocyclic group, or alternatively G represents aryl optionally substituted by one or more radicals T when, in the final compound, $R^1$ represents aryl substituted by an aryl group, which is itself optionally substituted by one or more radicals T.

Advantageously, from 1.5 to 5 equivalents and preferably from 1.5 to 3 equivalents of the compound of the formula (IV) are incorporated relative to the amount of compound of the formula (III) present in the reaction medium.

This reaction is preferably performed in a polar aprotic solvent in the presence of a palladium 0 complex and a base.

A linear or cyclic ether, such as those defined above is more particularly suitable as solvent. Dimethoxyethane is preferred.

The base that will be used is any of the mineral bases mentioned above and advantageously sodium carbonate. For example, from 1.5 to 5 equivalents and preferably from 1.5 to 3 equivalents of base, relative to the amount of compound of the formula (III), can be introduced into the reaction medium.

According to one preferred embodiment, the amounts of base and of compound of the formula (IV) are equivalent The amount of palladium 0 complex used is catalytic. Usually, from 0.001 to 1 equivalent and preferably from 0.01 to 0.1 equivalent of the said complex is used. An example of a palladium 0 complex that can be used is tetrakis(triphenylphosphine)-palladium 0.

The reaction temperature advantageously ranges between 50° C. and 120° C. and preferably between 70° C. and 90° C.

This embodiment and the compounds resulting therefrom are illustrated in Examples 3 and 4.

Method C

In the starting compound of the formula (II) defined above, when X represents halogen, for example a chlorine atom, one preferred embodiment of the process according to the invention adopts the following reaction scheme:

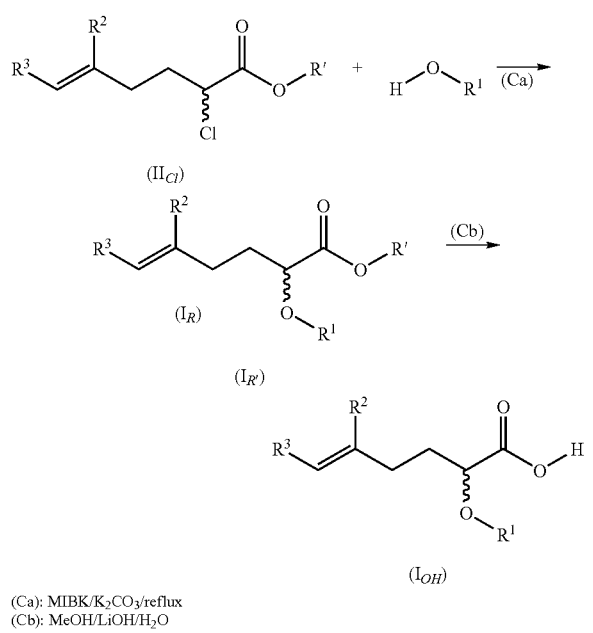

(Ca): MIBK/$K_2CO_3$/reflux
(Cb): MeOH/LiOH/$H_2O$ in which reaction scheme $R^1$, $R^2$ and $R^3$ are as defined above for formula (I), R' represents R, as defined above, with the exception of hydrogen, the compound ($II_{Cl}$) being the compound of the formula (II) in which X represents a chlorine atom, the compound ($I_{R'}$) being the compound of the formula (I) in which R represents an alkyl radical, and the compound ($I_{OH}$) being the compound of the formula (I) in which R represents hydrogen. The set of compounds of the formulae ($I_{R'}$) and ($I_{OH}$) together form the set of compounds of the formula (I) according to the invention. MIBK means methyl isobutyl ketone, $K_2CO_3$ means potassium carbonate, MeOH is methanol and LiOH is lithium hydroxide.

In the above reaction scheme, the saponification reaction step (Cb) is optional, i.e. it is performed only in the case where the desired compound of the formula (I) is a carboxylic acid (R=H).

This embodiment, and the compounds of the formula (I) thereby obtained, are illustrated in Examples 5 and 6.

Method D

The compounds of the formula (I) can also be prepared according to a synthetic route using compounds grafted onto a resin of Wang bromo type, according to the following reaction scheme:

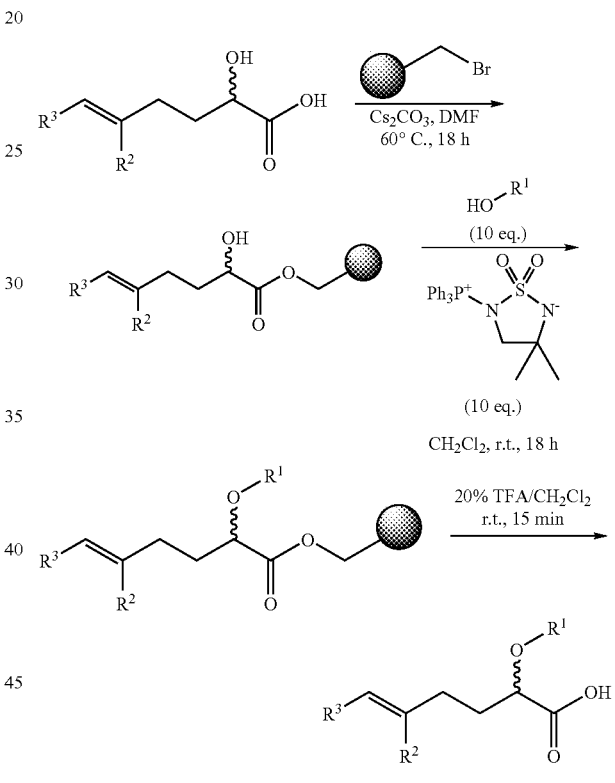

in which scheme $R^1$, $R^2$ and $R^3$ are as defined for the general formula (I).

In the above reaction scheme, a mixture of α-hydroxy acid and caesium carbonate, in a polar aprotic solvent, for instance dimethylformamide, is treated with a suspension of resin, so as to obtain the resin-grafted α-hydroxy acid derivative.

The alcohol $R^1$—OH is then added to this derivative in the presence of a phosphine, such as 4,4-dimethyl-2-(triphenylphosphanyl)(1,2,5)-thiadiazolidine. The reaction is performed, generally at room temperature, for a time is possibly ranging from one to several hours, for example about 18 hours.

The compound is then detached from the resin according to standard techniques, for example using trifluoroacetic acid, to give the carboxylic acid of the formula ($I_{OH}$) obtained in the last step of the above reaction scheme. This carboxylic acid is a special case of the compound of the formula (I) in which R represents hydrogen, and can optionally be readily converted into a compound of the formula (I) in which R has the definition indicated above for the set of compounds according to the invention, with the exception of hydrogen, via any method known per se.

This embodiment, and the compounds of the formula (I) thereby obtained, are illustrated in Example 7.

In the processes described above, it should be understood that the operating conditions can vary substantially depending on the various substituents present in the compounds of the formula (I) that it is desired to prepare. Such variations and adaptations are readily available to a person skilled in the art, for example from scientific reviews, the patent literature, Chemical Abstracts, and computer databases, including the Internet. Similarly, the starting materials are either commercially available or are available no via syntheses that a person skilled in the art can readily find, for example in the various publications and databases described above.

The optical isomers of the compounds of the formula (I) can be obtained, on the one hand, via standard techniques for separating and/or purifying isomers, known to those skilled in the art, from the racemic mixture of the compound of the formula (I). The optical isomers can also be obtained directly via stereoselective synthesis of an optically active starting compound.

The examples that follow illustrate the present invention without limiting it in any way. In these examples and in the proton nuclear magnetic resonance (300 MHz NMR) data, the following abbreviations have been used: s for singlet, d for doublet, t for triplet, q for quartet, o for octet and m for complex multiplet. The chemical shifts δ are expressed in ppm. "M.p." means "melting point".

EXAMPLES

Example 1

Process for the preparation of ethyl 2-[(4-trifluoromethylphenyl)oxy]-4-cyclohex-1-en-1-ylbutanoate 1.1 g (0.0071 mol) of 4-trifluoromethylphenol and 1.5 g (0.0071 mol) of ethyl 4-cyclohex-1-en-1-yl-2-hydroxybutanoate (B. B. Snider, *J. Org. Chem.*, (1984), 1688-1691) are added to a solution of 2.8 g (0.0071 mol+50%) of triphenylphosphine in 70 ml of tetrahydrofuran (THF), and a solution of 1.8 g (0.0071 mol+50%) of diethyl azodicarboxylate (DEAD) in 7 ml of THF are added, at 0° C. The solution is allowed to return to room temperature with stirring, and is reacted overnight. The reaction medium is concentrated, taken up in 1N sodium hydroxide (NaOH) solution and extracted with ethyl acetate (EtOAc). The extract is washed with saturated sodium chloride (NaCl) solution and then dried over sodium sulfate ($Na_2SO_4$). After concentrating, the oil obtained is taken up in 150 ml of an ether/hexane mixture: a white precipitate (O=$PPh_3$) is formed, which is removed by suction-filtering.

The solution is concentrated again. The product is purified by flash chromatography (98/2 heptane/ethyl acetate).

2.0 g of a colourless oil are obtained.
Yield=80%
$^1$H NMR ($CDCl_3$, 300 MHz): 1.45 (3H, t, J=7 Hz); 1.71-1.87 (4H, m); 2.15-2.35 (8H, m); 4.39-4.46 (2H, q, J=7 Hz); 4.84 (1H, t, J=6 Hz), 5.61 (1H, s); 7.14 (2H, d, J=8 Hz); 7.74 (2H, d, J=8 Hz).

Example 2

Process for the preparation of 4-cyclohex-1-enyl-2-[4-(trifluoromethyl)phenoxy]butanoic acid The ester obtained above (1.8 g; 0.005 mol) is dissolved in 20 ml of ethanol. After addition of 1.7 g of 85% potassium hydroxide (KOH) (5 equivalents), the solution is refluxed for 30 minutes. After adding 10 ml of water, refluxing is continued for 4 hours. The reaction medium is concentrated. The oil obtained is taken up in water and washed with ether. The aqueous phase is acidified with 1N hydrochloric acid (HCl) and then extracted with ethyl acetate. The extract is dried over $Na_2SO_4$ and then concentrated. The solid obtained is recrystallized from 50 ml of heptane. 1.1 g of a white solid are obtained.
Yield=75%
m.p.: 109-111° C.
$^1$H NMR ($CDCl_3$, 300 MHz). 1.36-1.76 (4H, m); 1.76-2.02 (4H, m); 4.02-2.29 (4H, m); 4.68 (1H, m); 5.39 (1H, s); 6.94 (2H, d, J=8.3 Hz); 7.54 (2H, d, J=8.3 Hz).
Mass spectrometry: (ES) M-H=327.2

Example 3

Process for the preparation of ethyl 2-[4-(5-chlorothiophen-2-yl)-phenoxy]-4-cyclohex-1-enylbutanoate 0.18 g (0.04 equivalent) of Pd($PPh_3$)$_4$ and then 1.2 g (0.0084 mol) of 5-chloro-2-thiopheneboronic acid are added to a solution of 1.4 g (0.0038 mol) of ethyl 2-[(4-bromophenyl)oxy]-4-cyclohex-1-en-1-ylbutanoate in 20 ml of dimethoxyethane. 4.2 ml of 2M sodium carbonate solution are added at room temperature. The reaction mixture is stirred overnight and then refluxed for 2 hours. After cooling to room temperature, the mixture is taken up in water and extracted with ethyl acetate. The extract is washed with 1N sodium hydroxide and then with saturated aqueous NaCl solution and finally dried over $Na_2SO_4$. After concentrating, the black oil obtained is purified by flash chromatography (95/5 heptane/ethyl acetate). 1.1 g of a thick oil are obtained.
Yield=73%
$^1$H NMR ($CDCl_3$, 300 MHz): 1.48 (3H, t, J=7 Hz); 1.78-1.83 (4H, m); 2.18-2.38 (8H, m); 4.42-4.49 (2H, q, J=7 Hz); 4.83 (1H, t, J=6 Hz); 5.56 (1H, s); 7.07-7.18 (4H, m); 7.61 (2H, d, J=8 Hz).

Example 4

Process for the preparation of 2-[4-(5-chlorothiophen-2-yl)-phenoxy]-4-cyclohex-1-enylbutanoic acid The ester obtained above in Example 3 (1.1 g, 0.0027 mol) is dissolved in 25 ml of ethanol. 0.5 g (0.0081 mol) of 85% potassium hydroxide is added and the mixture is refluxed for 30 minutes. 12.5 ml of water are added and refluxing is continued for a further 4 hours. After cooling to room temperature, the reaction medium is concentrated, taken up in water and washed with ether. The aqueous phase is acidified with 1N HCl. The white precipitate formed is extracted with dichloromethane and dried over $Na_2SO_4$. 0.9 g of a cream-coloured solid melting at 136-138° C. is obtained.
Yield=90%
$^1$H NMR ($CDCl_3$, 300 MHz): 1.40-1.73 (4H, m); 1.81-2.03 (4H, m); 2.03-2.28 (4H, m); 4.66 (1H, m); 5.41 (1H, s); 6.76-7.02 (4H, m); 7.34-7.51 (2H, m).

Example 5

Process for the preparation of methyl 4-cyclohex-1-en-1-yl-2-[(4'-methoxy-1,1'-biphenyl-4-yl)oxy]butanoate 1.9 g (0.0138 mol) of potassium carbonate are added to a solution of 1.4 g (0.0069 mol) of 4'-methoxy-1,1'-biphenyl-4-ol in 30 ml of 3-methyl-2-pentanone (MIBK). The mixture is refluxed for 30 minutes and a solution of 1.5 g (0.0069 mol) of methyl 2-chloro-4-cyclohex-1-en-1-ylbutanoate in 10 ml of 3-methyl-2-pentanone is then added. Refluxing is continued for a further 6 hours. After cooling to room temperature, the reaction medium is concentrated, taken up in water and extracted with ethyl acetate. The extracts are washed with 1N sodium hydroxide and then with saturated aqueous NaCl solution, and dried over $Na_2SO_4$. After concentrating, a thick oil is obtained, which is purified by flash chromatography (95/5 heptane/ethyl acetate) 1.1 g of an oily product are thus obtained.

Yield=42%

$^1$H NMR ($CDCl_3$, 300 MHz): 1.43-1.47 (4H, m); 1.88-2.10, 8H, m); 3.66 (3H, s); 3.75 (3H, s); 4.57 (1H, t, J=6 Hz); 5.36 (1H, s); 6.83-6.89 (4H, m); 7.36-7.41 (4H, m).

Example 6

Process for the preparation of 4-cyclohex-1-enyl-2-(4'-methoxy-1,1'-biphenyl-4-yloxy)butanoic acid The ester obtained above in Example 5 (1.0 g, 0.0026 mol) is dissolved in 20 ml of methanol. A solution of 26 ml of 1M LiOH.$H_2O$ is added at room temperature. The milky suspension is refluxed for 1 hour. After concentrating the reaction medium, the white solid obtained is taken up in ½ HCl. The suspension is stirred for 30 minutes and then extracted with ethyl acetate. After concentrating, 0.6 g of a white solid with a melting point of 152-154° C. is obtained.

Yield=63%

$^1$H NMR ($CDCl_3$, 300 MHz): 1.42-1.74 (4H, m); 1.82-2.04 (4H, m); 2.04-2.36 (4H, m); 3.83 (3H, s); 4.68 (1H, m); 5.42 (1H, s); 6.95 (4H, m); 7.46 (4H, m).

Example 7

Process for the preparation of 4-cyclohex-1-enyl-2-[4-(2-methoxycarbonylvinyl)phenoxy]butanoic acid A 20% solution of caesium carbonate in water (23 ml, 14.4 mmol) is added to a solution of 4-cyclohex-1-enyl-2-hydroxybutyric acid (7 g, 38 mmol) in methanol (200 ml). After stirring for 10 minutes, the solvents are evaporated off and the residue is taken up in toluene, which is then evaporated off. The residue is taken up in dimethylformamide (DMF) (125 ml), and a suspension of Wang bromo resin (23.7, 18 mmol) in DMF (125 ml) is then added. The mixture is stirred for 18 hours at 60° C. The resin is then washed several times with THF (3×150 ml, 2 minutes), 1/1 THF/$H_2O$ (3×150 ml, 2 minutes), methanol (MeOH) (3×150 ml, 2 minutes), dichloromethane (3×150 ml, 2 minutes) and MeOH (3×150 ml, 2 minutes). The resin is dried under vacuum at 50° C.

A solution of ethyl 3-(4-hydroxyphenyl)prop-2-enoate (1 mmol) in dichloromethane (2 ml) is added to the grafted resin (150 mg, 0.1 mmol). A solution of 4,4-dimethyl-2-(triphenylphosphanyl)-1,2,5-thiadiazolidine (1 mmol) in dichloromethane (8 ml) is then added and this suspension is stirred at room temperature for 18 hours. The resin is filtered and washed with DMF (5 ml), 50/50 DMF/$H_2O$ (5 ml), MeOH (2×5 ml) and 80/20 DCM/DCE (3×5 ml). The resin is then treated with a 20/80 solution of TFA/DCM (trifluoroacetic acid/dichloromethane) for 15 minutes. The resin is filtered off and washed with dichloromethane (2×5 ml). The filtrate is evaporated and the residue is purified by preparative LCMS to give 3.20 mg of the expected product in the form of an oil.

Mass spectrometry M-H: 343.3

According to protocols similar to those described for obtaining the compounds of Examples 1 to 7 above, the compounds presented in Table 1 below were obtained.

TABLE 1

| Ex. | STRUCTURE | Method | M.p. (° C.) | NMR | MASS |
|---|---|---|---|---|---|
| 8 | 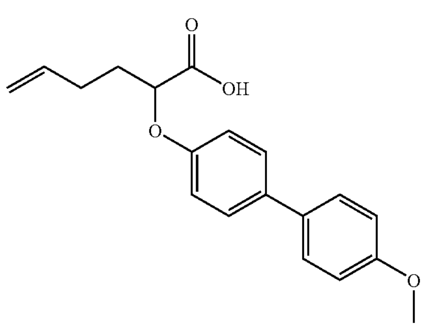 | A | 128-130 | ($CDCl_3$): 1.98-2.22 (2H, m); 2.23-2.52 (2H, m); 3.83 (3H, s); 4.71 (1H, m); 4.90-5.20 (2H, m); 5.83 (1H, m); 6.83-7.09 (4H, m); 7.36-7.63 (4H, m). | |
| 9 | 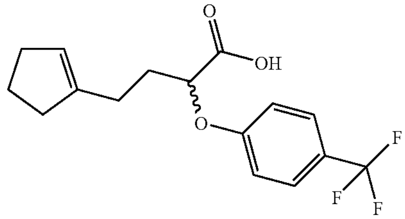 | A | | ($CDCl_3$): 1.70-2.01 (2H, m); 2.03-2.51 (8H, m); 4.70 (1H, m); 5.36 (1H, s); 6.94 (2H, d, J = 8.7 Hz); 7.54 (2H, d, J = 8.7 Hz). | |

TABLE 1-continued

| Ex. | STRUCTURE | Method | M.p. (° C.) | NMR | MASS |
|---|---|---|---|---|---|
| 10 | 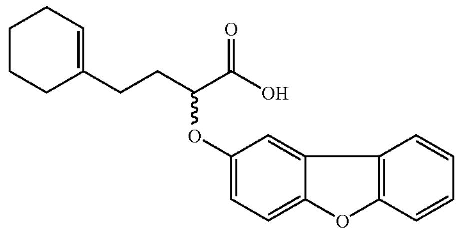 | A | 142-144° C. | (CDCl₃): 1.36-1.74 (4H, m); 1.79-2.04 (4H, m); 2.04-2.32 (4H, m); 4.72 (1H, m); 5.43 (1H, s); 7.07 (1H, m); 7.21-7.38 (1H, m); 7.38-7.63 (4H, m); 7.88 (1H, m). | (ES) M − H = 349.2 |
| 11 | 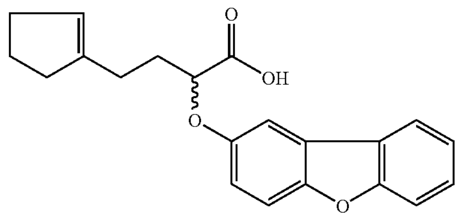 | A | 140-142° C. | (CDCl₃): 1.73-1.98 (2H, m); 2.05-2.62 (8H, m); 4.73 (1H, m); 5.37 (1H, m); 7.06 (1H, m); 7.22-7.38 (1H, m); 7.38-7.62 (4H, m); 7.88 (1H, m). | |
| 12 | 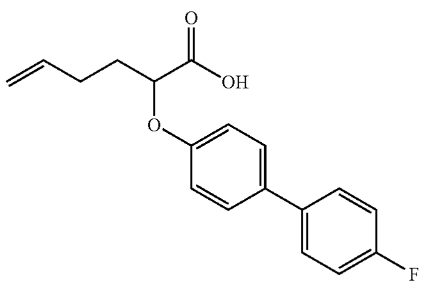 | B | 97° C. | (CDCl₃): 1.99-2.21 (2H, m); 2.22-2.44 (2H, m); 4.71 (1H, m); 4.91-5.16 (2H, m); 5.72-5.93 (1H, m); 6.96 (2H, m); 7.08 (2H, m); 7.34-7.59 (4H, m). | |
| 13 | 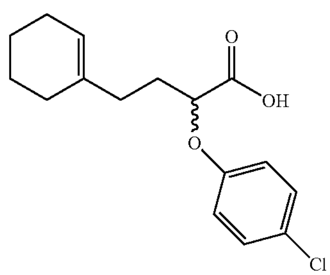 | A | | (CDCl₃): 1.44-1.74 (4H, m); 1.77-2.43 (8H, m); 4.59 (1H, m); 5.39 (1H, s); 5.63 (1H, broad s); 6.82 (2H, d, J = 9.1 Hz); 7.23 (2H, d, J = 9.1 Hz). | (ES) M − H = 293.3/295.2 |
| 14 | 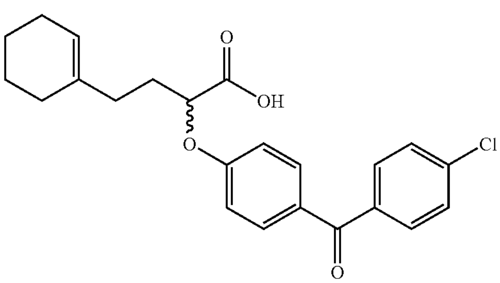 | A | | (CDCl₃): 1.44-1.73 (4H, m); 1.79-2.41 (8H, m); 4.75 (1H, m); 5.30 (1H, broad s); 5.40 (1H, s); 6.95 (2H, d, J = 9.1 Hz); 7.45 (2H, d, J = 8.7 Hz); 7.45 (2H, d, J = 8.7 Hz); 7.70 (2H, d, J = 8.7 Hz); 7.78 (2H, d, J = 9.1 Hz). | (ES) M + H = 399.3/401.3 |
| 15 | 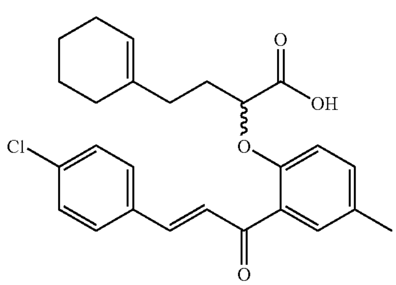 | A | | (CDCl₃): 1.45-1.73 (4H, m); 1.74-2.24 (8H, m); 2.36 (3H, m); 4.90 (1H, m); 5.41 (1H, m); 6.13 (1H, broad s); 6.96 (1H, m); 7.21-7.34 (2H, m); 7.40 (2H, m); 7.45 (1H, m); 7.57 (2H, m); 7.75 (1H, m). | (ES) M + H = 461.3/463.3 |

TABLE 1-continued

| Ex. | STRUCTURE | Method | M.p. (° C.) | NMR | MASS |
|---|---|---|---|---|---|
| 16 | 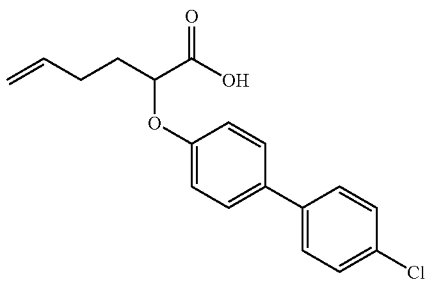 | A | 127° C. | (DMSO-d6): 1.97 (2H, m); 2.21 (2H, m); 4.73 (1H, m); 4.89-5.15 (2H, m); 5.84 (1H, m); 6.95 (2H, d, J = 8.7 Hz); 7.46 (2H, d, J = 8.7 Hz); 7.59 (2H, d, J = 8.7 Hz); 7.62 (2H, d, J = 8.7 Hz); 13.11 (1H, broad s). | |
| 17 | 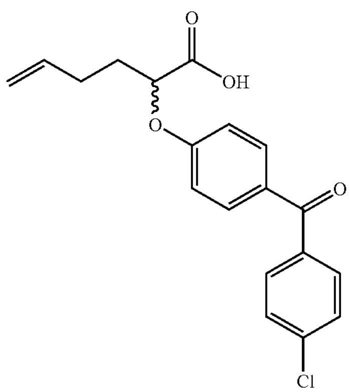 | A | 141° C. | (DMSO-d6): 1.99 (2H, m); 2.21 (2H, m); 4.85 (1H, m); 4.93-5.21 (2H, m); 5.84 (1H, m); 7.02 (2H, d, J = 8.7 Hz); 7.61 (2H, d, J = 8.7 Hz); 7.70 (2H, d, J = 8.7 Hz); 7.73 (2H, d, J = = 8.7 Hz); 13.25 (1H, broad s). | |
| 18 | 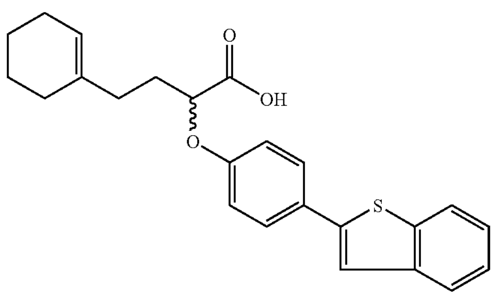 | B | 171-174° C. | (CDCl$_3$): 1.39-1.72 (4H, m); 1.78-2.03 (4H, m); 2.03-2.35 (4H, m); 4.70 (1H, m); 5.42 (1H, s); 6.95 (1H, m); 7.21-7.47 (4H, m); 7.55-7.68 (2H, m); 7.69-7.85 (2H, m). | |
| 19 | 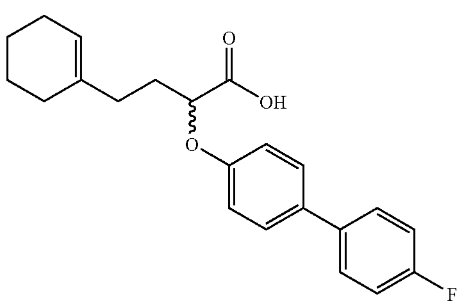 | B | 156-158° C. | (CDCl$_3$): 1.30-1.70 (4H, m); 1.70-1.95 (4H, m); 1.95-2.25 (4H, m); 4.65 (1H, m); 5.35 (1H, s); 6.80-7.60 (8H, m). | |
| 20 | 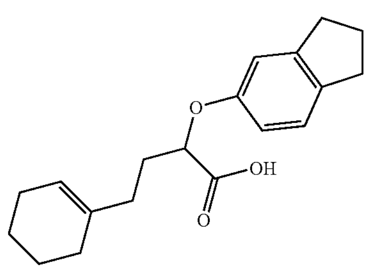 | D | | | (ES) M − H = 299.3 |

TABLE 1-continued

| Ex. | STRUCTURE | Method | M.p. (° C.) | NMR | MASS |
|-----|-----------|--------|-------------|-----|------|
| 21 | 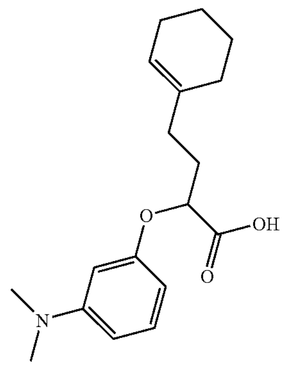 | D | | | (ES) M + H = 304.3 |
| 22 | 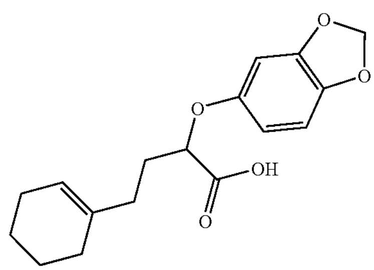 | D | | | (ES) M − H = 303.3 |
| 23 | 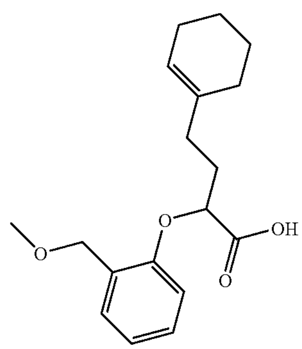 | D | | | (ES) M − H = 303.3 |
| 24 | 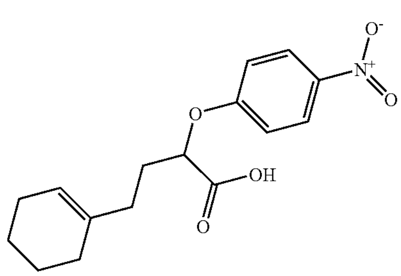 | D | | | (ES) M − H = 304.2 |
| 25 | 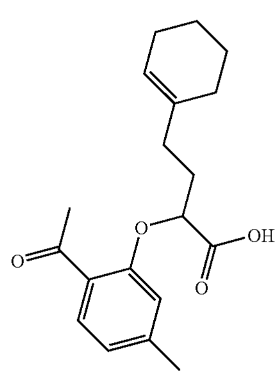 | D | | | (ES) M + H = 317.3<br>M − H = 315.3 |

TABLE 1-continued

| Ex. | STRUCTURE | Method | M.p. (° C.) | NMR | MASS |
| --- | --- | --- | --- | --- | --- |
| 26 | 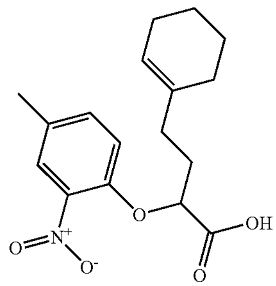 | D | | | (ES) M − H = 318.2 |
| 27 | 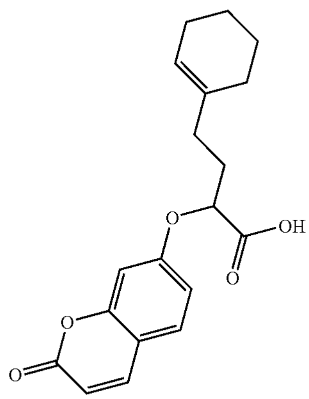 | D | | | (ES) M − H = 327.2 |
| 28 | 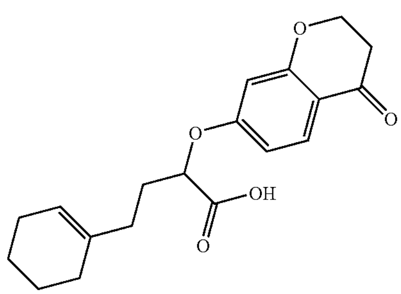 | D | | | (ES) M − H = 329.2 |
| 29 | 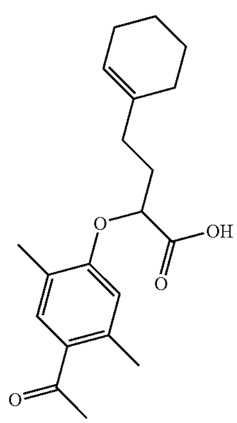 | D | | | (ES) M − H = 329.3 |

TABLE 1-continued
| Ex. | STRUCTURE | Method | M.p. (° C.) | NMR | MASS |
|---|---|---|---|---|---|
| 30 | 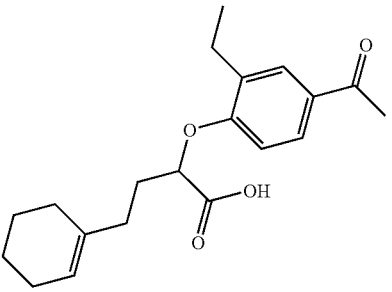 | D | | | (ES) M − H = 329.3 |
| 31 | 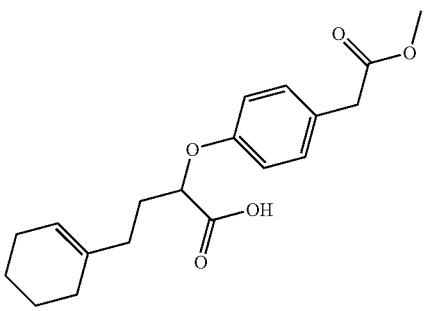 | D | | | (ES) M − H = 331.2 |
| 32 | 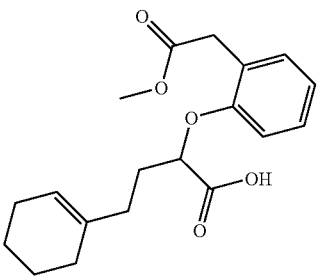 | D | | | (ES) M − H = 331.2 |
| 33 | 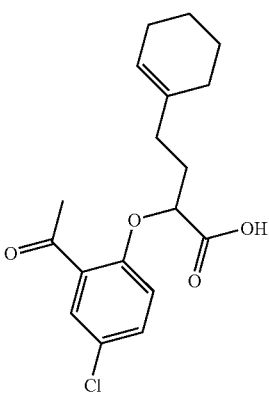 | D | | | (ES) M − H = 335.2/337.2 |

TABLE 1-continued

| Ex. | STRUCTURE | Method | M.p. (° C.) | NMR | MASS |
|---|---|---|---|---|---|
| 34 | 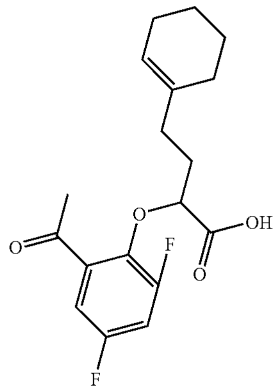 | D | | | (ES) M − H = 337.2 |
| 35 | 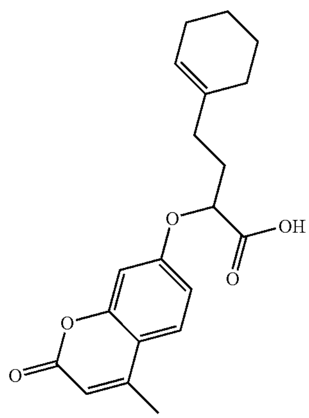 | D | | | (ES) M − H = 341.2 |
| 36 | 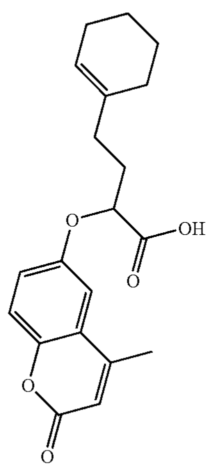 | D | | | (ES) M − H = 341.2 |
| 37 | 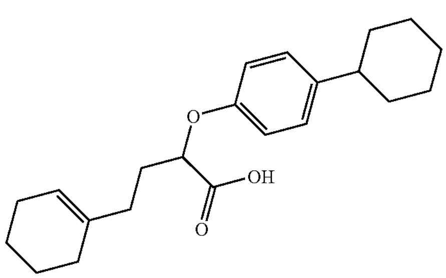 | D | | | (ES) M − H = 341.2 |

TABLE 1-continued

| Ex. | STRUCTURE | Method | M.p. (° C.) | NMR | MASS |
|---|---|---|---|---|---|
| 38 | 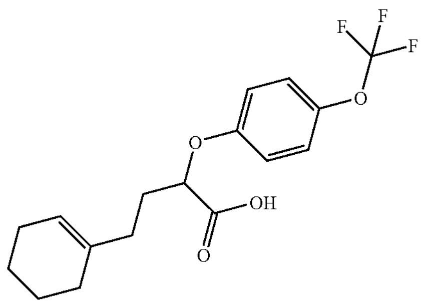 | D | | | (ES) M − H = 343.2 |
| 39 | 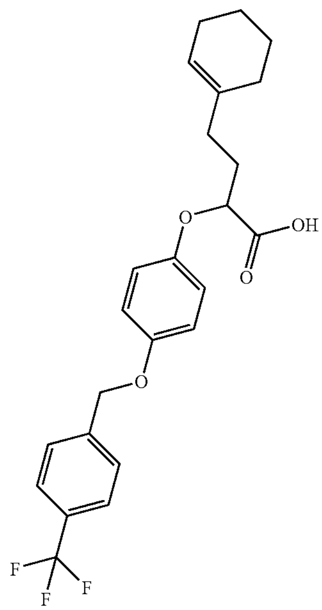 | D | | | (ES) M + H = 435.3 |
| 40 | 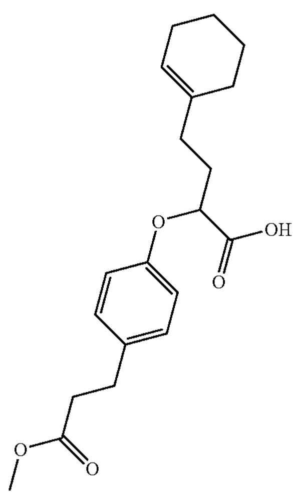 | D | | | (ES) M − H = 345.3 |

TABLE 1-continued

| Ex. | STRUCTURE | Method | M.p. (° C.) | NMR | MASS |
|---|---|---|---|---|---|
| 41 | 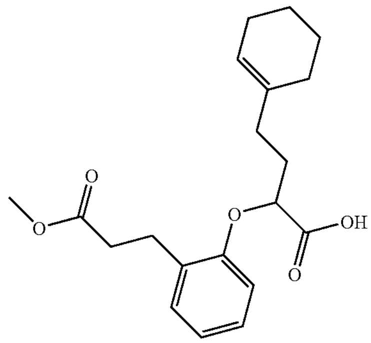 | D | | | (ES) M + 23 = 369.3 |
| 42 | 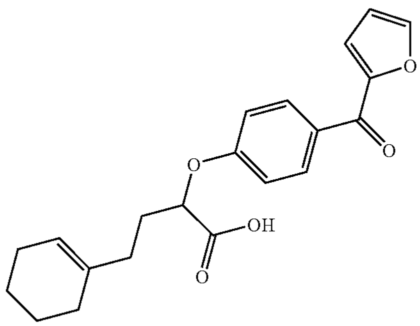 | D | | | (ES) M − H = 353.2 |
| 43 | 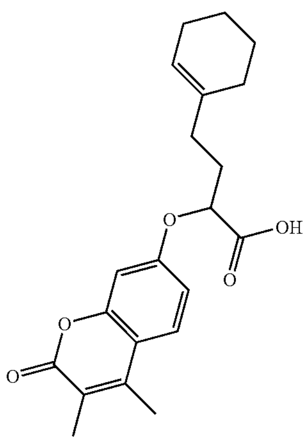 | D | | | (ES) M + H = 357.3 |
| 44 | 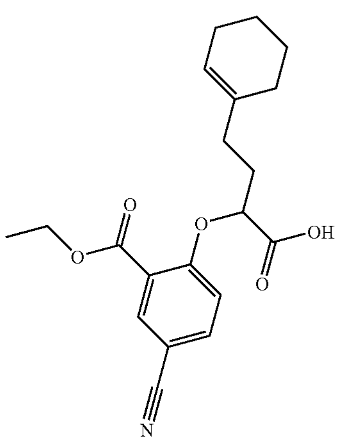 | D | | | (ES) M − H = 356.2 |

TABLE 1-continued
| Ex. | STRUCTURE | Method | M.p. (° C.) | NMR | MASS |
|---|---|---|---|---|---|
| 45 | 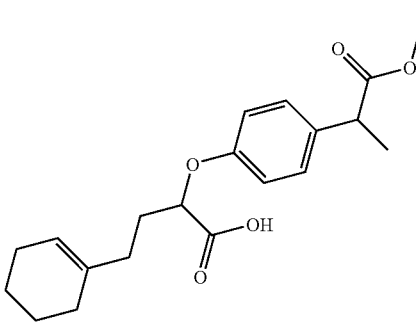 | D | | | (ES) M − H = 359.3 |
| 46 | 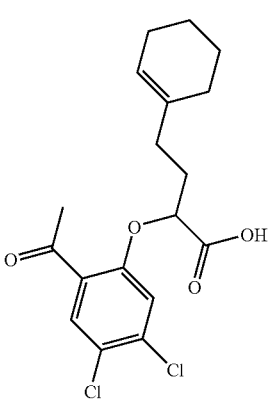 | D | | | (ES) M + H = 369.2/371.2 |
| 47 | 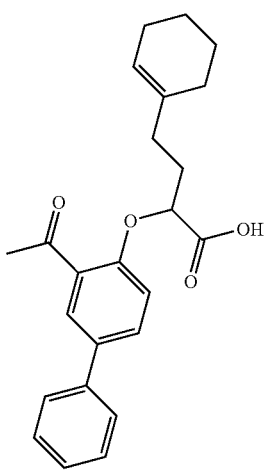 | D | | | (ES) M + H = 379.3<br>M − H = 377.3 |
| 48 | 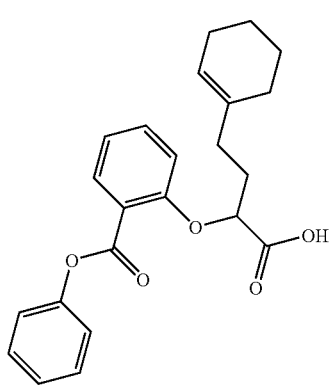 | D | | | (ES) M + 23<br>(adduct) = 403.2<br>M − H = 379.2 |

TABLE 1-continued

| Ex. | STRUCTURE | Method | M.p. (° C.) | NMR | MASS |
|---|---|---|---|---|---|
| 49 | 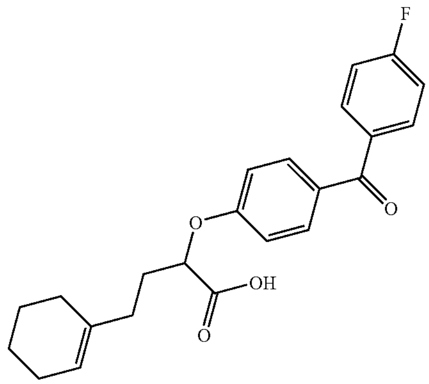 | D | | | (ES) M + H = 383.3<br>M − H = 381.3 |
| 50 | 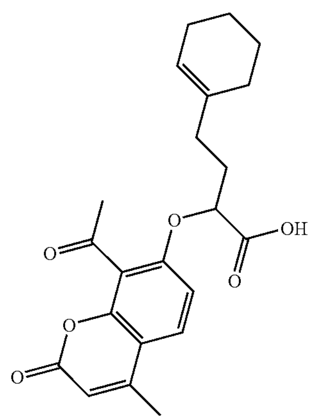 | D | | | (ES) M − H = 383.3 |
| 51 | 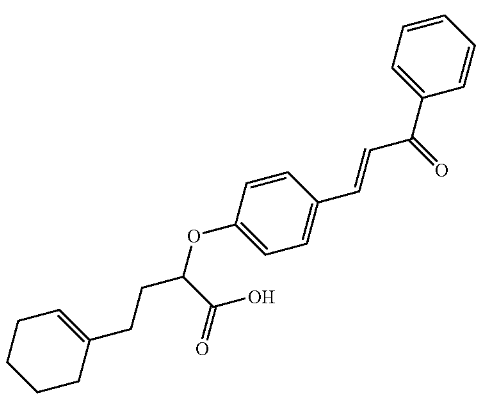 | D | | | (ES) M + H = 391.3<br>M − H = 389.3 |

TABLE 1-continued

| Ex. | STRUCTURE | Method | M.p. (° C.) | NMR | MASS |
|---|---|---|---|---|---|
| 52 | 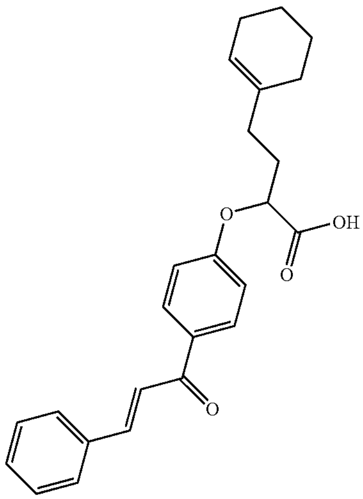 | D | | | (ES) M − H = 389.3 |
| 53 | 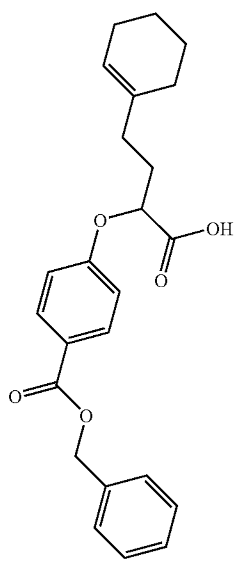 | D | | | (ES) M + H = 395.3<br>M − H = 393.3 |
| 54 | 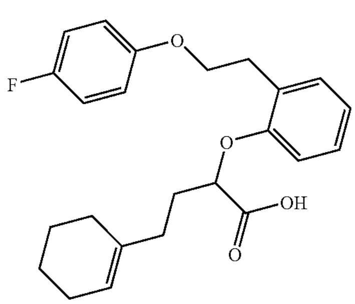 | D | | | (ES) M − H = 397.3 |

TABLE 1-continued

| Ex. | STRUCTURE | Method | M.p. (° C.) | NMR | MASS |
|---|---|---|---|---|---|
| 55 | 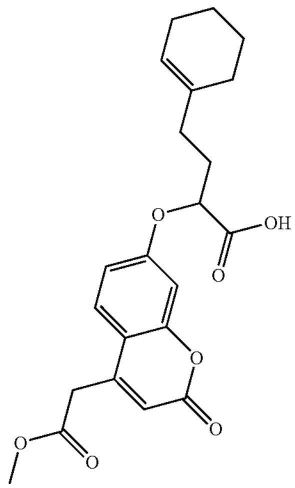 | D | | | (ES) M − H = 399.2 |
| 56 | 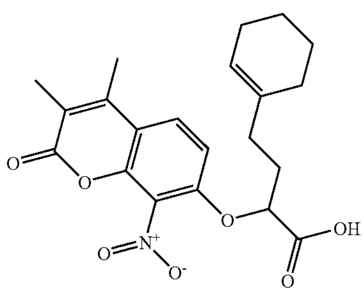 | D | | | (ES) M + H = 402.2<br>M − H = 400.2 |
| 57 | 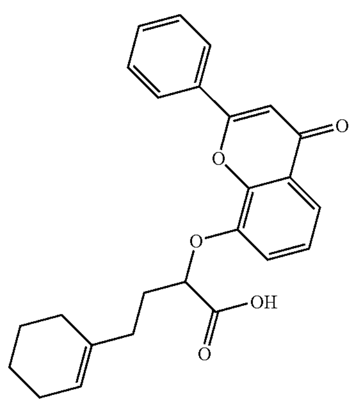 | D | | | (ES) M − H = 403.3 |
| 58 | 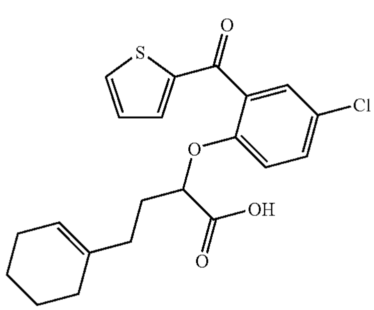 | D | | | (ES) M + H = 405.2/407.2<br>M − H = 403.1/405.2 |

TABLE 1-continued

| Ex. | STRUCTURE | Method | M.p. (° C.) | NMR | MASS |
|---|---|---|---|---|---|
| 59 | 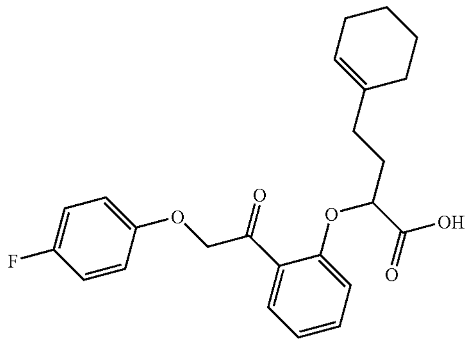 | D | | | (ES) M + H = 413.3<br>M − H = 411.3 |
| 60 | 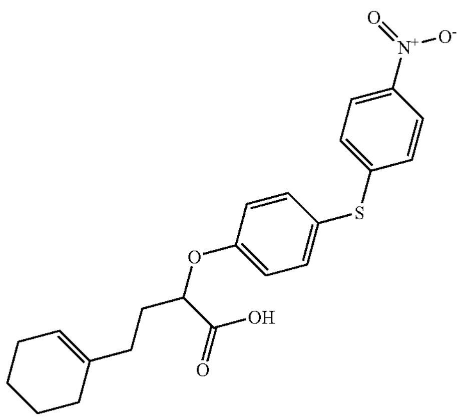 | D | | | (ES) M + H = 414.3<br>M − H = 412.3 |
| 61 | 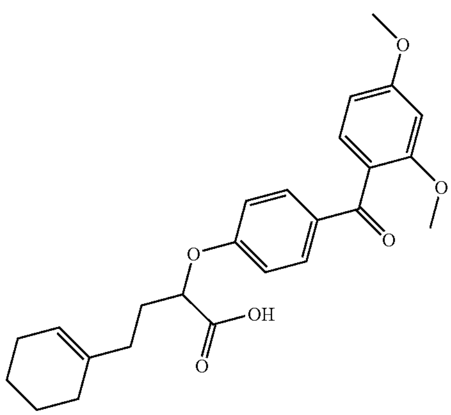 | D | | | (ES) M + H = 425.3<br>M − H = 423.3 |
| 62 | 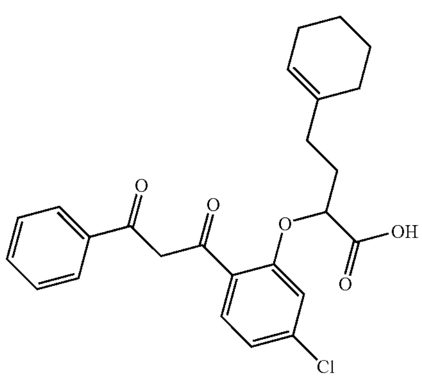 | D | | | (ES) M + H = 441.3/443.3<br>M − H = 439.2/441.2 |

TABLE 1-continued
| Ex. | STRUCTURE | Method | M.p. (° C.) | NMR | MASS |
|---|---|---|---|---|---|
| 63 | 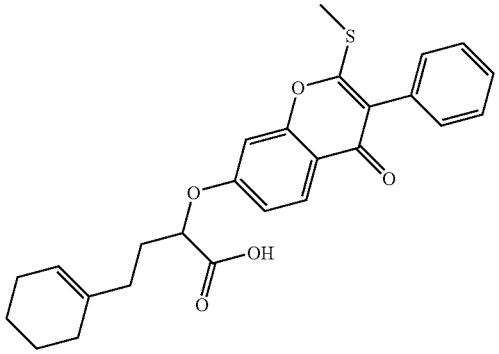 | D | | | (ES) M + H = 451.3<br>M − H = 449.3 |
| 64 | 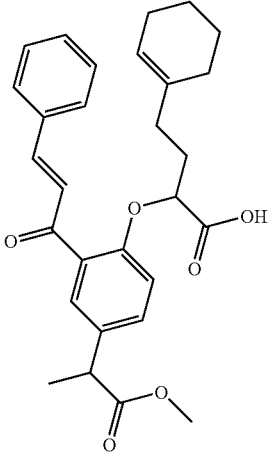 | D | | | (ES) M + H = 477.4<br>M − H = 475.3 |
| 65 | 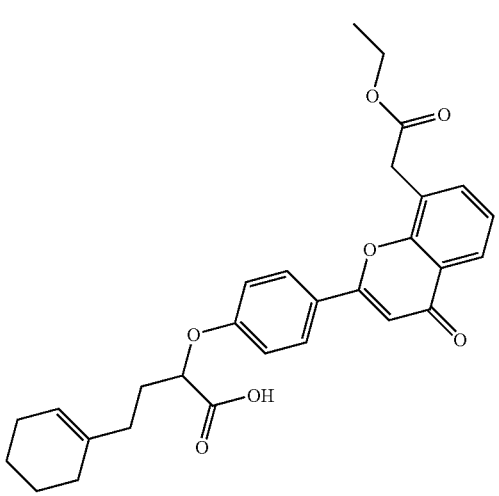 | D | | | (ES) M + H = 491.3<br>M − H = 489.3 |

TABLE 1-continued

| Ex. | STRUCTURE | Method | M.p. (° C.) | NMR | MASS |
|---|---|---|---|---|---|
| 66 | 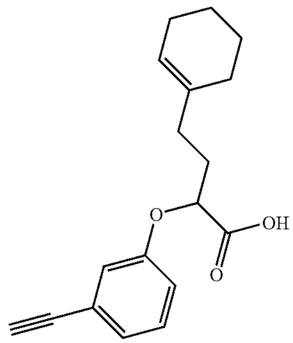 | D | | | (ES) M − H = 283.2 |
| 67 | 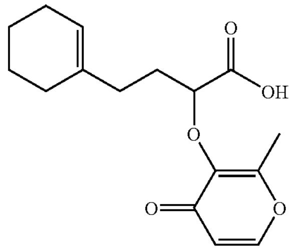 | D | | | (ES) M + H = 293.2<br>M − H = 291.2 |
| 68 | 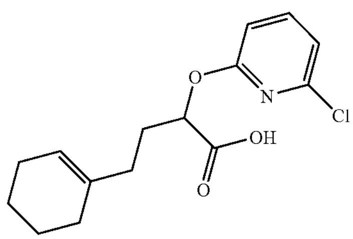 | D | | | (ES) M + H = 296.2/298.2<br>M − H = 294.2/296.2 |
| 69 | 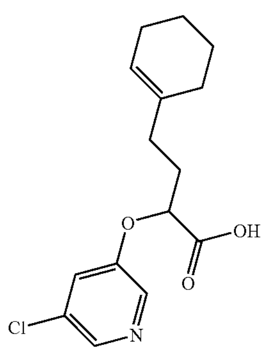 | D | | | (ES) M + H = 296.2/298.2<br>M − H = 294.2/296.2 |
| 70 | 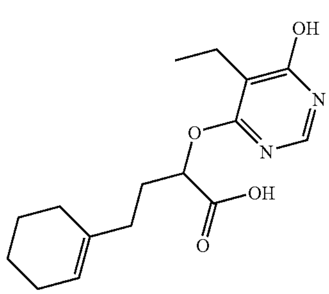 | D | | | (ES) M − H = 305.2 |

TABLE 1-continued
| Ex. | STRUCTURE | Method | M.p. (° C.) | NMR | MASS |
|---|---|---|---|---|---|
| 71 | 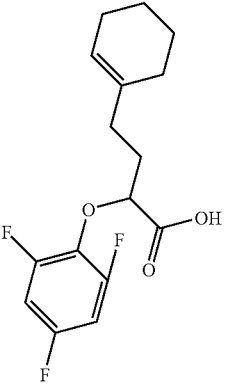 | D | | | (ES) M − H = 313.2 |
| 72 | 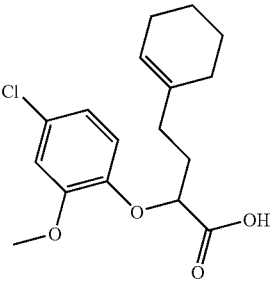 | D | | | (ES) M + H = 325.3/327.2<br>M − H = 323.2/325.2 |
| 73 | 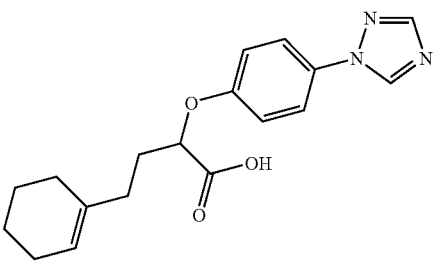 | D | | | (ES) M + H = 328.3<br>M − H = 326.3 |
| 74 | 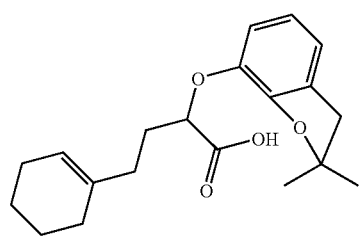 | D | | | (ES) M + H = 331.3<br>M − H = 329.3 |
| 75 | 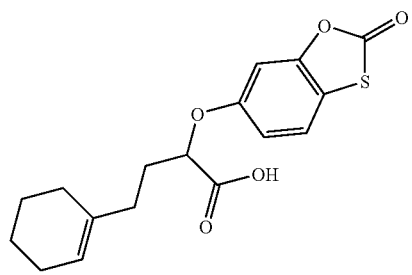 | D | | | (ES) M + H = 335.2<br>M − H = 333.2 |

TABLE 1-continued

| Ex. | STRUCTURE | Method | M.p. (° C.) | NMR | MASS |
|---|---|---|---|---|---|
| 76 | 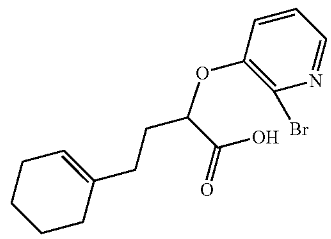 | D | | | (ES) M + H = 340.2/342.2<br>M − H = 338.2/340.2 |
| 77 | 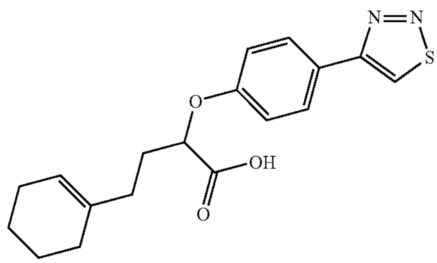 | D | | | (ES) M + H = 345.2<br>M − H = 343.2 |
| 78 | 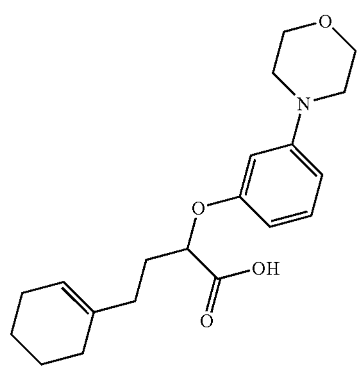 | D | | | (ES) M + H = 346.3 |
| 79 | 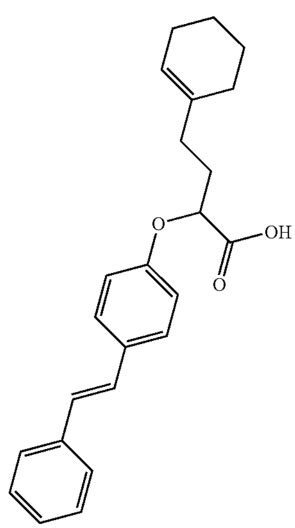 | D | | | (ES) M − H = 361.3 |

TABLE 1-continued

| Ex. | STRUCTURE | Method | M.p. (° C.) | NMR | MASS |
|---|---|---|---|---|---|
| 80 | 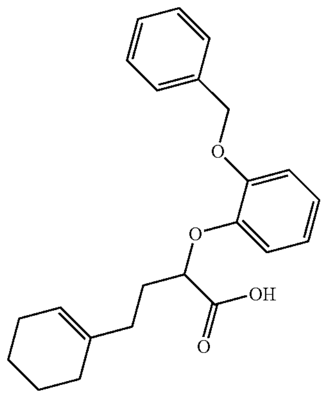 | D | | | (ES) M − H = 365.3 |
| 81 | 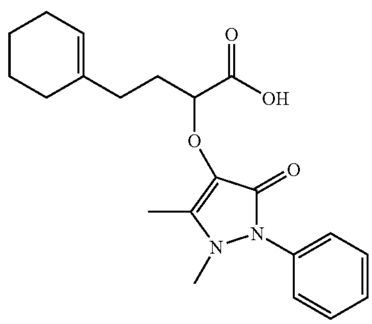 | D | | | (ES) M + H = 371.3<br>M − H = 369.3 |
| 82 | 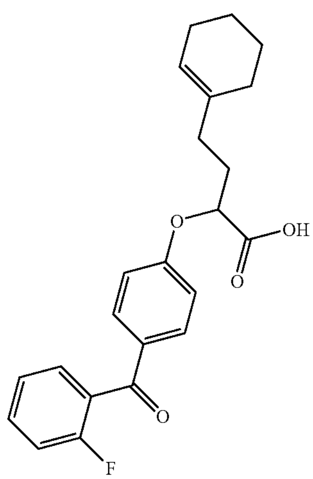 | D | | | (ES) M + H = 383.3<br>M − H = 381.3 |
| 83 | 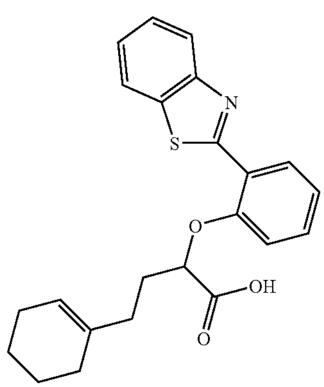 | D | | | (ES) M + H = 394.3 |

TABLE 1-continued

| Ex. | STRUCTURE | Method | M.p. (° C.) | NMR | MASS |
| --- | --- | --- | --- | --- | --- |
| 84 | 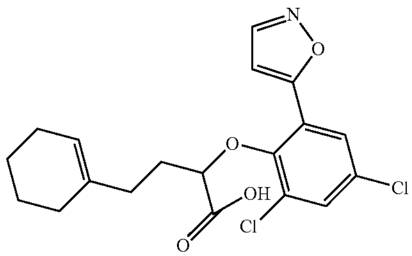 | D | | | (ES) M + H = 396.2/398.2<br>M − H = 394.2/396.2 |
| 85 | 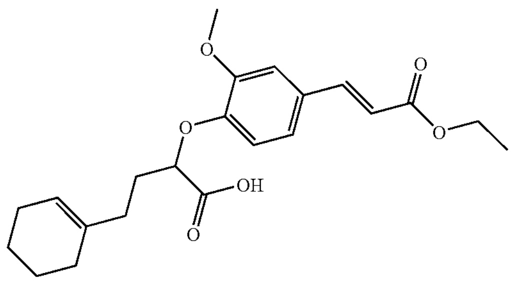 | D | | | (ES) M + H = 389.3<br>M − H = 387.3 |
| 86 | 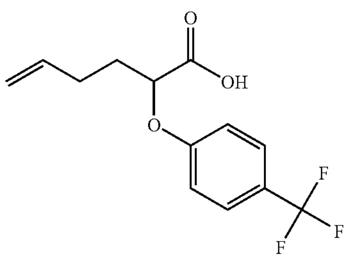 | A | 70° C. | (CDCl$_3$): 1.96-2.20 (2H, m); 2.20-2.43 (2H, m); 4.70-4.74 (1H, m); 4.88-5.31 (2H, m); 5.80 (1H, m); 6.95 (2H, d, J = 8.7 Hz); 7.55 (2H, d, J = 8.7 Hz); 9.79 (1H, broad s). | |
| 87 | 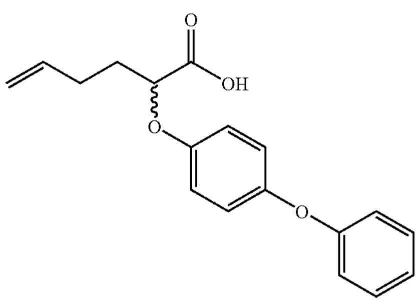 | A | 61° C. | (CDCl$_3$): 1.92-2.18 (2H, m); 2.18-2.47 (2H, m); 4.53-4.67 (1H, m); 4.90-5.16 (2H, m); 5.65-5.95 (1H, m); 6.76-7.12 (7H, m); 7.12-7.40 (2H, m); 11.06 (1H, broad s). | |
| 88 | 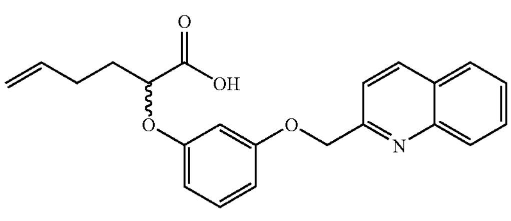 | A | 125° C. | (CDCl$_3$): 1.99-2.21 (2H, m); 2.21-2.46 (2H, m); 4.61-4.74 (2H, m); 4.61-4.74 (1H, m); 5.24 (2H, s); 5.72-5.94 (1H, m), 6.37-6.66 (3H, m); 6.99-7.12 (3H, m); 7.47-7.87 (4H, m); 8.09-8.29 (2H, m) acid H, very broad s | |
| 89 | 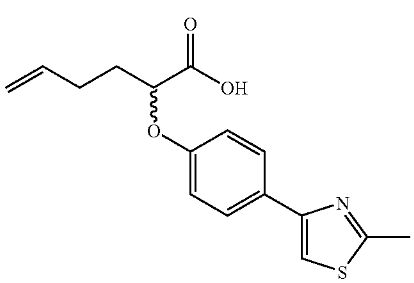 | A | 120° C. | (CDCl$_3$): 1.96-2.22 (2H, m); 2.22-2.48 (2H, m); 2.77 (3H, s); 4.51-4.70 (1H, m); 4.90-5.14 (2H, m); 5.71-5.98 (1H, m); 6.82-6.98 (2H, m); 7.13 (1H, s); 7.62-7.79 (2H, m). | |

TABLE 1-continued

| Ex. | STRUCTURE | Method | M.p. (° C.) | NMR | MASS |
|---|---|---|---|---|---|
| 90 | 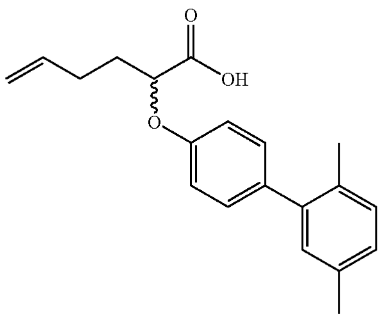 | A | 95-98° C. | (CDCl₃): 2.03-2.20 (2H, m); 2.24 (3H, s); 2.36 (3H, s); 2.28-2.48 (2H, m); 4.67-4.82 (1H, m); 4.97-5.21 (2H, m); 5.74-5.99 (1H, m); 6.87-7.00 (2H, m); 7.00-7.19 (3H, m); 7.20-7.35 (2H, m) | |
| 91 | 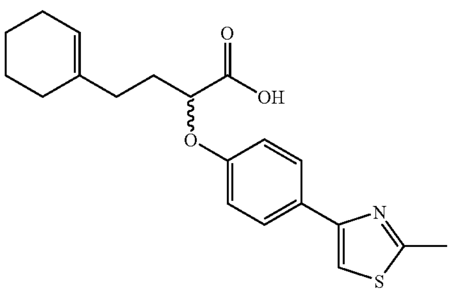 | A | | (CDCl₃): 1.40-1.72 (4H, m); 1.79-2.36 (8H, m); 2.77 (3H, s); 4.51-4.69 (1H, m); 5.32-5.49 (1H, m); 6.84-7.00 (2H, m); 7.13 (1H, s); 7.60-7.80 (2H, m); 8.76 (1H, broad s). | |
| 92 | 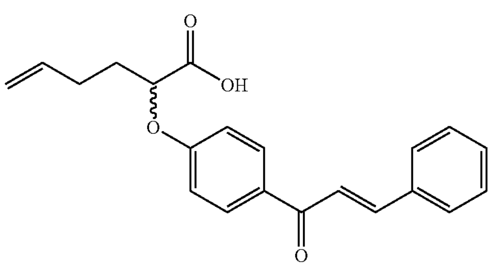 | A | 125° C. | (CDCl₃): 1.81-2.34 (4H, m); 4.48-4.73 (1H, m); 4.78-5.01 (2H, m); 5.48-5.80 (1H, m); 5.94-5.80 (1H, m); 6.34 (1H, broad s); 6.72-8.02 (10H, m). | |
| 93 | 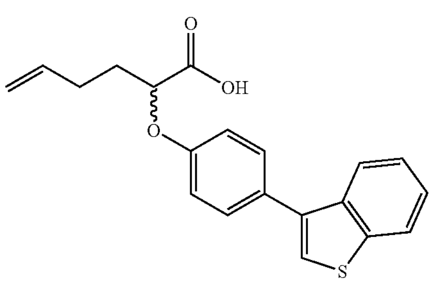 | A | 98° C. | (CDCl₃): 1.91-2.57 (4H, m); 4.64-4.84 (1H, m); 4.94-5.21 (2H, m); 5.72-5.98 (1H, m); 6.83-7.00 (9H, m) | |
| 94 | 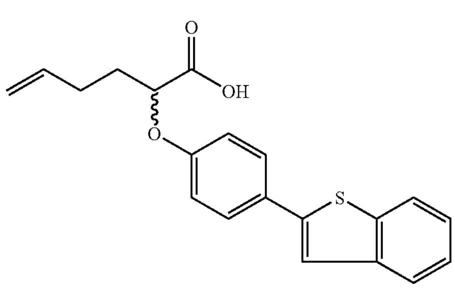 | A | 183° C. | (DMSO-d6): 1.81-2.34 (4H, m); 4.69-4.85 (1H, m); 4.89-5.17 (2H, m); 5.66-6.08 (1H, m); 6.37-7.18 (2H, m); 7.19-8.24 (7H, m); 13.16 (1H, broad s). | |

TABLE 1-continued

| Ex. | STRUCTURE | Method | M.p. (° C.) | NMR | MASS |
|-----|-----------|--------|-------------|-----|------|
| 95 | [structure: 2-((4'-(trifluoromethoxy)biphenyl-4-yl)oxy)hex-5-enoic acid] | A | 115°-116° C. | (DMSO-d6): 1.84-2.34 (4H, m); 4.66-4.87 (1H, m); 4.93-5.17 (2H, m); 5.66-6.08 (1H, m); 6.77-7.18 (2H, m); 7.18-8.23 (6H, m); 13.16 (1H, broad s). | |
| 97 | [structure: 2-((3'-fluorobiphenyl-4-yl)oxy)hex-5-enoic acid] | A | 110° C. | (CDCl$_3$): 1.97-2.46 (4H, m); 4.64-4.80 (1H, m); 4.94-5.18 (2H, m); 5.67-5.97 (1H, m); 6.82-7.07 (3H, m); 7.12-7.59 (5H, m); 6-9 ppm broad complex multiplet, OH. | |
| 98 | [structure: 2-((3',4'-difluorobiphenyl-4-yl)oxy)hex-5-enoic acid] | A | 70°-72° C. | (CDCl$_3$): 1.90-2.51 (4H, m); 4.59-4.82 (1H, m); 4.90-5.19 (2H, m); 5.65-5.97 (1H, m); 6.82-7.05 (2H, m); 7.07-7.57 (5H, m); 6-8 ppm broad complex multiplet, OH. | |

Results

The activity of the compounds of the invention leading to a hypolipidaemiant and hypoglycaemiant effect was demonstrated in vitro and in vivo by performing the following tests:

The measurement of the PPAR activation was performed according to a technique described by Lehmann et al. (*J. Biol. Chem.*, 270, (1995), 12953-12956).

CV-1 cells (monkey kidney cells) are co-transfected with an expression vector for the chimeric proteins PPARα-Gal4 or PPARγ-Gal4 and with a "reporter" plasmid that allows the expression of the luciferase gene placed under the control of a promoter comprising Gal4 response elements.

The cells are plated into 96-well microplates and co-transfected using a commercial reagent with the reporter plasmid (pG5-tk-pGL3) and the expression vector for the chimeric protein (PPARα-Gal4 or PPARγ-Gal4). After incubating for 4 hours, whole culture medium (comprising 10% foetal calf serum) is added to the wells. After 24 hours, the medium is removed and replaced with whole medium comprising the test products (50 μM, 25 μM and 12.5 μM final). The products are left in contact with the cells for 18 hours. The cells are then lysed and the luciferase activity is measured using a luminometer. A PPAR activation factor can then be calculated by means of activation of the expression of the reporter gene induced by the product (relative to the control cells that have not received any product).

By way of example, the compound of Example 2 at a concentration of 50 μM, activates the chimeric protein PPARα-Gal-4 by a factor of 24.9, and the chimeric protein PPARγ-Gal4 by a factor of 9.3, relative to the activity of the receptor without ligand. In the absence of the binding domain for the PPAR α or γ ligand (vector expressing Gal4 alone), the luciferase activity measured in the presence of this product is zero.

The following results were obtained with concentrations of 50 μM, 25 μM and 12.5 μM on the chimers α and γ.

| Ex. | Concentration | Chimer α | Chimer γ |
|-----|---------------|----------|----------|
| 2 | 50 μM | 24.9 | 9.3 |
|   | 25 μM | 17.2 | 5.2 |
|   | 12.5 μM | 3.6 | 2.2 |
| 12 | 50 μM | 19.9 | 15.6 |
|   | 25 μM | 13.1 | 3.4 |
|   | 12.5 μM | 4.3 | 1 |
| 13 | 50 μM | 12.5 | 8.5 |
|   | 25 μM | 4.8 | 5.3 |
|   | 12.5 μM | 6 | 7.2 |
| No product | — | 1 | 1 |

The antidiabetic and hypolipidaemiant activity of the compounds was determined orally on db/db mice 17-week-old db/db mice are treated orally for 15 days with the compound of Example 2 (100 mg/kg/day). Each group studied comprises seven animals. After treatment for 15 days, retro-orbital samples are taken under mild anaesthesia and after fasting for four hours.

The following parameters were measured:

Assay of the glycaemia (glucose oxidase) and of the lipid parameters on the sera at D15 (COBAS): triglycerides, total cholesterol (CHOL), HDL cholesterol (HDL-C) and free fatty acids (FFA) (BioMérieux and Waco Chemicals assay kit).

The results obtained are given in the table below. The measurements reported represent mean values±standard error.

|  | Control | Example 2 | % var. |
|---|---|---|---|
| Glycaemia (mM) | 31.60 ± 5.93 | 23.23 ± 5.43 | −26% * |
| Triglycerides (mM) | 2.32 ± 1.14 | 1.05 ± 0.29 | −55% * |
| HDL-C (mM) | 3.50 ± 0.70 | 4.26 ± 0.61 | +21% * |
| CHOL (mM) | 4.74 ± 1.27 | 6.04 ± 0.61 | +28% ns |
| FFA (mM) | 0.74 ± 0.11 | 0.48 ± 0.12 | −34% ** |

% var.: percentage of variation versus control.
Mann-Whitney test:
* $p < 0.05$ versus control
** $p < 0.01$ versus control
ns: not significant These results demonstrate the antidiabetic and hypolipidaemiant activity of the compounds of the invention on triglycerides and free fatty acids. The marked increase in the level of HDL cholesterol with these same compounds should be noted.

The invention claimed is:

1. A compound, which is
ethyl 2-[(4-trifluoromethylphenyl)oxy]-4-cyclohex-1-en-1-ylbutanoate
4-cyclohex-1-enyl-2[4-(trifluoromethyl)phenoxy]butanoic acid
ethyl 2-[4-(5-chlorothiophen-2-yl)-phenoxy]-4-cyclohex-1-enylbutanoate
2-[4-(5-chlorothiophen-2-yl)phenoxy]-4-cyclohex-1-enylbutanoic acid
methyl 4-cyclohex-1-en-1-yl-2-[(4'-methoxy-1,1'-biphenyl-4-yl)oxy]butanoate
4-cyclohex-1-enyl-2-(4'-methoxy-1,1'-biphenyl-4-yloxy)butanoic acid
4-cyclohex-1-enyl-2-[4-(2-methoxycarbonylvinyl)phenoxy]butanoic acid

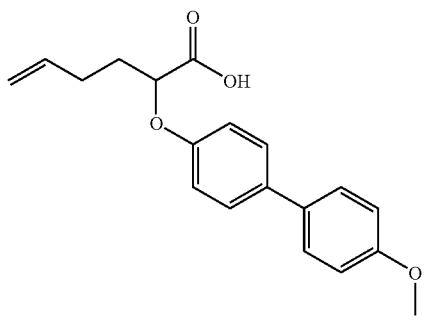

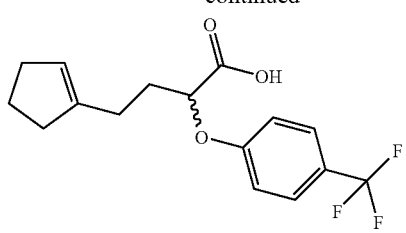

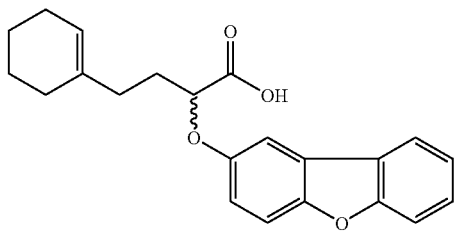

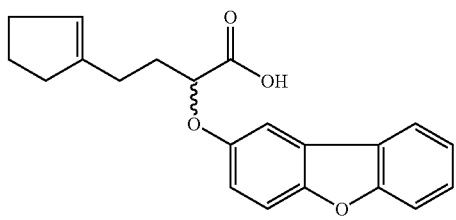

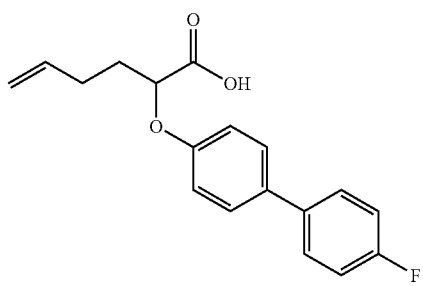

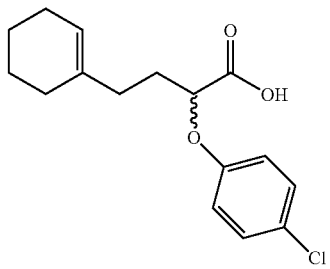

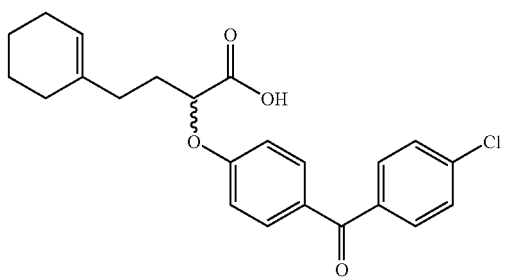

61
-continued
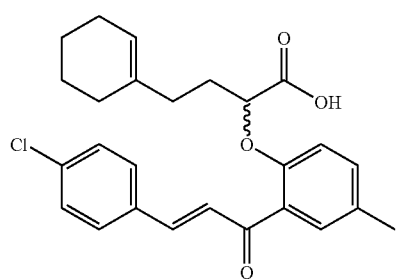
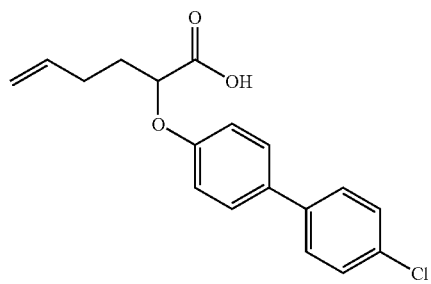
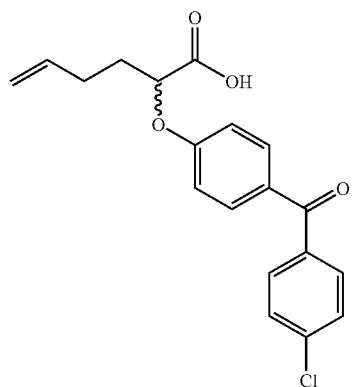
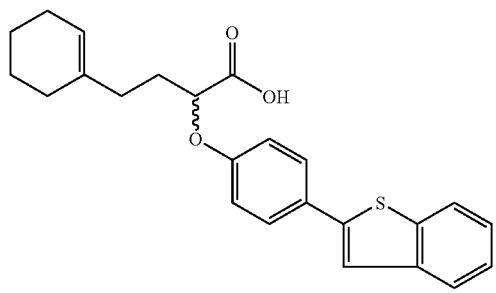
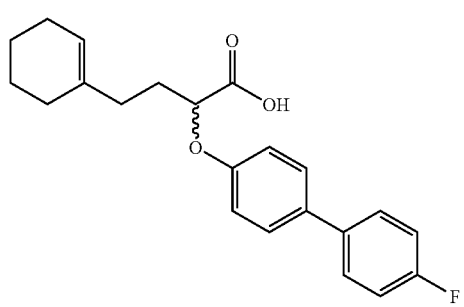
62
-continued
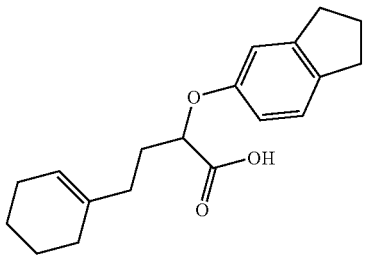
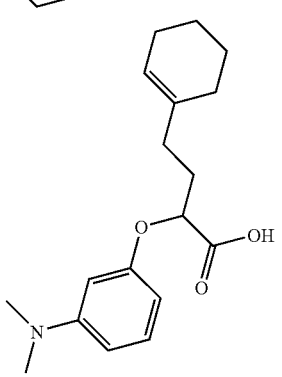
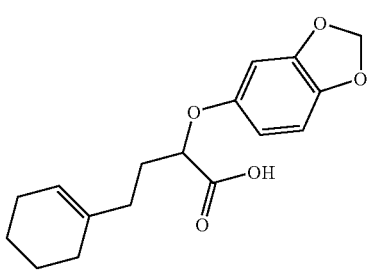
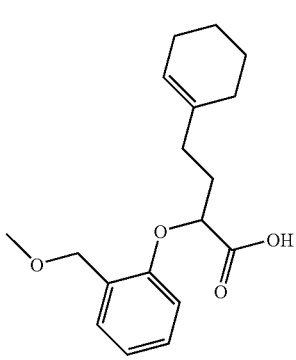
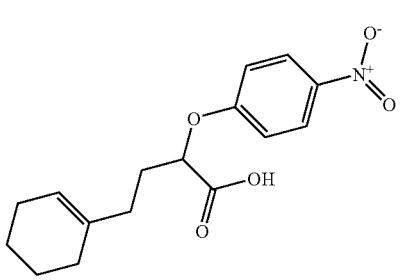

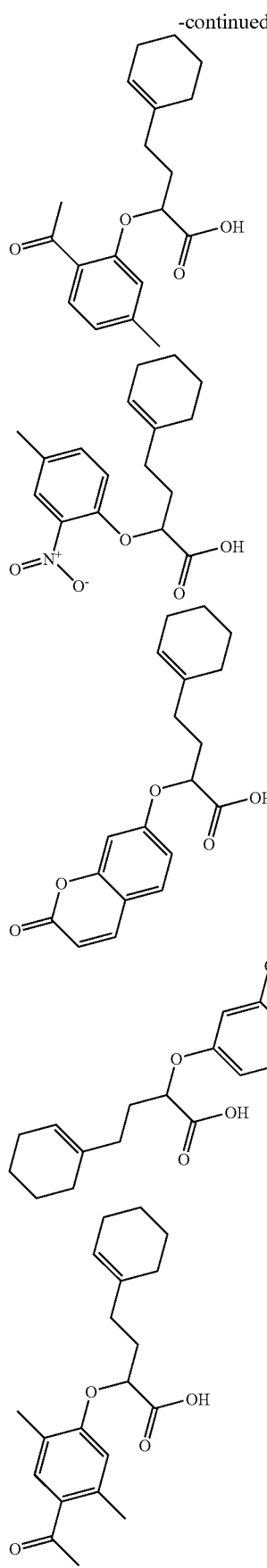
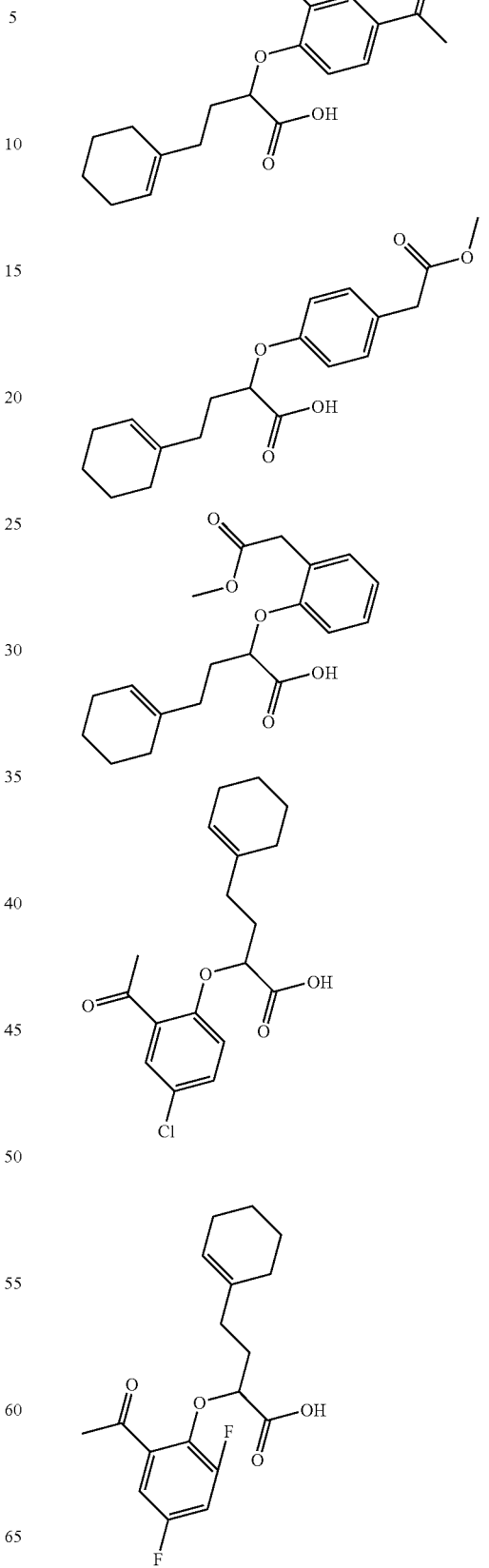

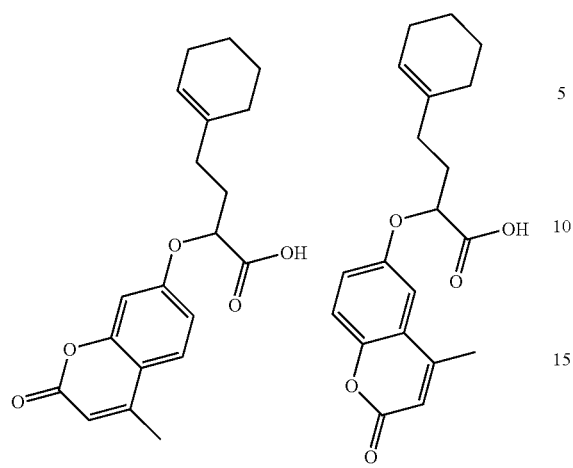
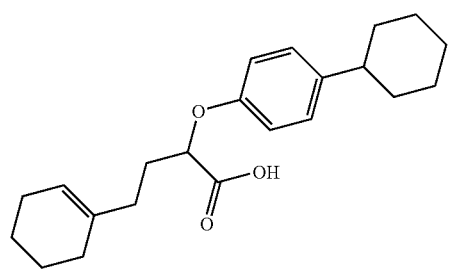
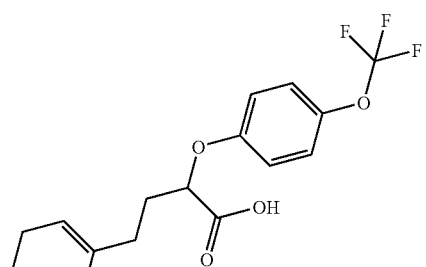
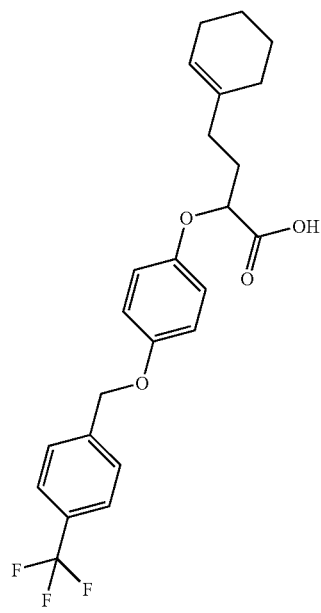
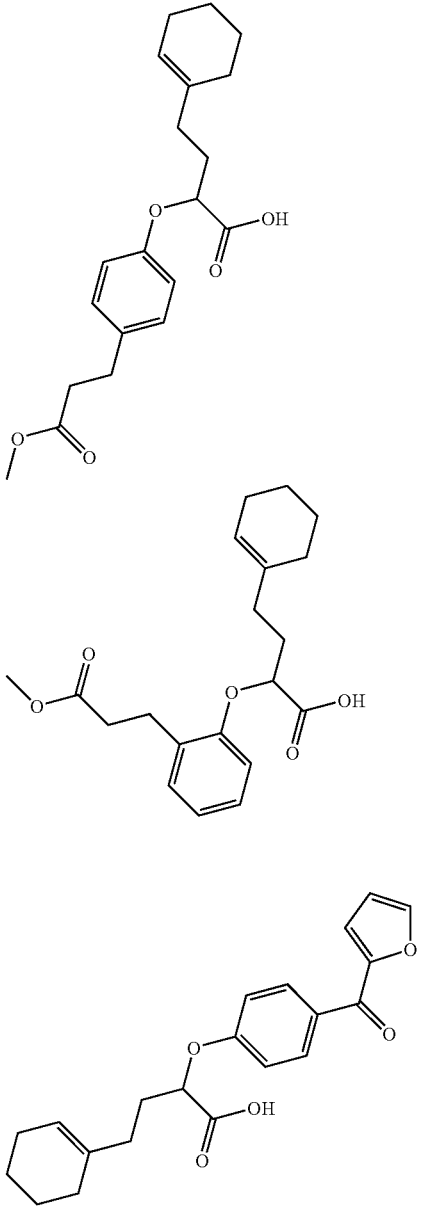
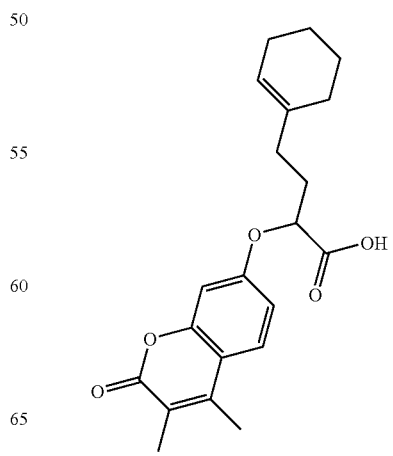
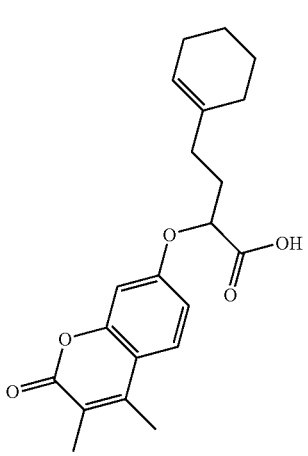

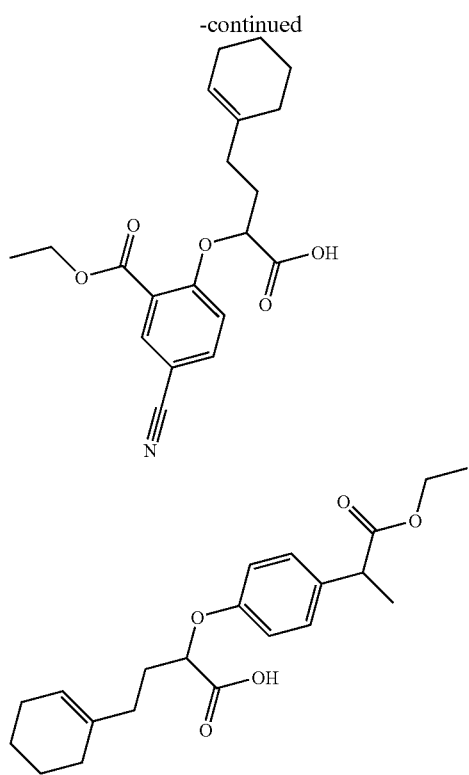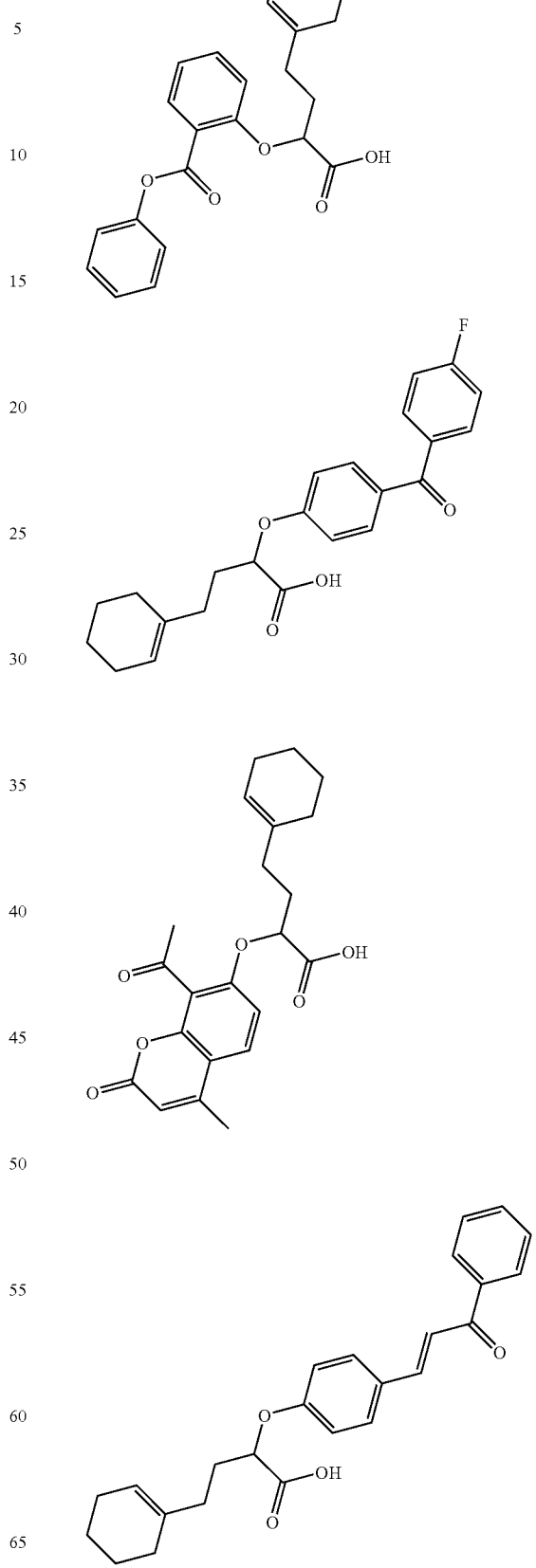

-continued
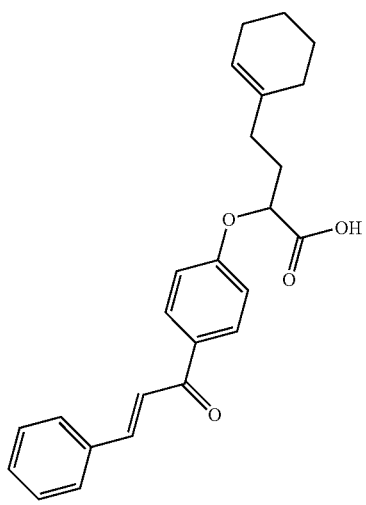
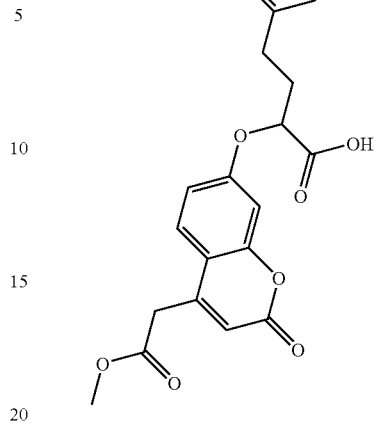
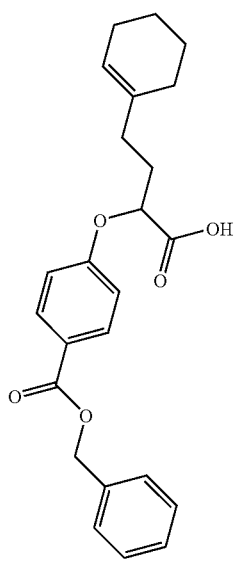
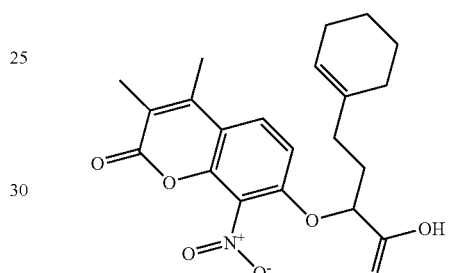
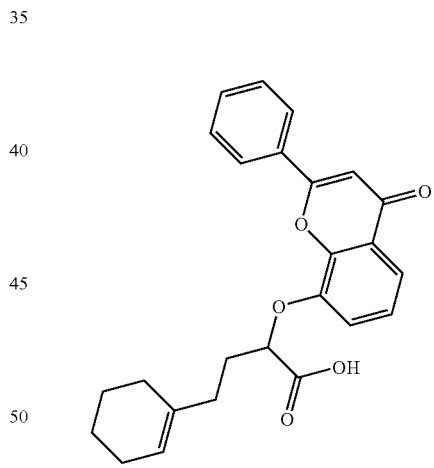
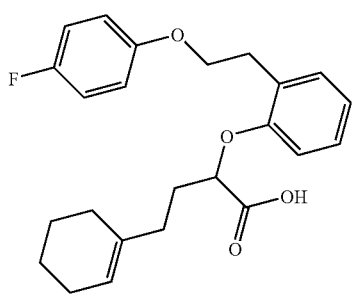
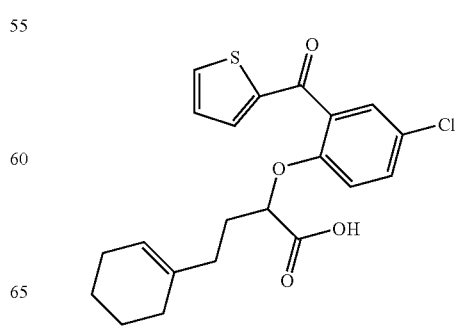

71
-continued
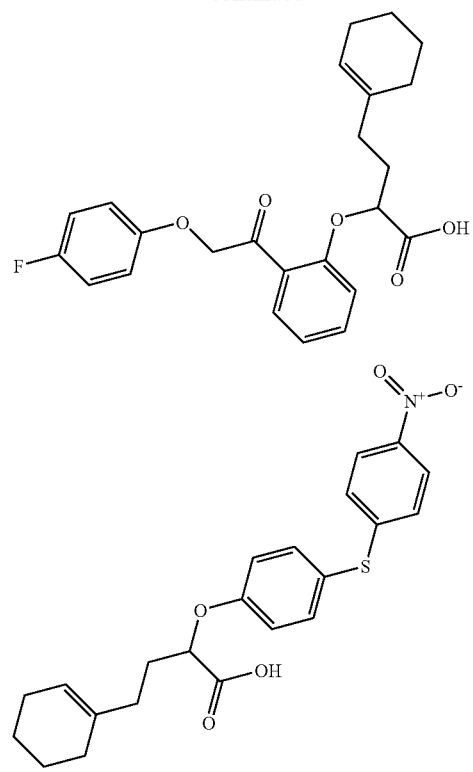
72
-continued
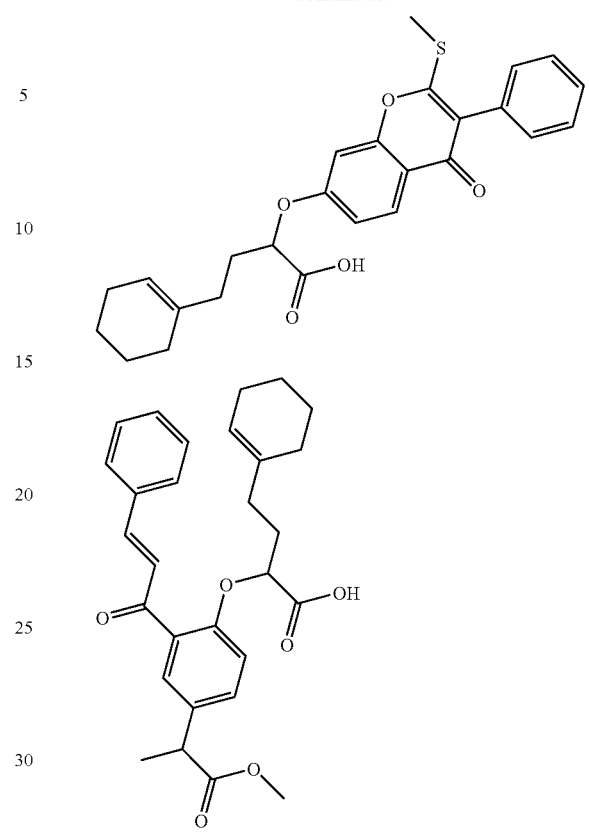
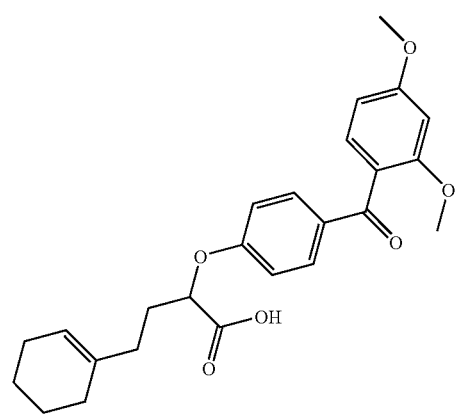
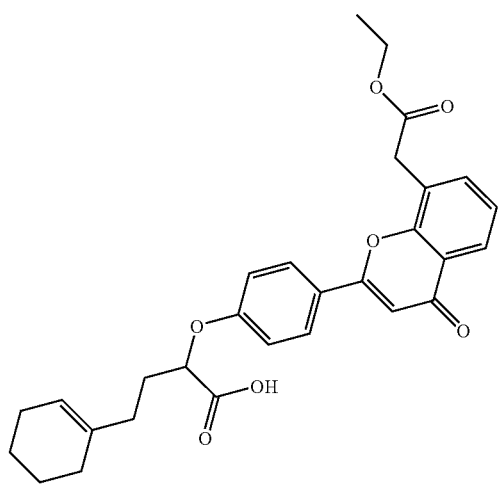
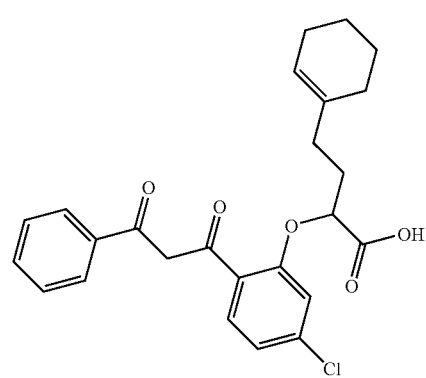

73
-continued
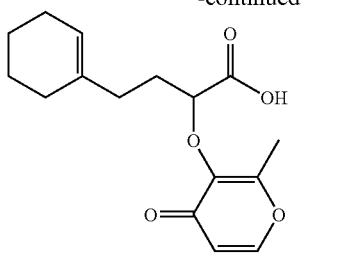
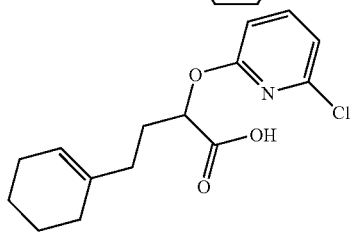
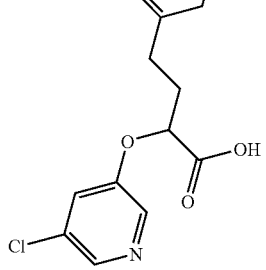
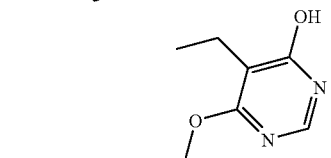
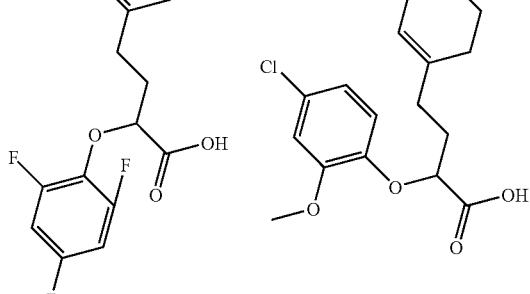
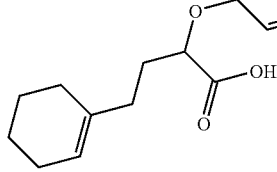
74
-continued
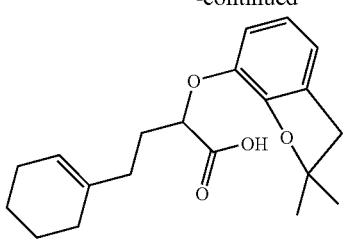
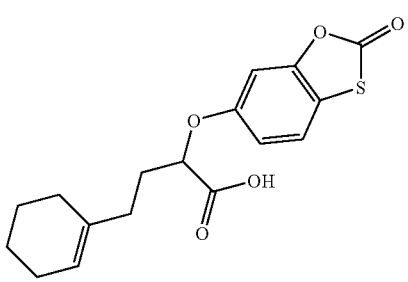
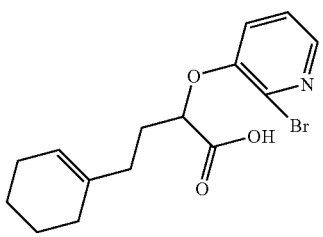
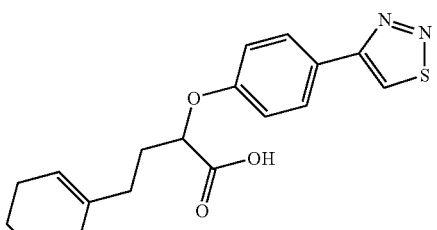
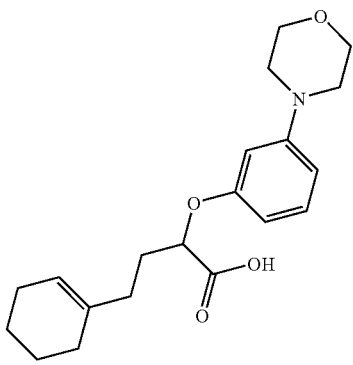

75
-continued
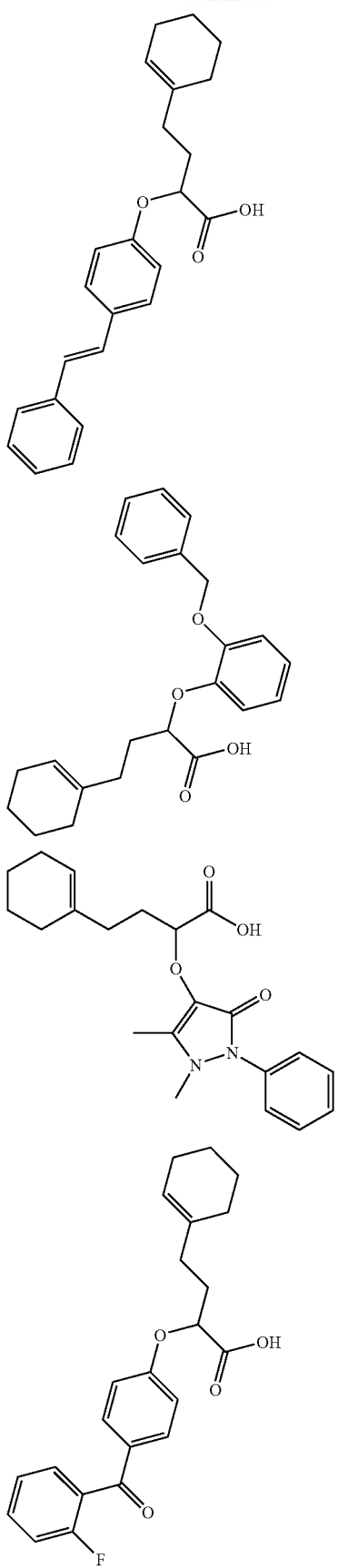
76
-continued
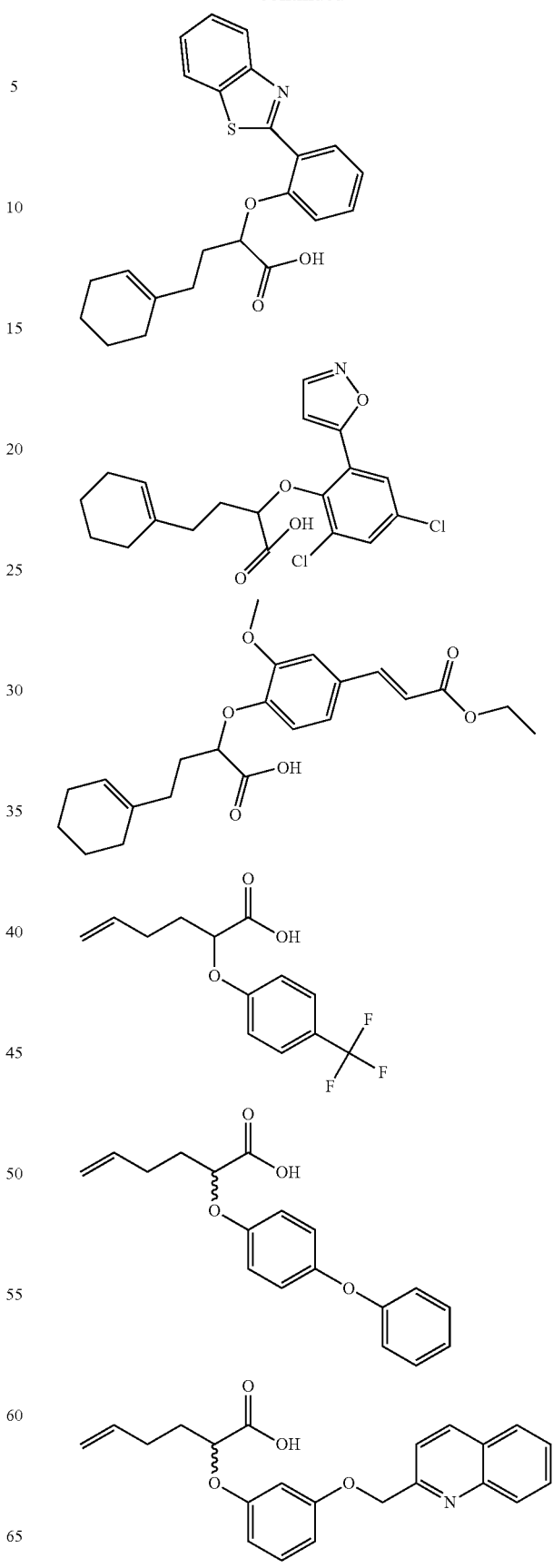

-continued

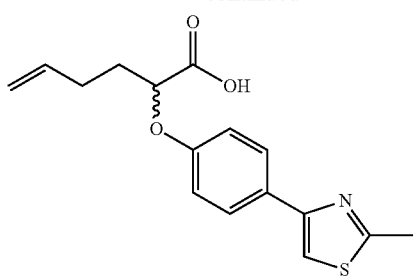

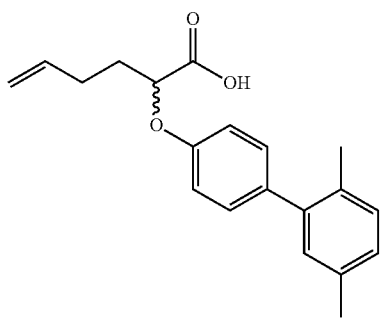

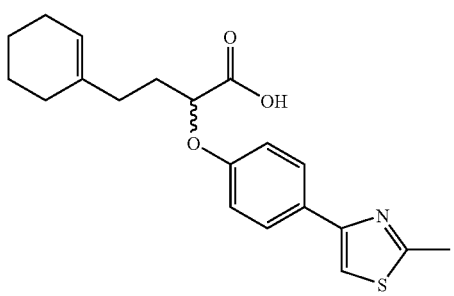

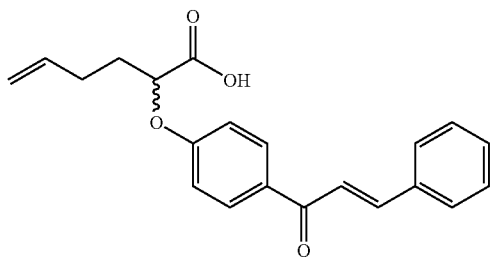

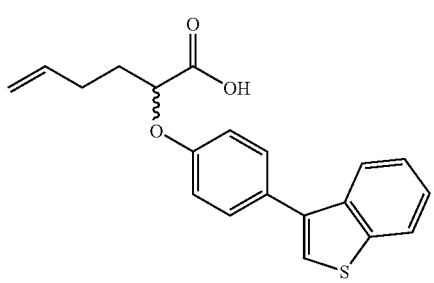

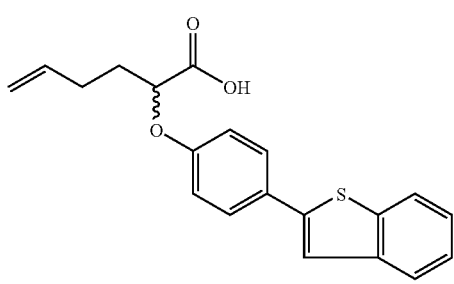

-continued

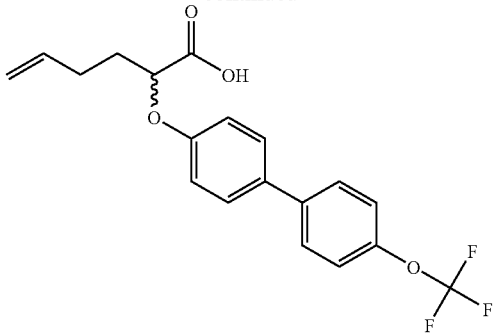

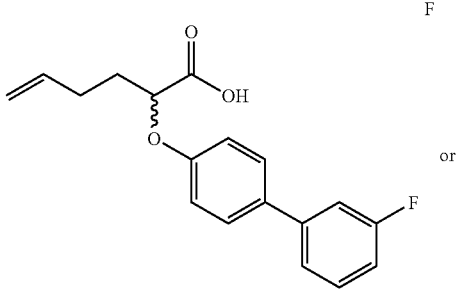

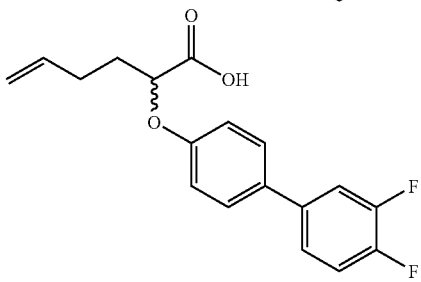

or a pharmaceutically acceptable salt thereof.

2. A compound according to claim 1, which is
ethyl 2-[(4-trifluoromethylphenyl)oxy]-4-cyclohex-1-en-1-ylbutanoate
4-cyclohex-1-enyl-2-[4-(trifluoromethyl)phenoxy]butanoic acid
ethyl 2-[4-(5-chlorothiophen-2-yl)-phenoxy]-4-cyclohex-1-enylbutanoate
2-[4-(5-chlorothiophen-2-yl)phenoxy]-4-cyclohex-1-enylbutanoic acid
methyl 4-cyclohex-1-en-1-yl-2-[(4'-methoxy-1,1'-biphenyl-4-yl)oxy]butanoate
4-cyclohex-1-enyl-2-(4'-methoxy-1,1'-biphenyl-4-yloxy)butanoic acid
4-cyclohex-1-enyl-2-[4-(2-methoxycarbonylvinyl)phenoxy]butanoic acid

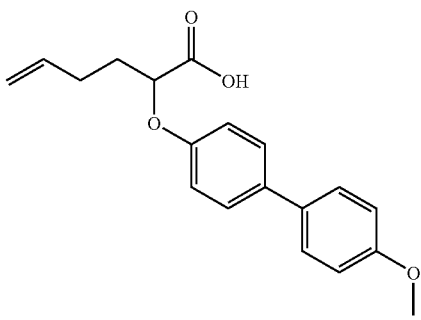

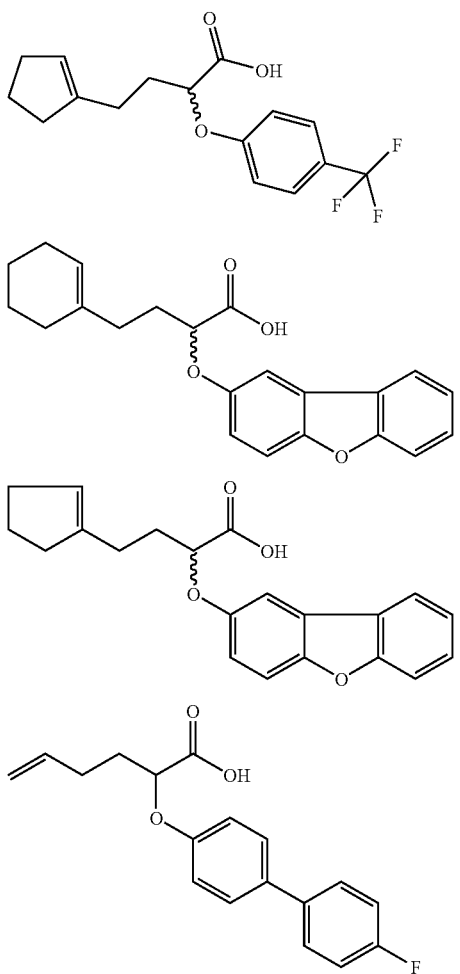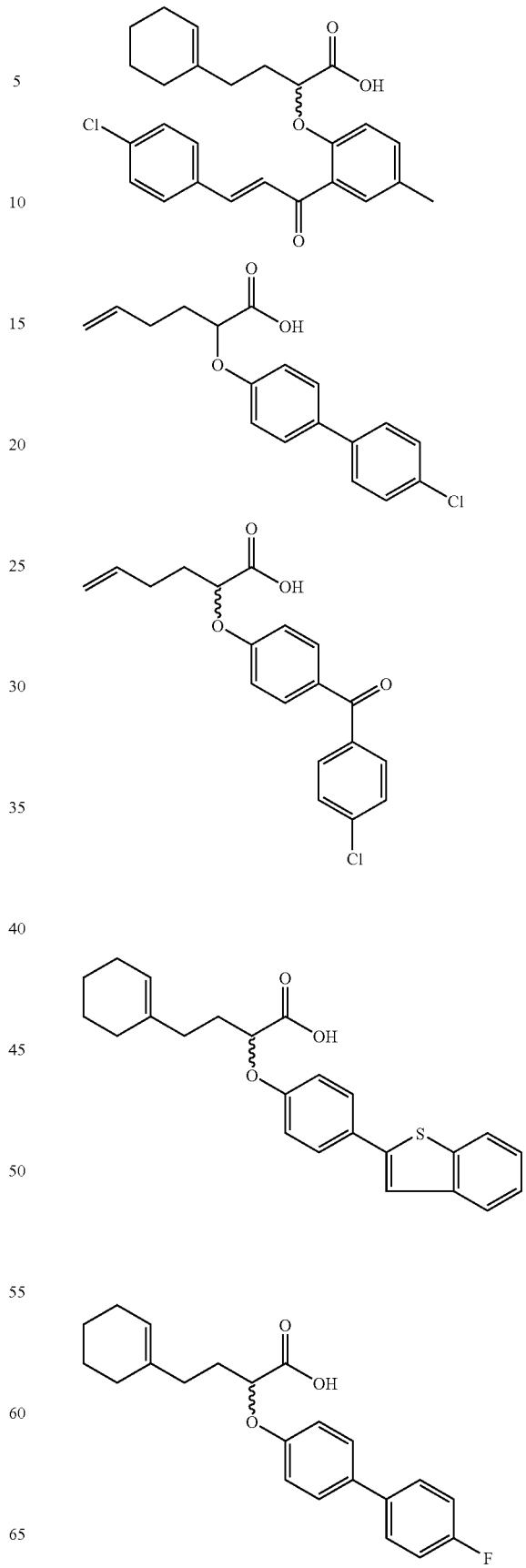

81
-continued
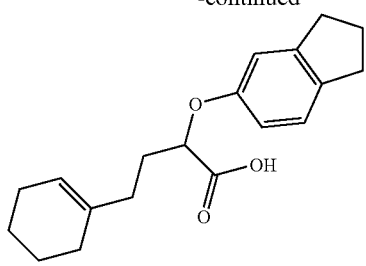
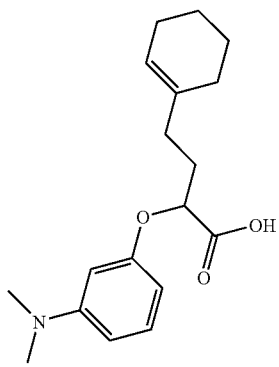
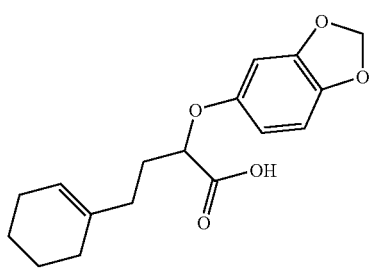
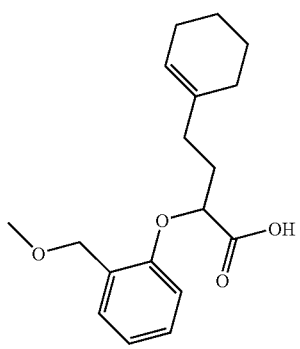
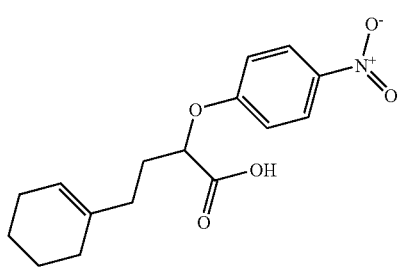
82
-continued
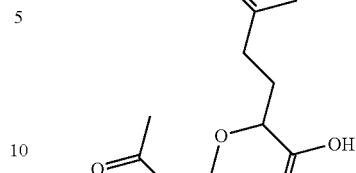
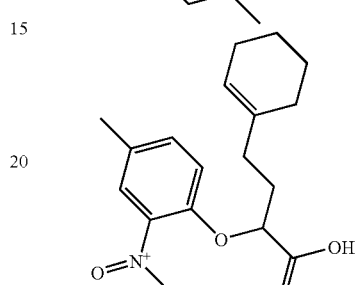
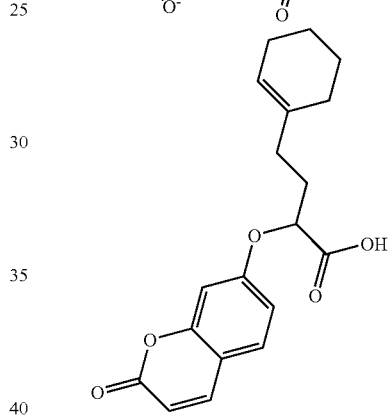
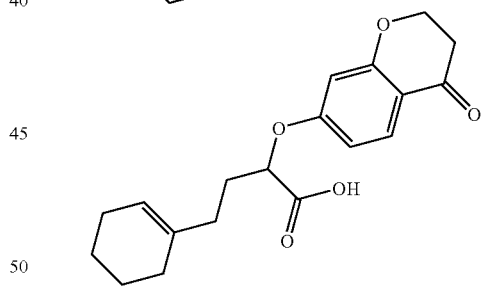
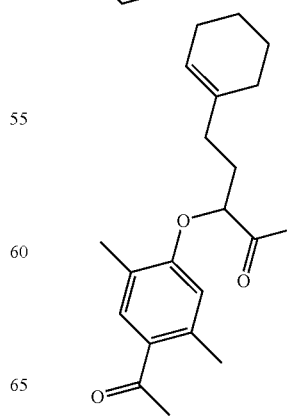

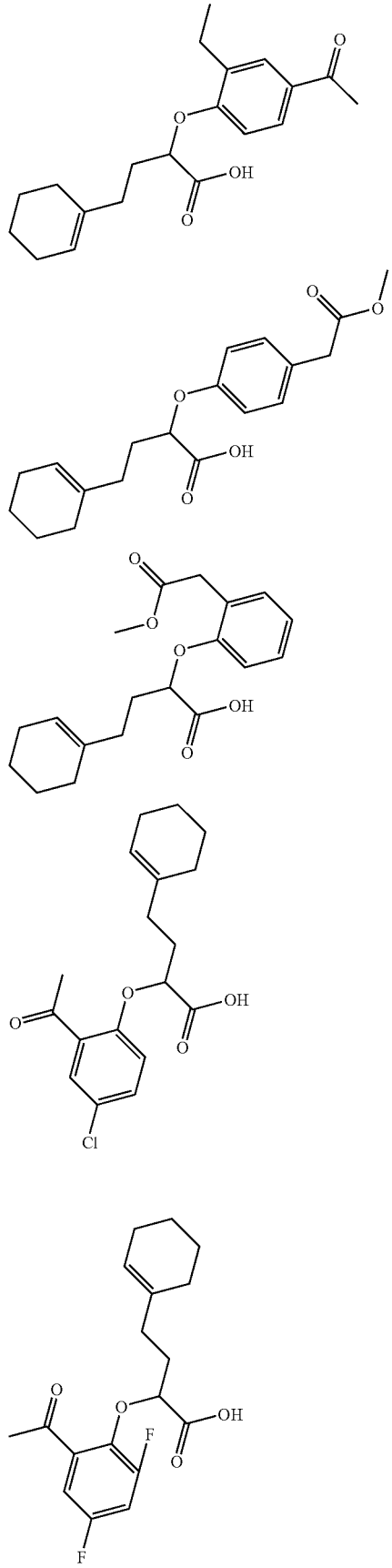
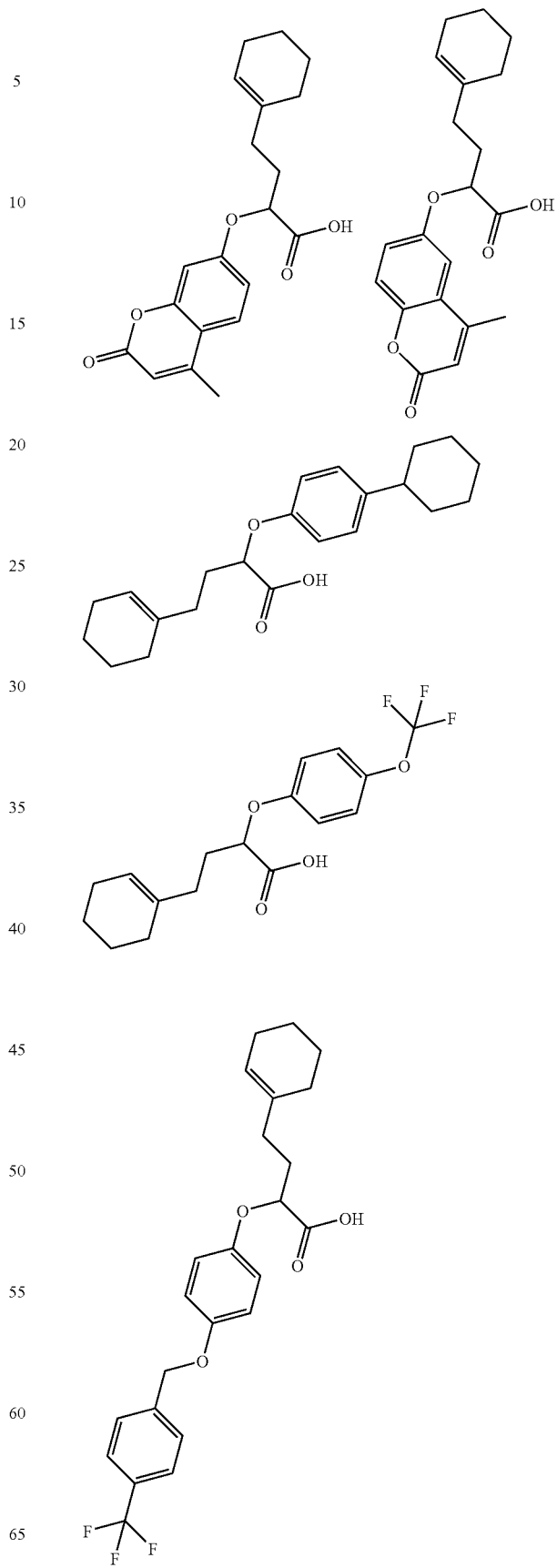

85
-continued
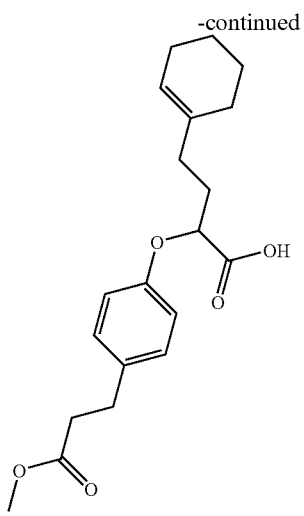
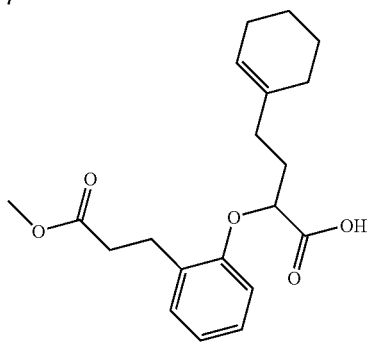
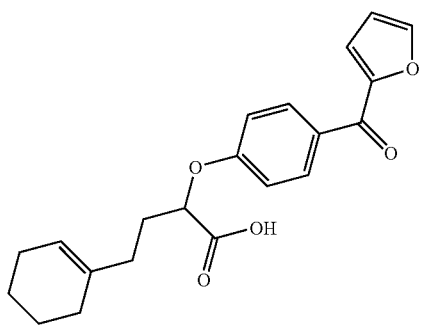
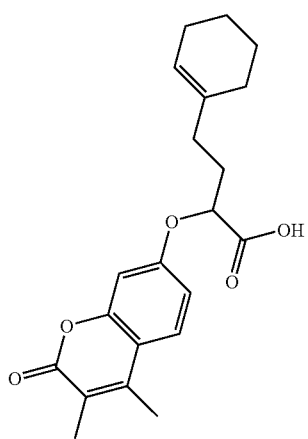
86
-continued
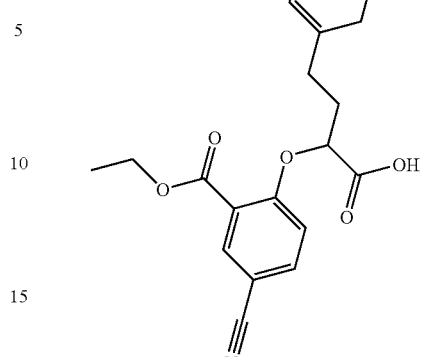
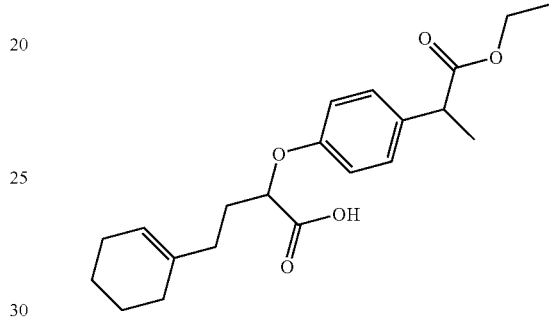
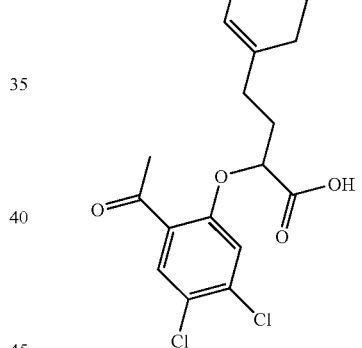
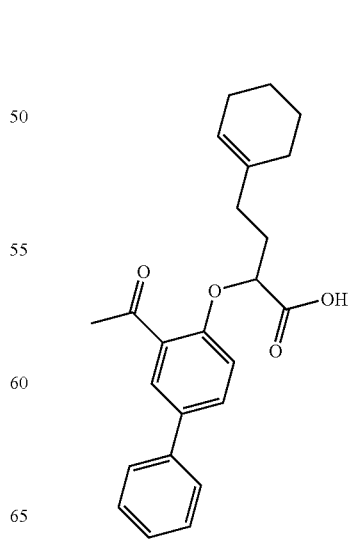

87
-continued
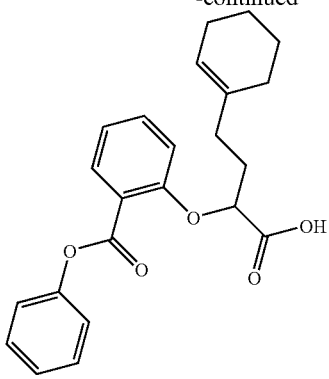
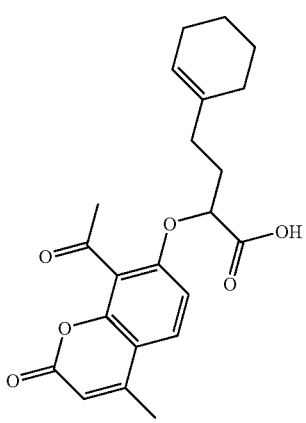
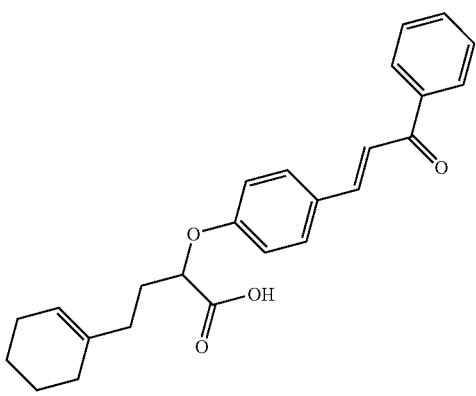
88
-continued
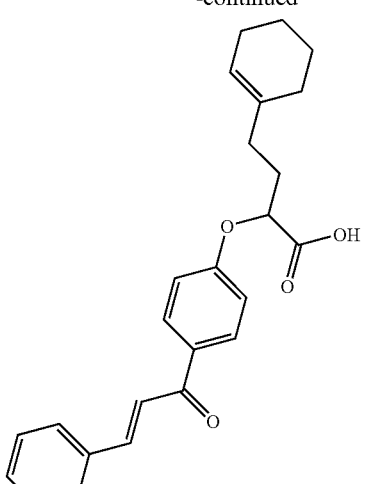
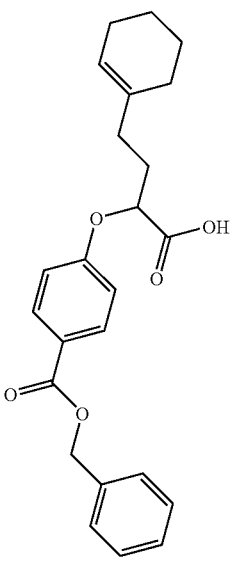
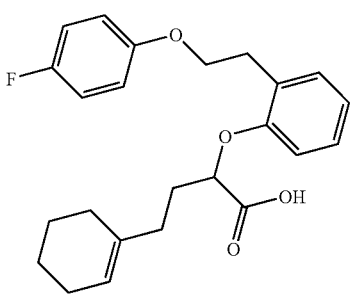

89
-continued
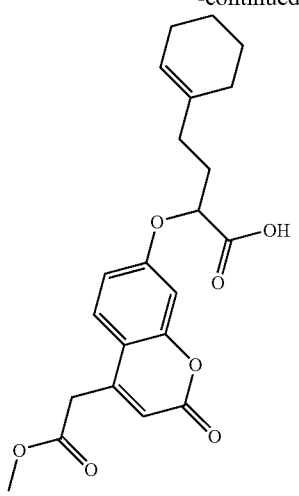
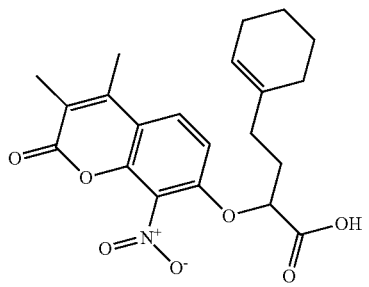
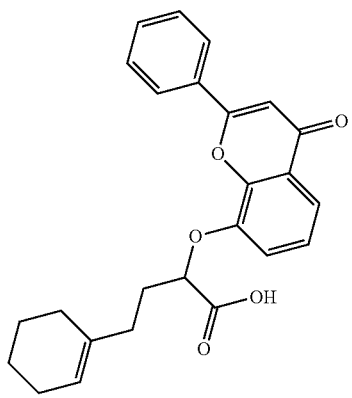
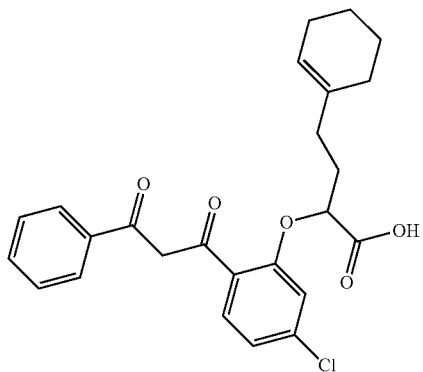
90
-continued
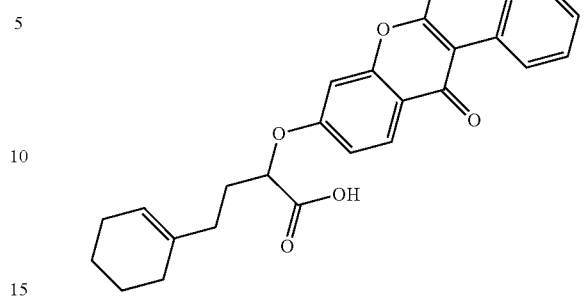
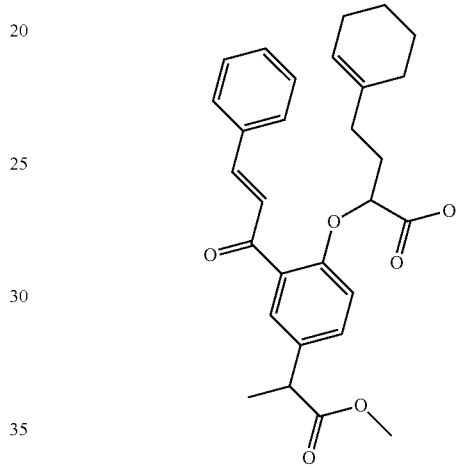
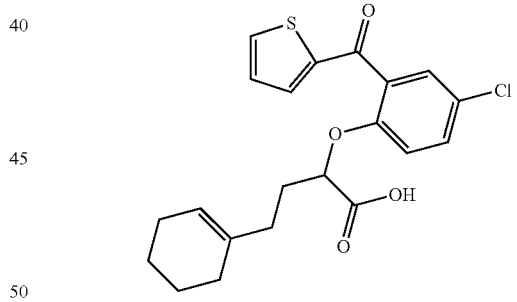
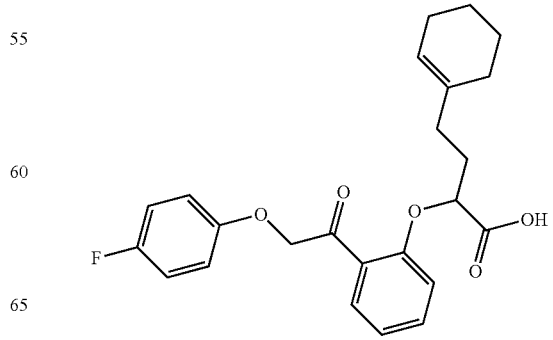

91
-continued
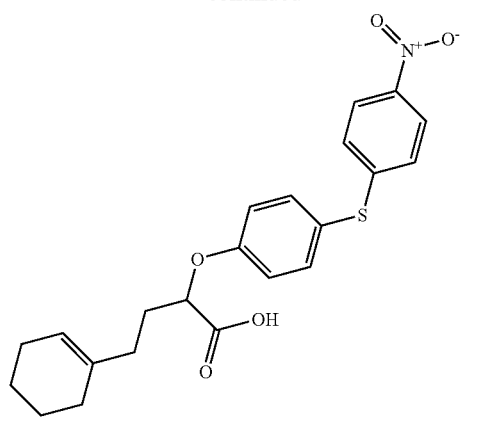
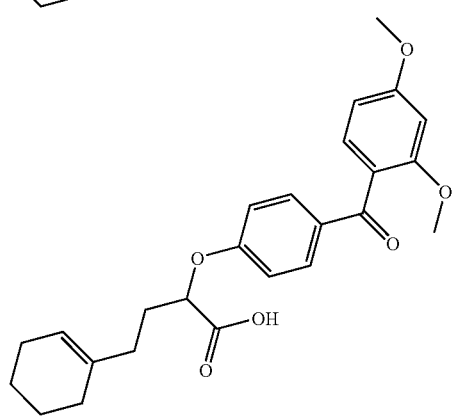
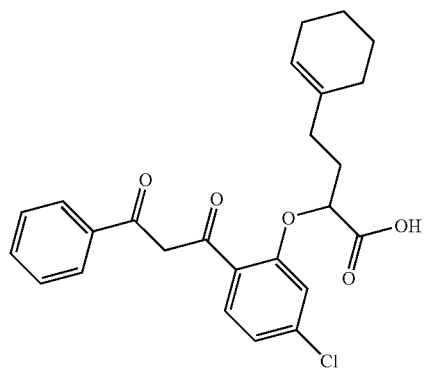
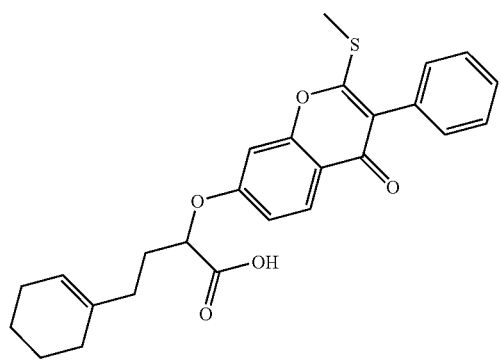
92
-continued
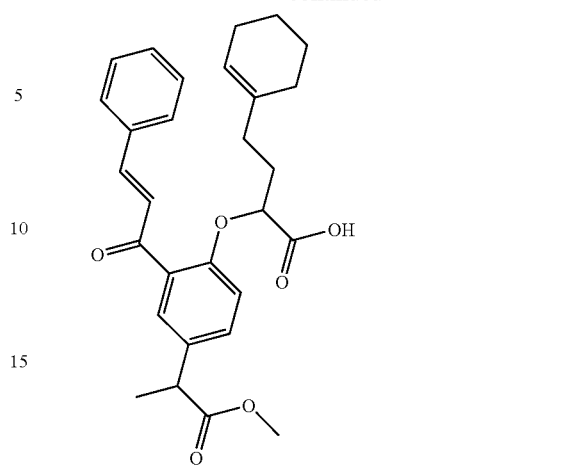
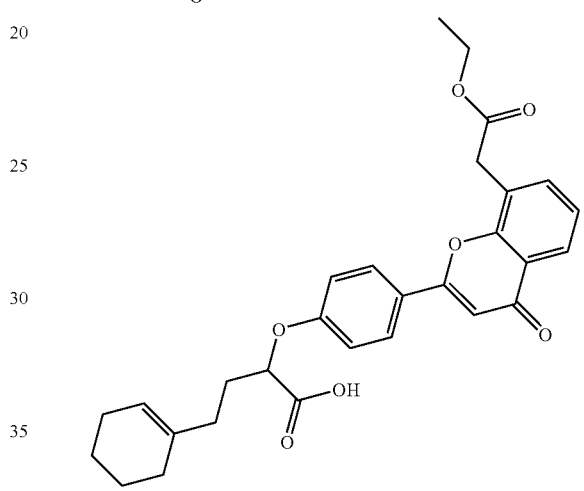
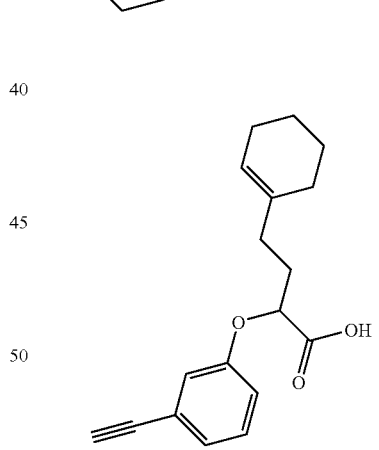
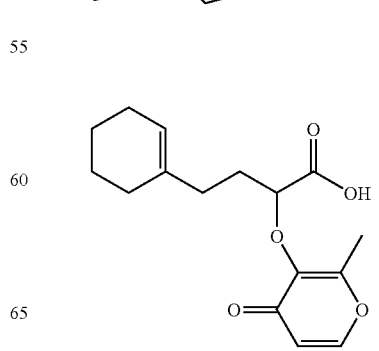

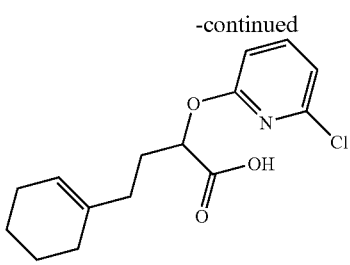
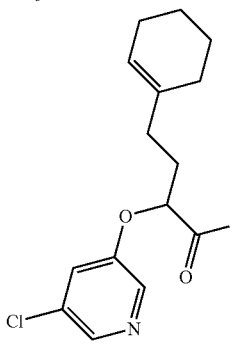
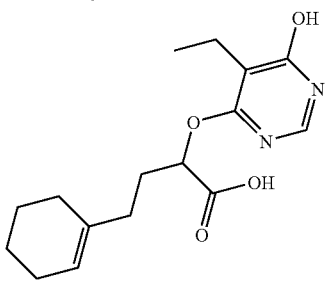
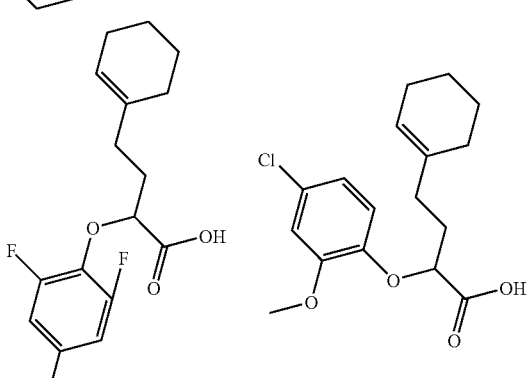
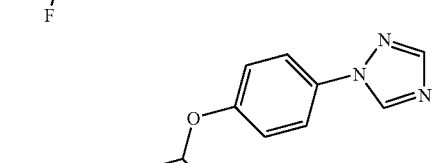
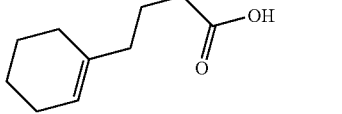
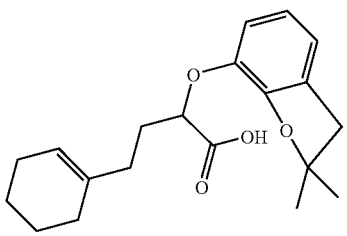
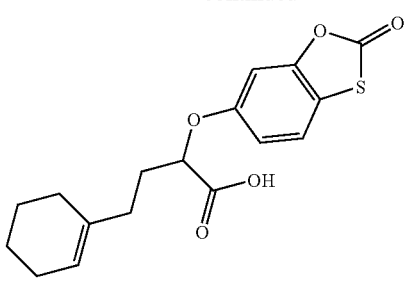
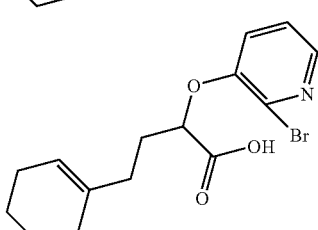
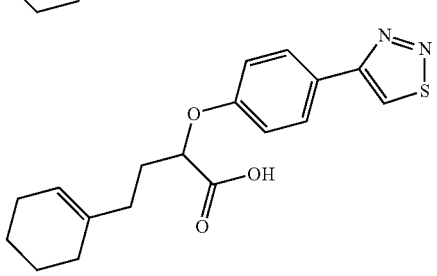
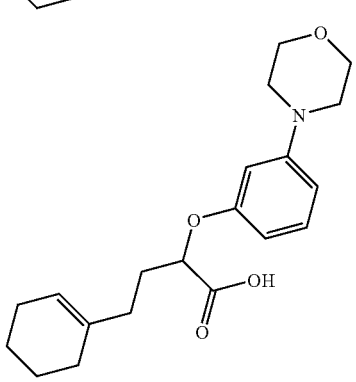
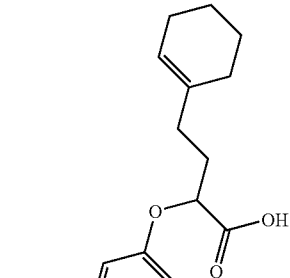
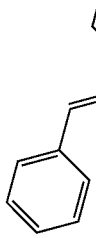

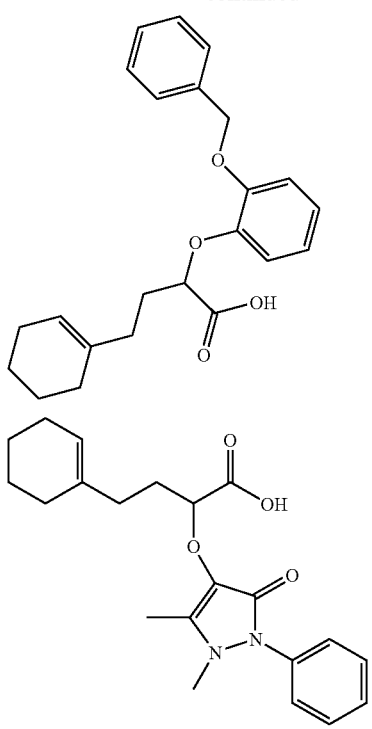
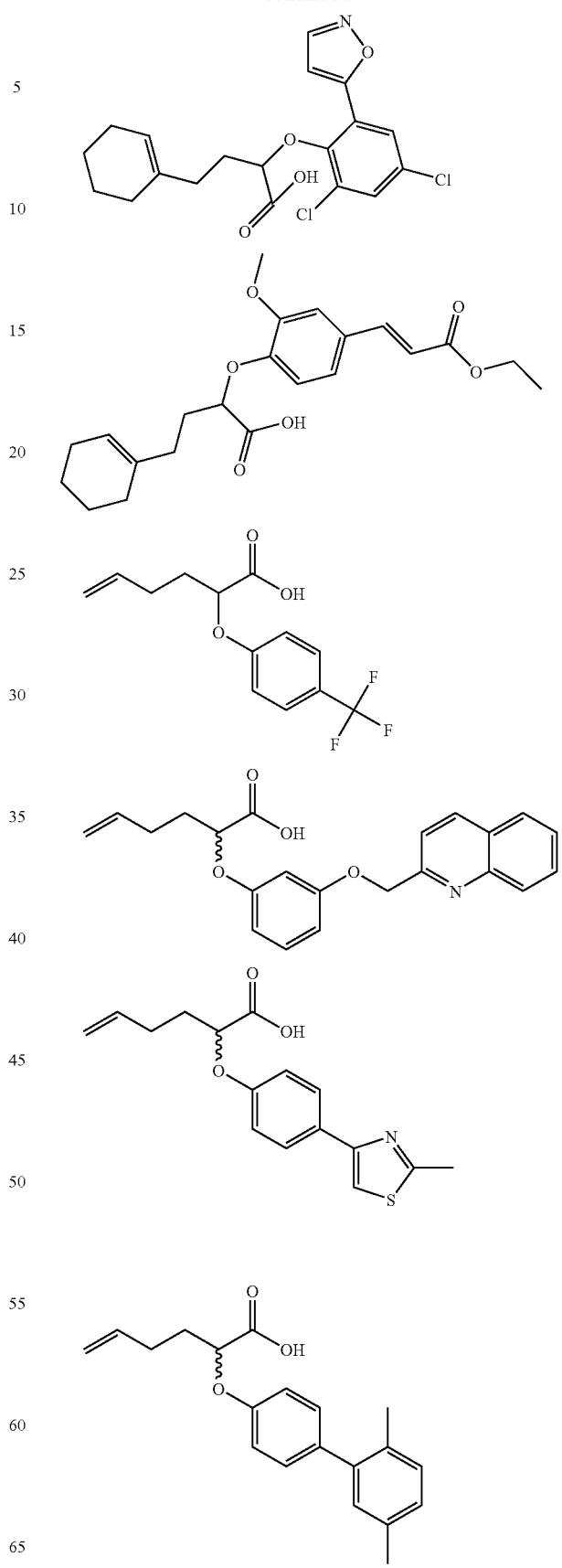

-continued
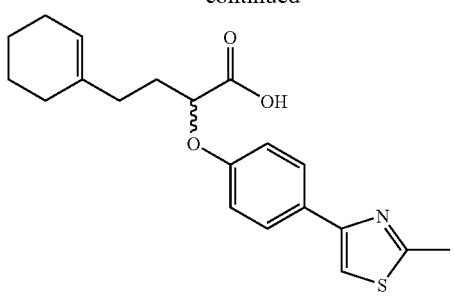
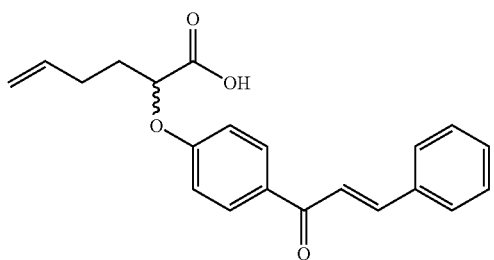
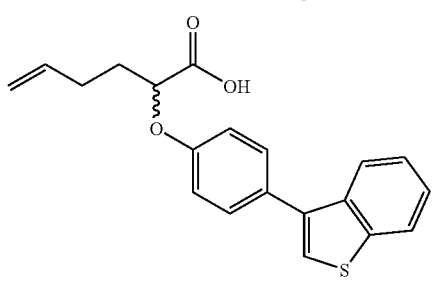
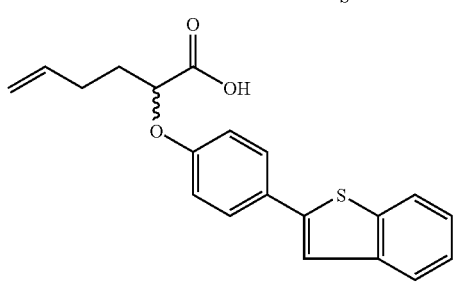
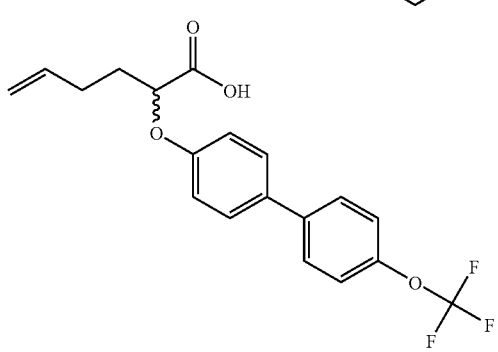
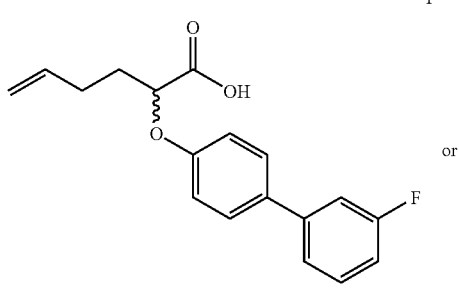
or
-continued
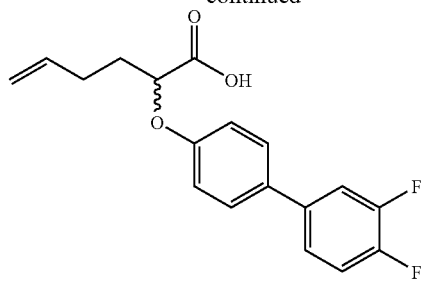
or a pharmaceutically acceptable salt thereof.
3. A compound according to claim 1, which is
methyl 4-cyclohex-1-en-1-yl-2-[(4'-methoxy-1,1'-biphenyl-4-yl)oxy]butanoate
4-cyclohex-1-enyl-2-(4'-methoxy-1,1'-biphenyl-4-yloxy)butanoic acid
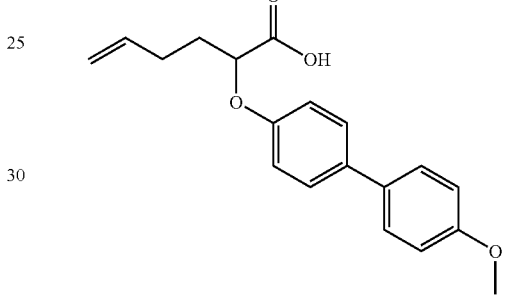
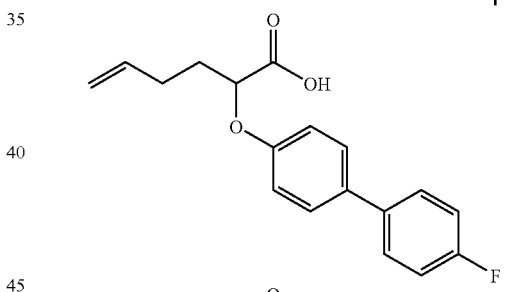
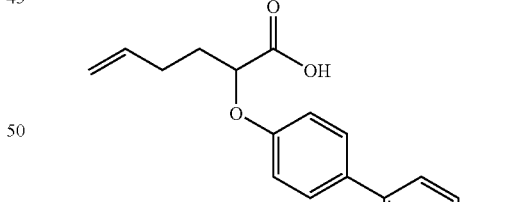
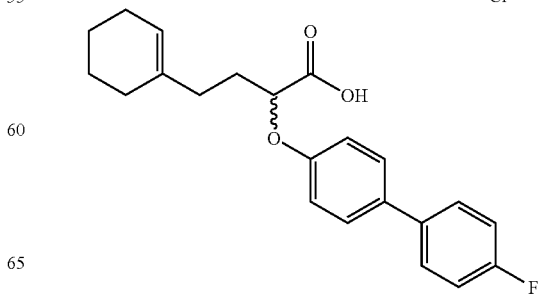

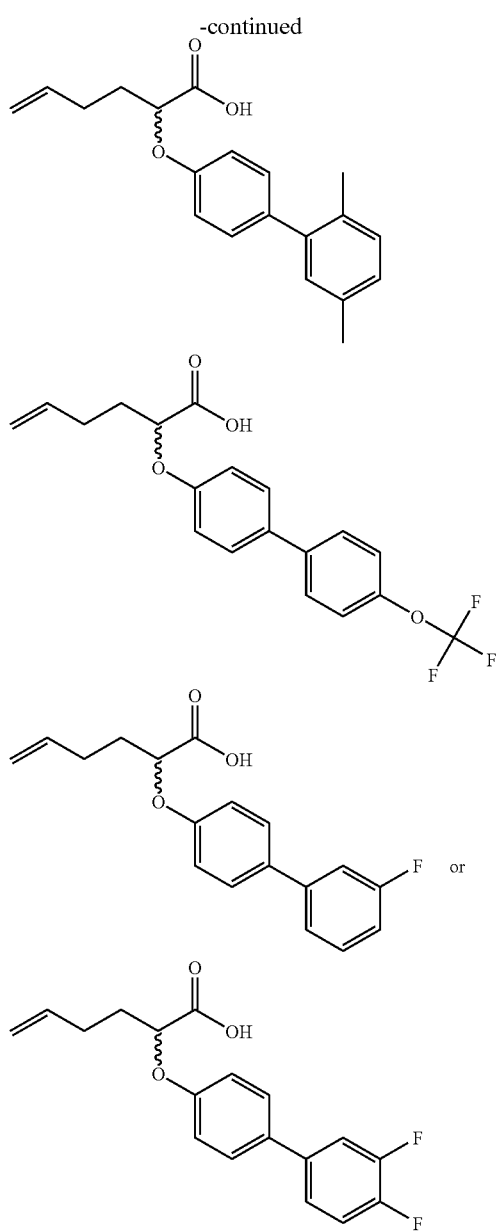

or a pharmaceutically acceptable salt thereof.

4. A compound according to claim 1, which is ethyl 2-[(4-trifluoromethylphenyl)oxy]-4-cyclohex-1-en-1-ylbutanoate 4-cyclohex-1-enyl-2-[4-(trifluoromethyl)phenoxy]butanoic acid ethyl 2-[4-(5-chlorothiophen-2-yl)-phenoxy]-4-cyclohex-1-enylbutanoate 2-[4-(5-chlorothiophen-2-yl)phenoxy]-4-cyclohex-1-enylbutanoic acid methyl 4-cyclohex-1-en-1-yl-2-[(4'-methoxy-1,1'-biphenyl-4-yl)oxy]butanoate 4-cyclohex-1-enyl-2-(4'-methoxy-1,1'-biphenyl-4-yloxy)butanoic acid 4-cyclohex-1-enyl-2-[4-(2-methoxycarbonylvinyl)phenoxy]butanoic acid

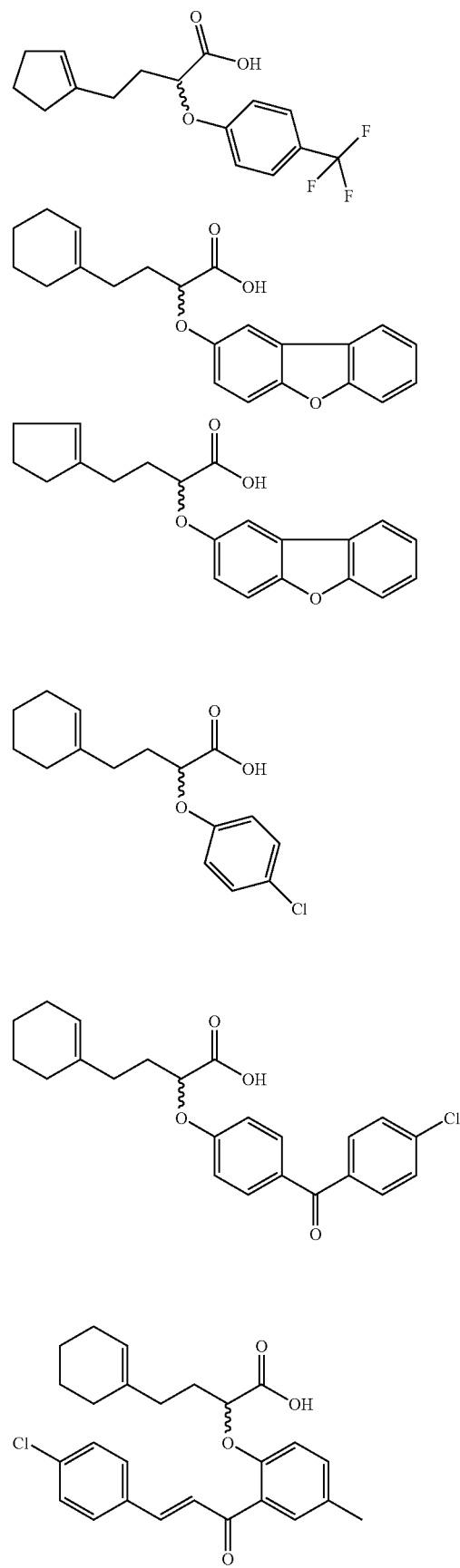

101
-continued
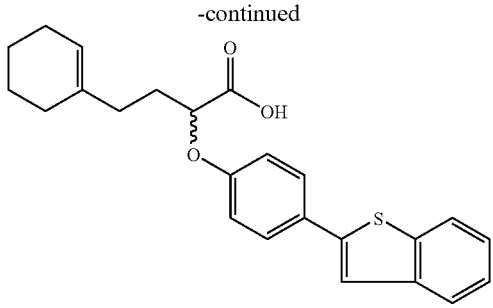
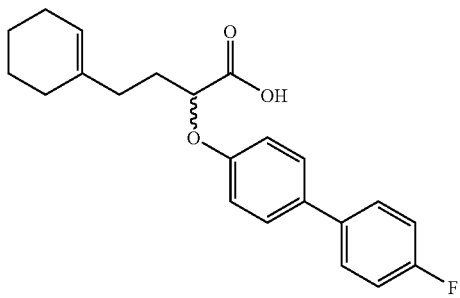
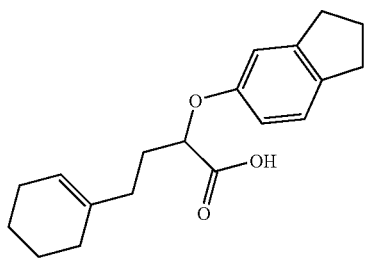
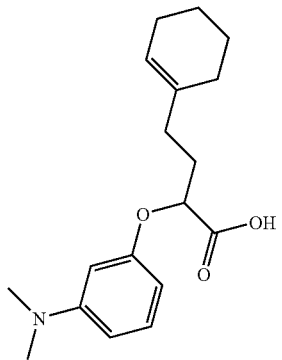
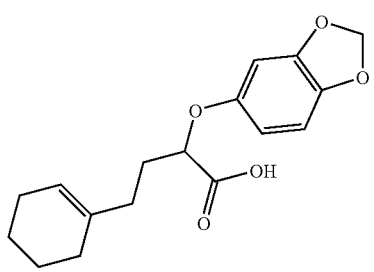
102
-continued
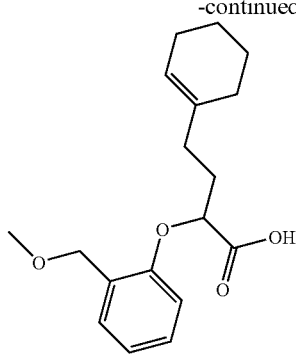
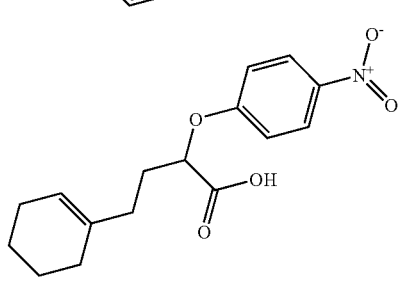
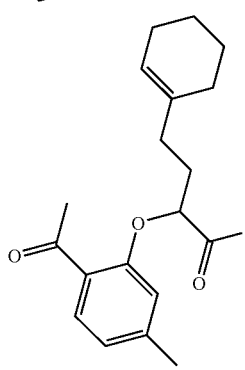
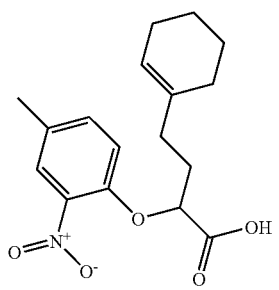
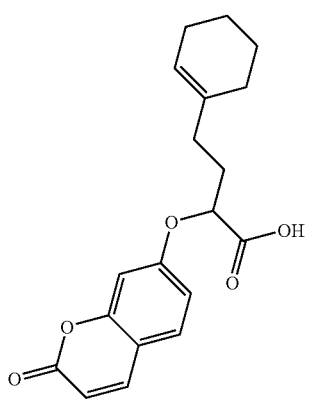

103
-continued
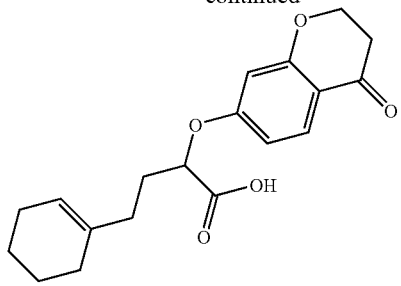
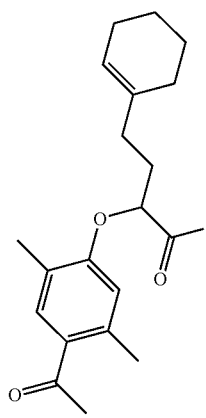
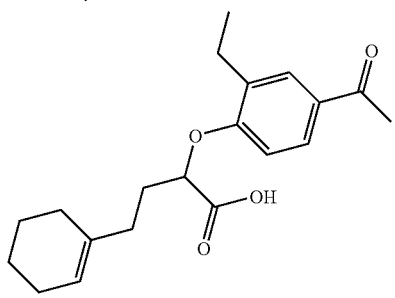
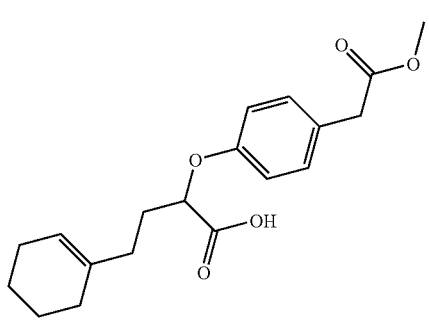
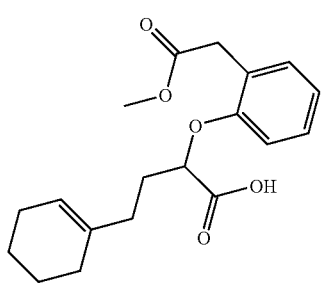
104
-continued
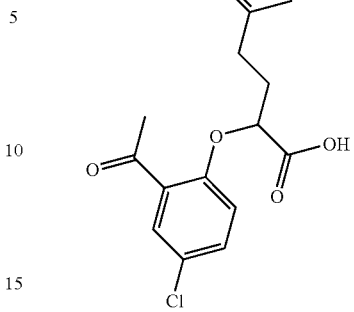
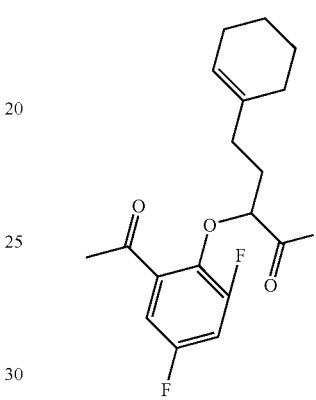
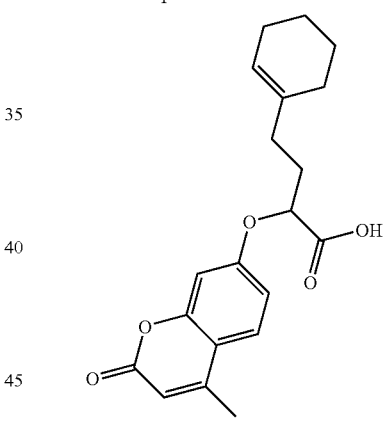
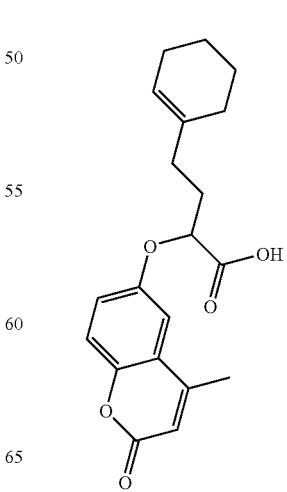

105
-continued
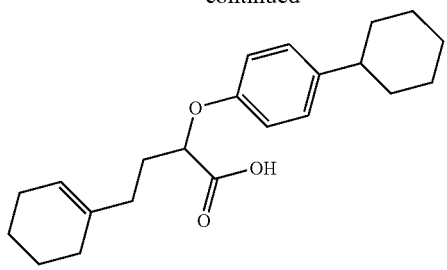
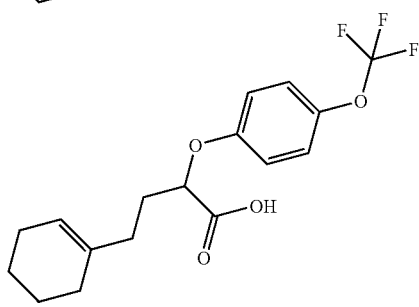
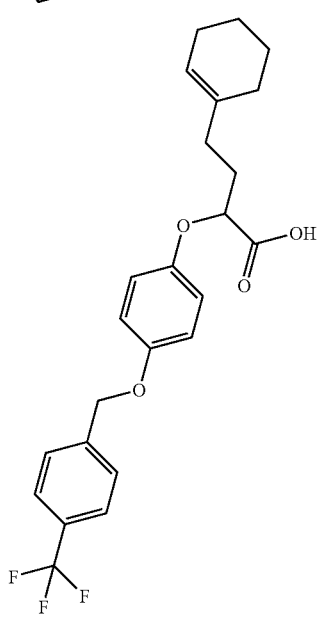
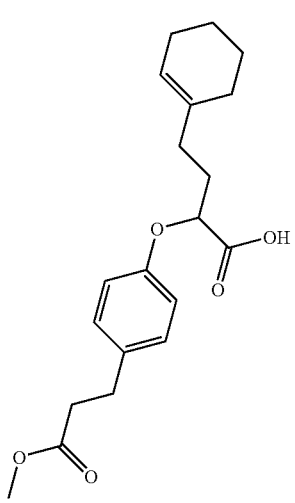
106
-continued
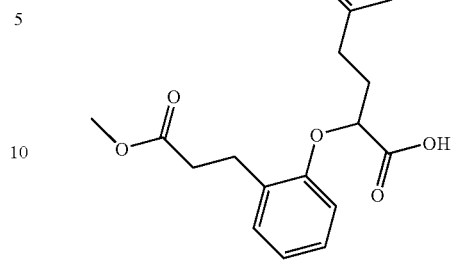
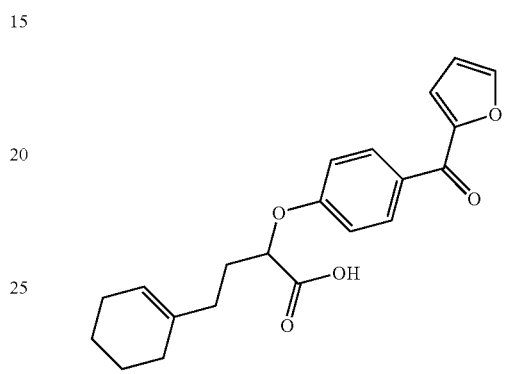
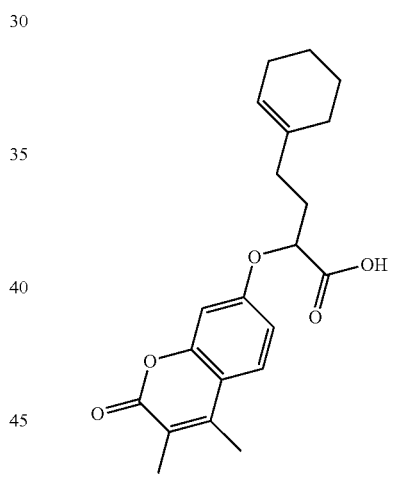
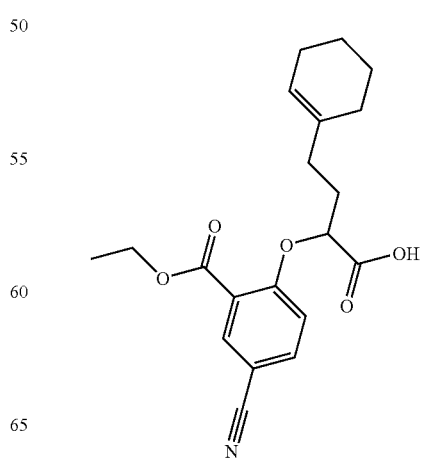

107
-continued
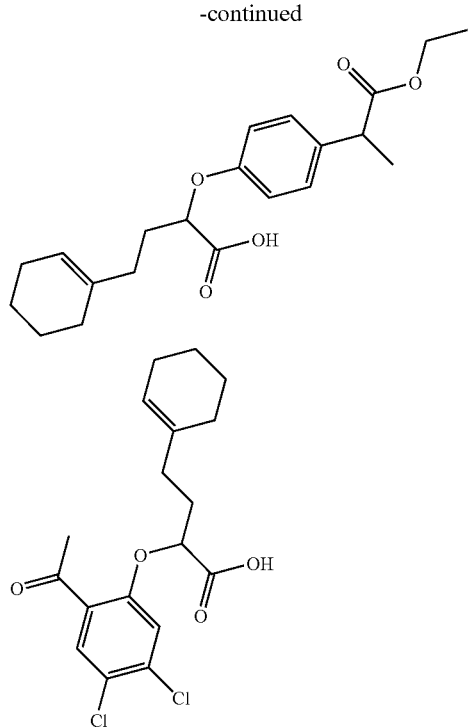
108
-continued
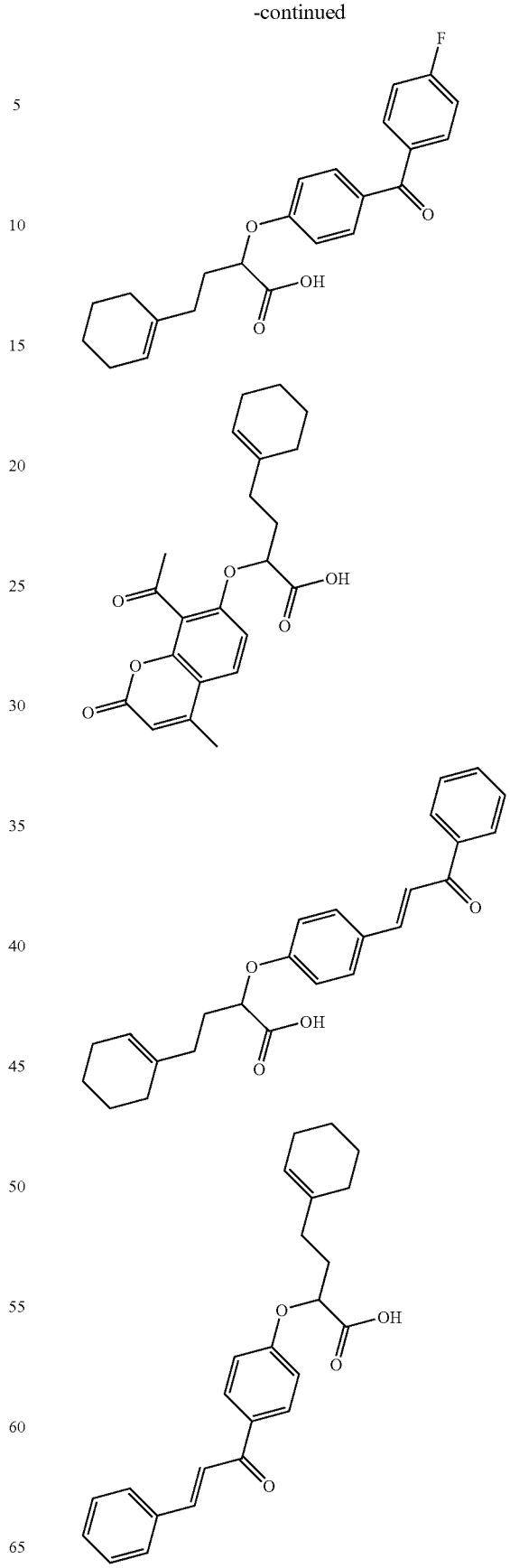

109
-continued
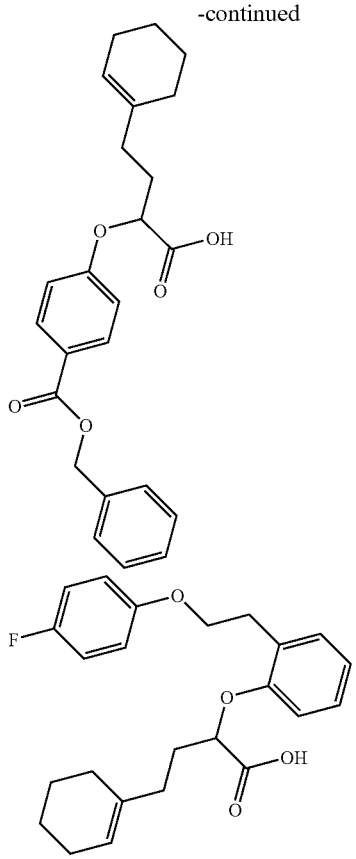
110
-continued
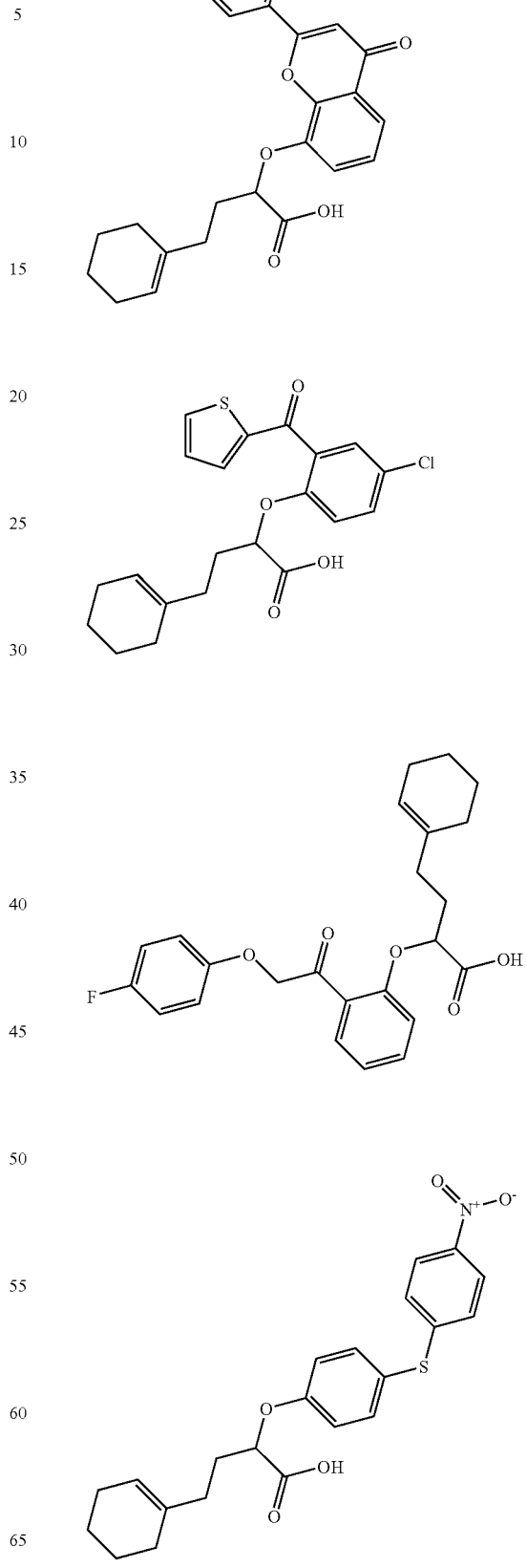
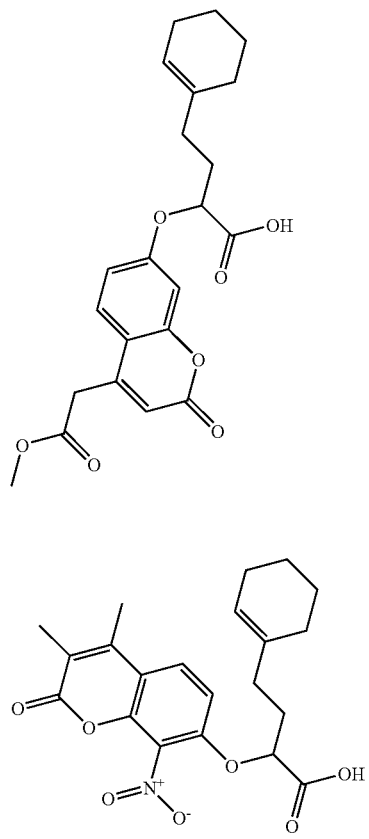

111
-continued
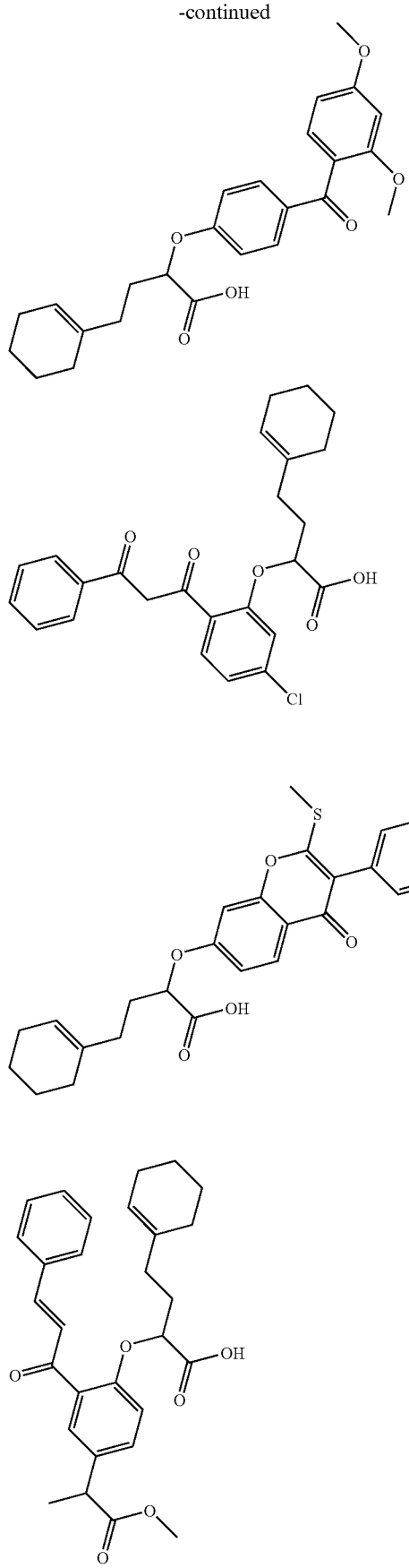
112
-continued
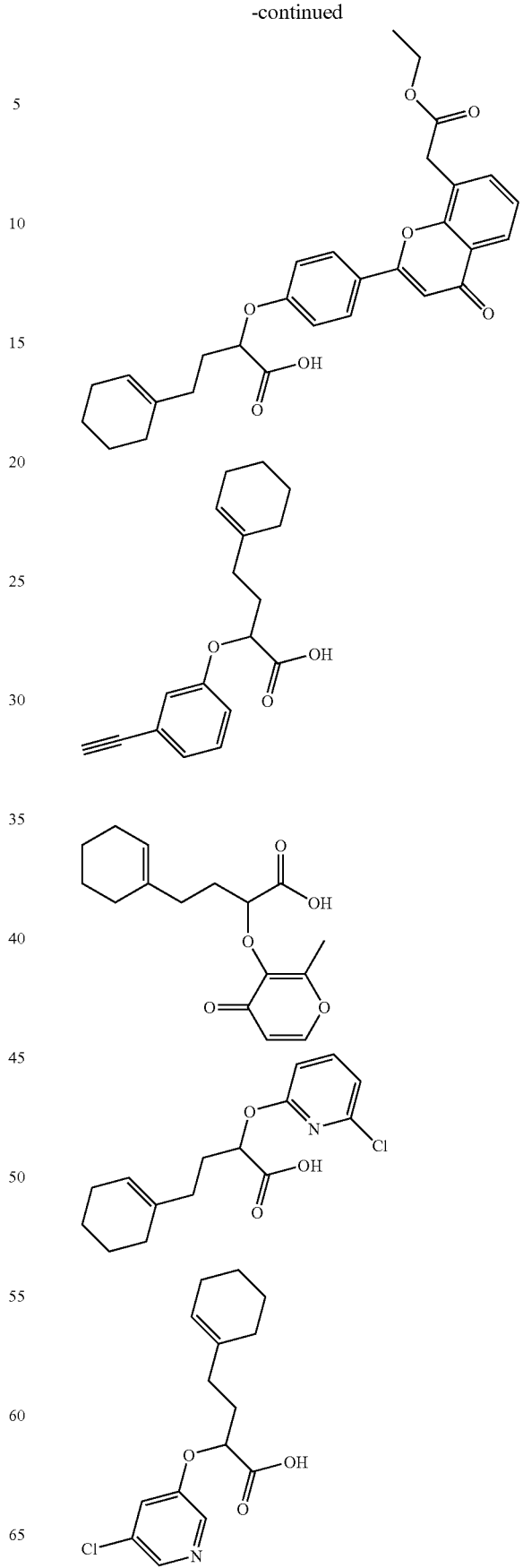

113
-continued
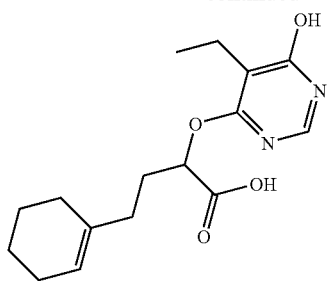
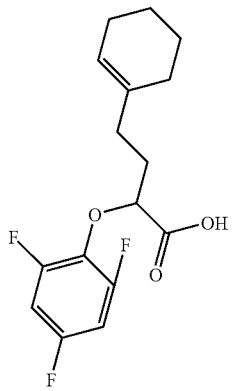
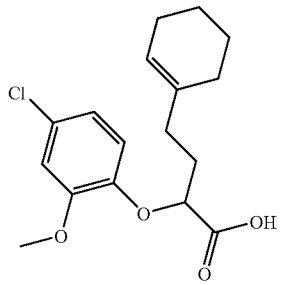
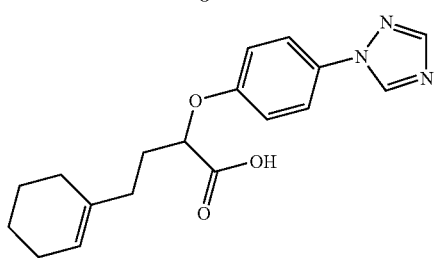
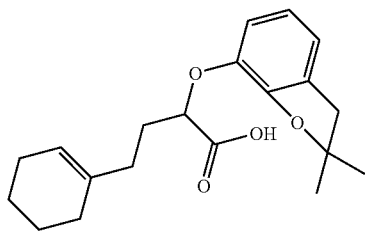
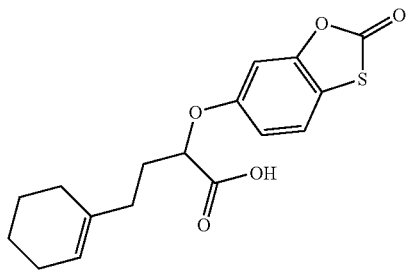
114
-continued
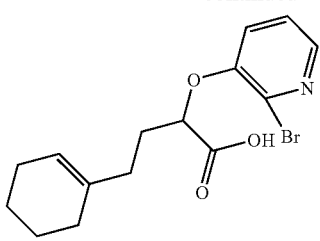
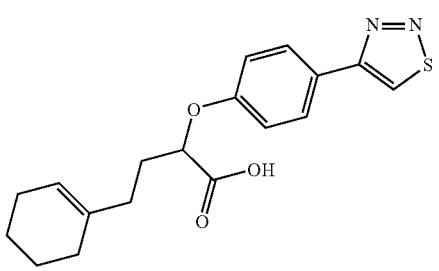
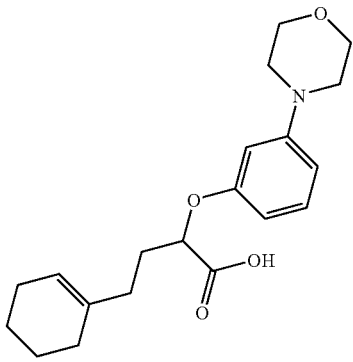
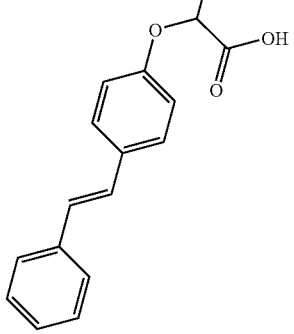

115
-continued
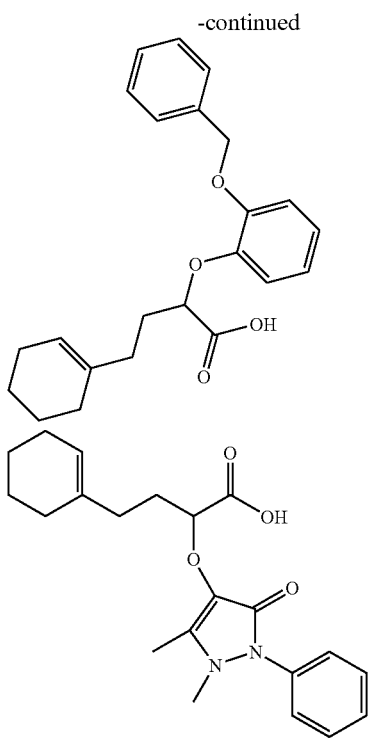
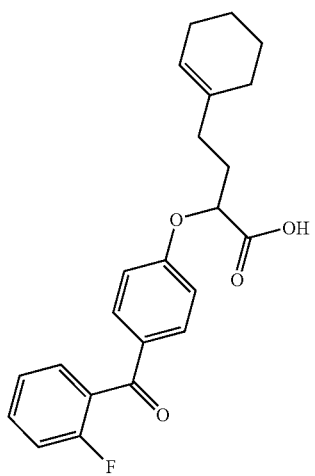
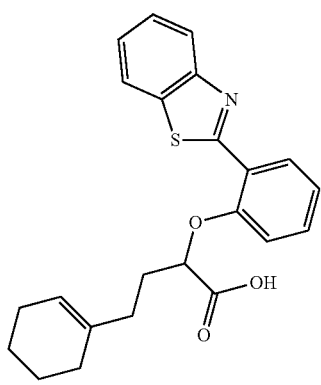
116
-continued
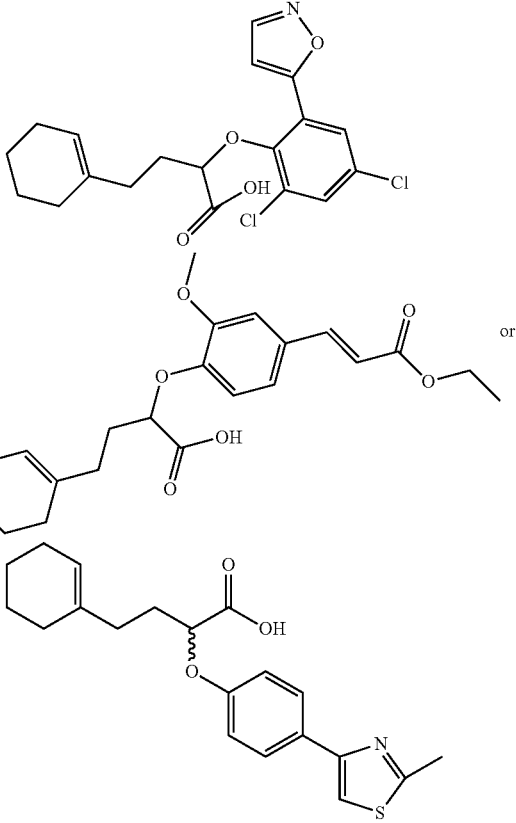
or a pharmaceutically acceptable salt thereof.
5. A compound according to claim 1, which is
ethyl 2-[(4-trifluoromethylphenyl)oxy]-4-cyclohex-1-en-1-ylbutanoate
4-cyclohex-1-enyl-2-[4-(trifluoromethyl)phenoxy]butanoic acid
4-cyclohex-1-enyl-2-[4-(2-methoxycarbonylvinyl)phenoxy]butanoic acid
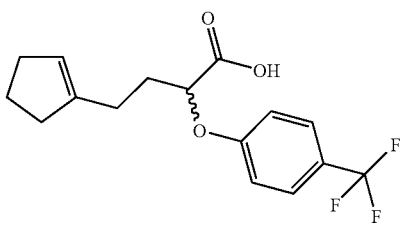
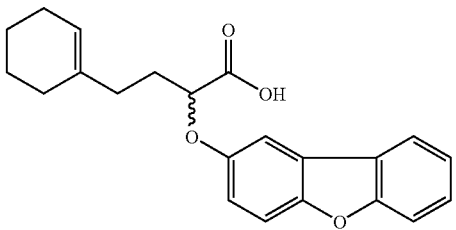

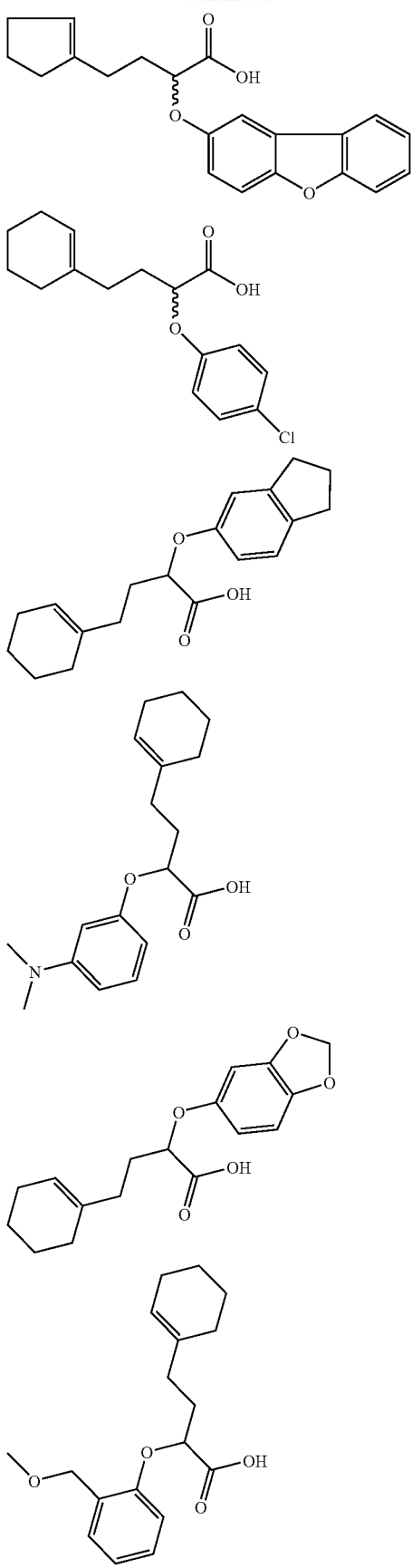
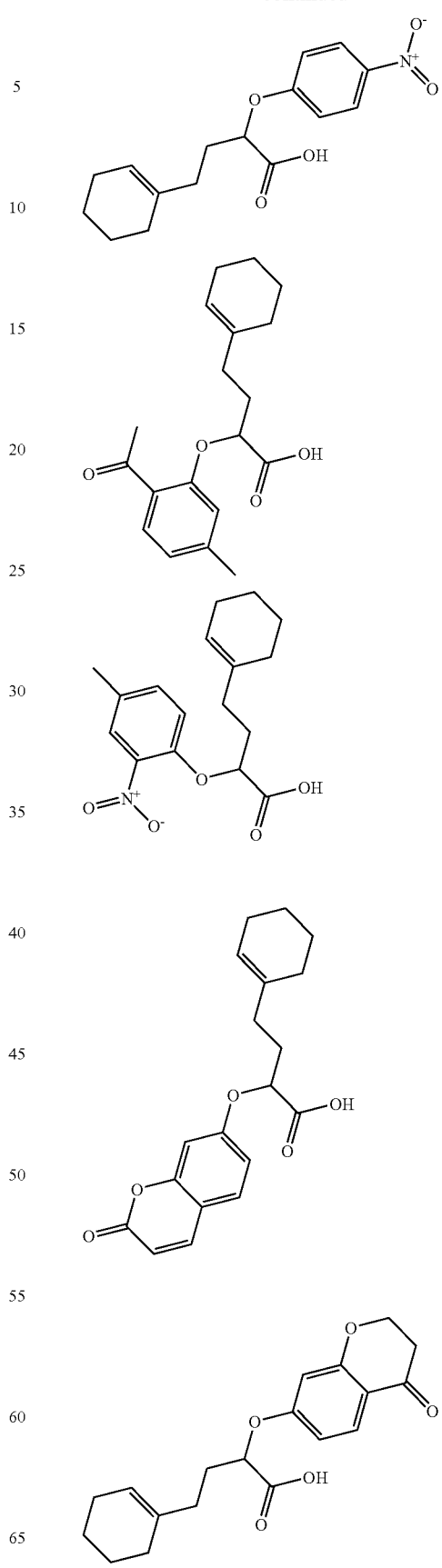

119
-continued
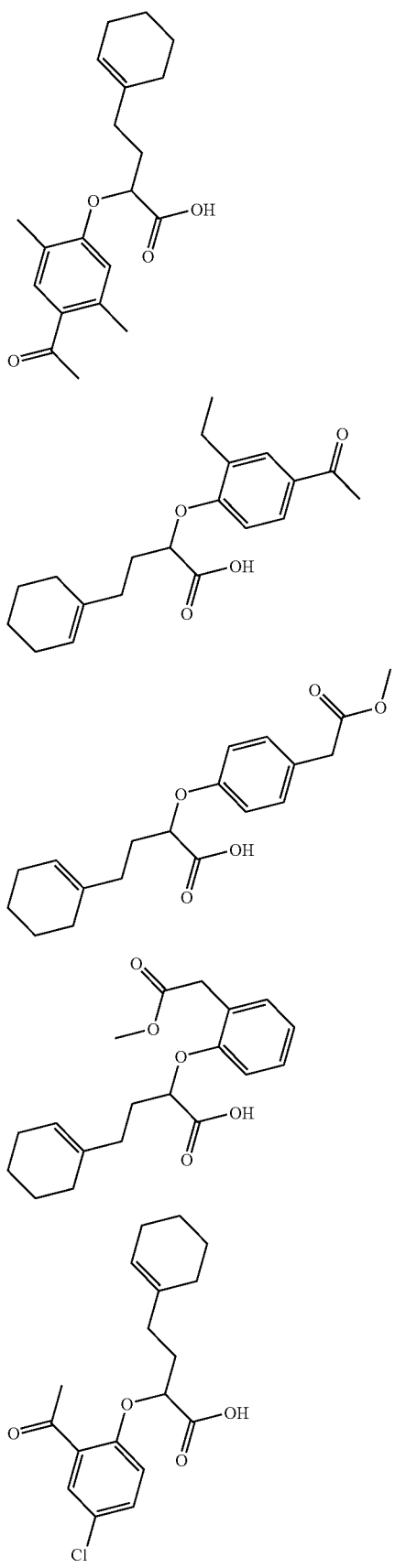
120
-continued
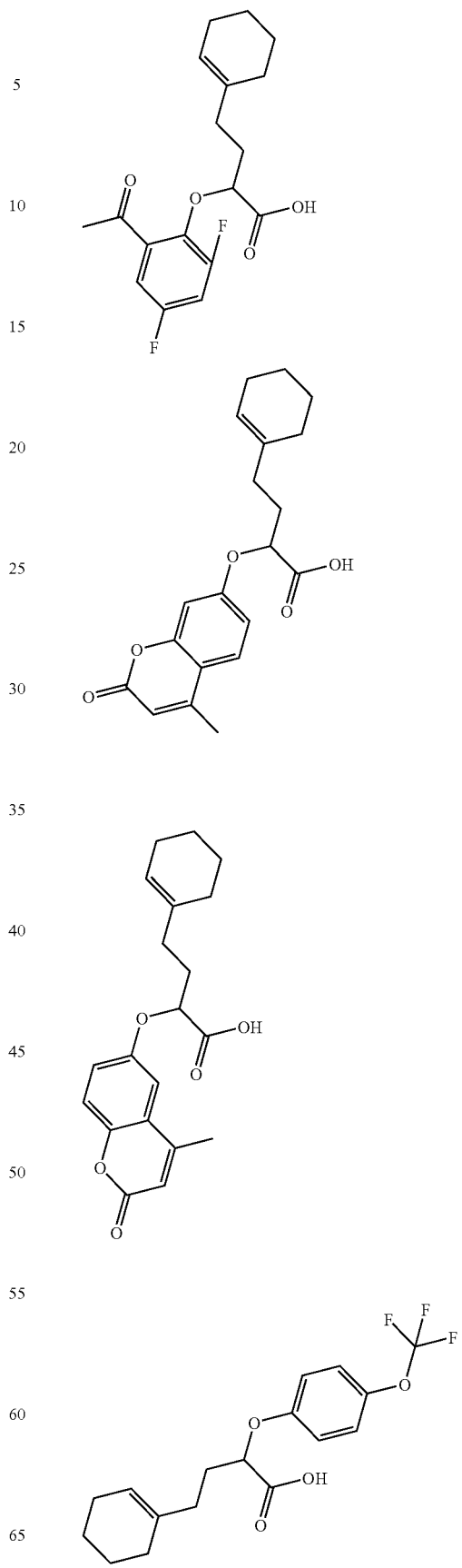

121
-continued
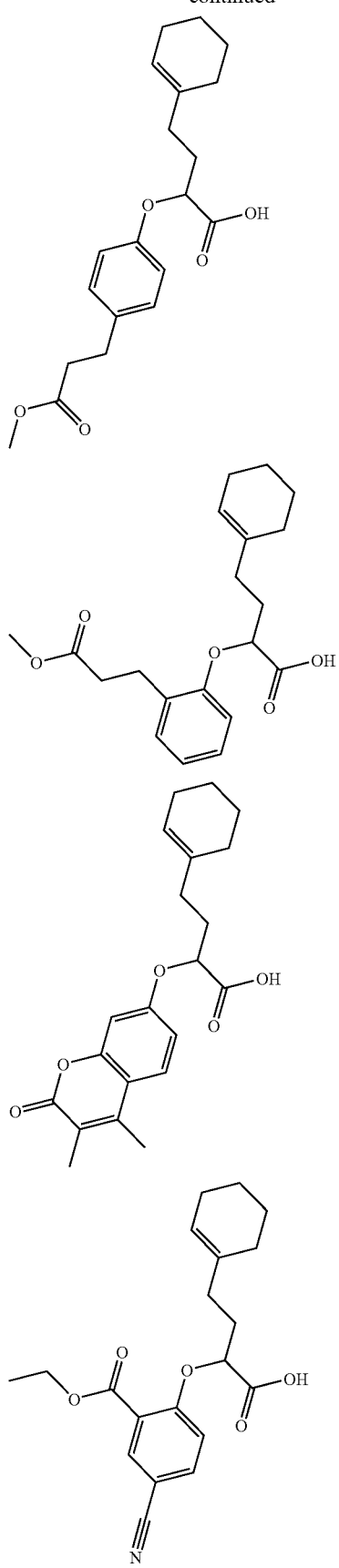
122
-continued
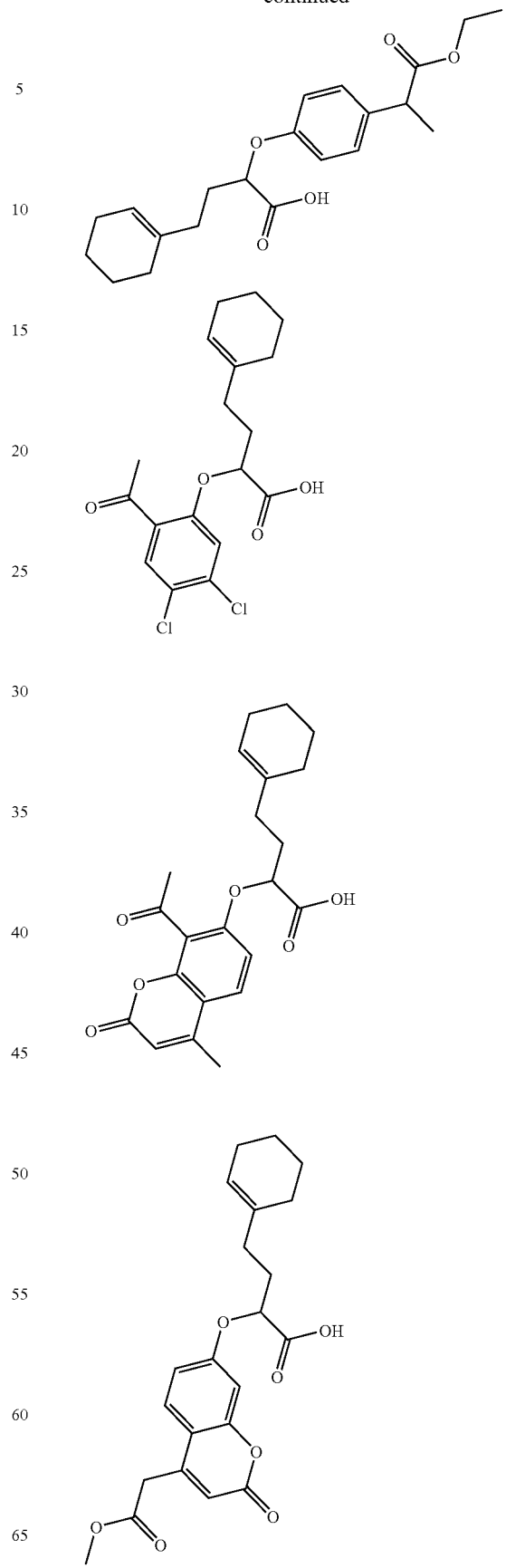

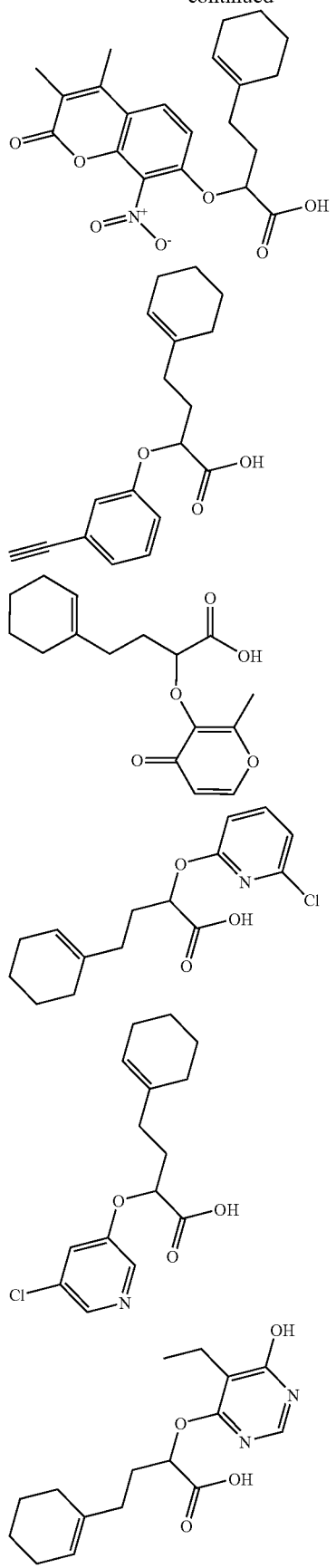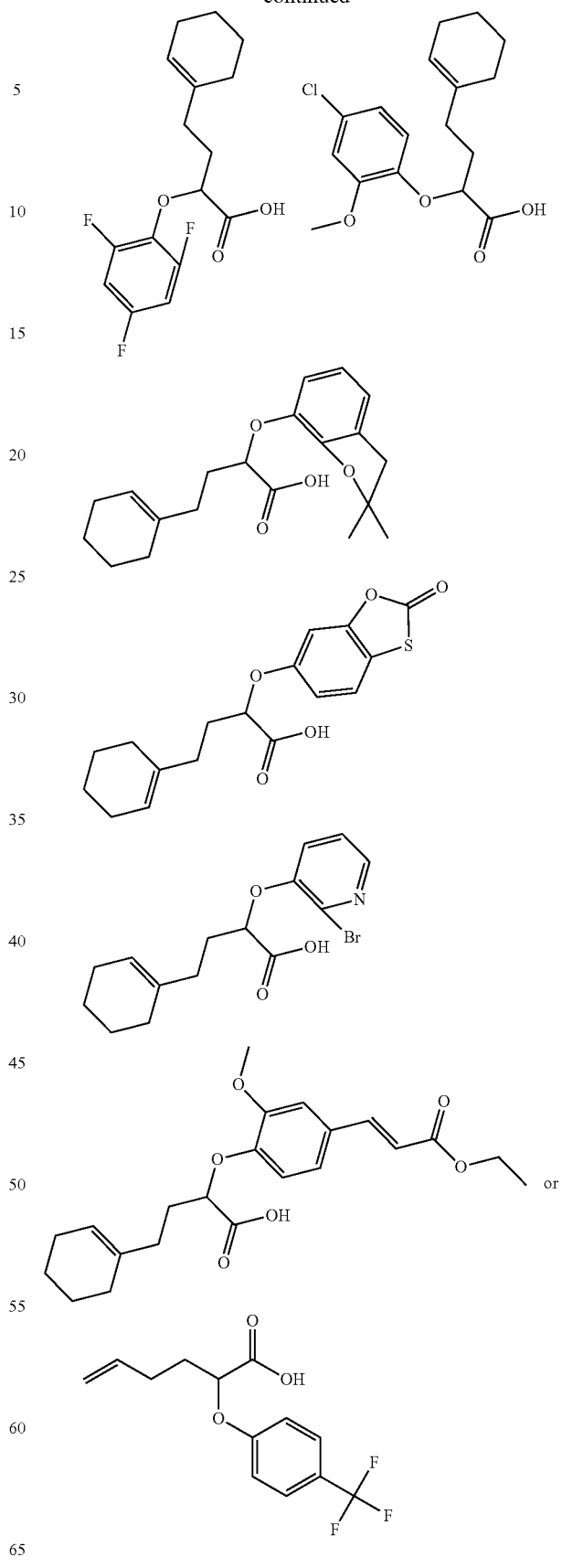
or a pharmaceutically acceptable salt thereof.

6. A compound according to claim 1, which is
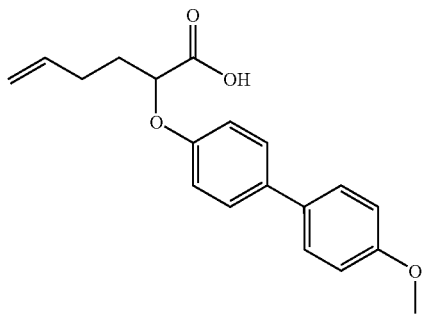
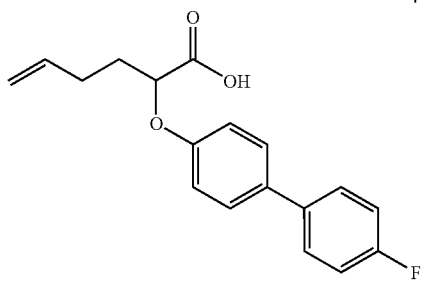
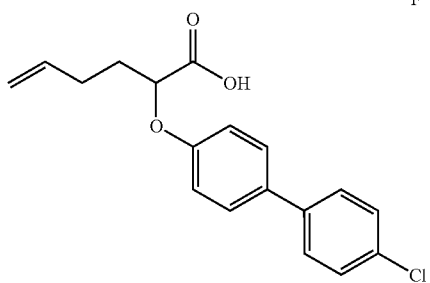
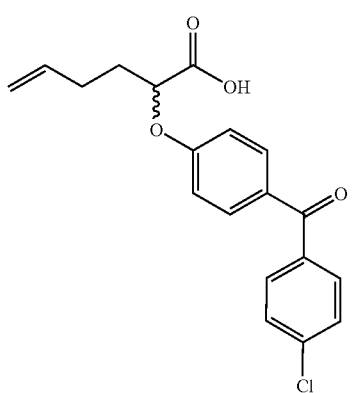
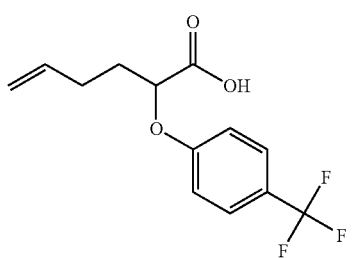
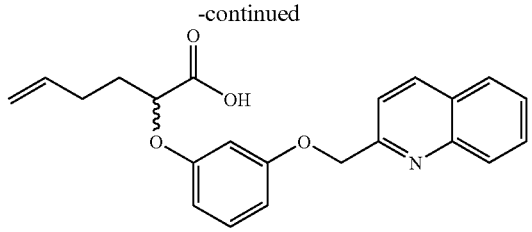
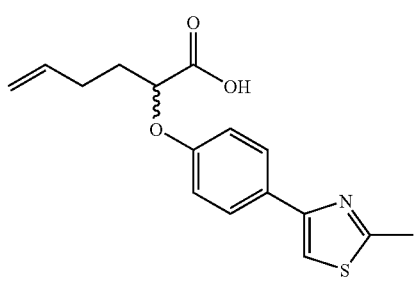
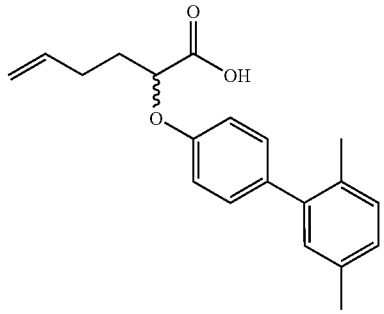
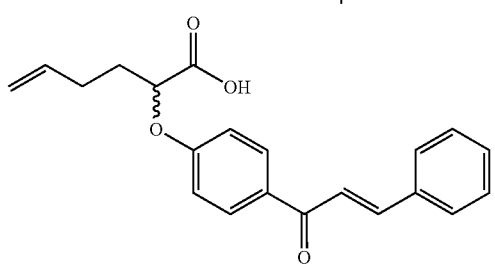
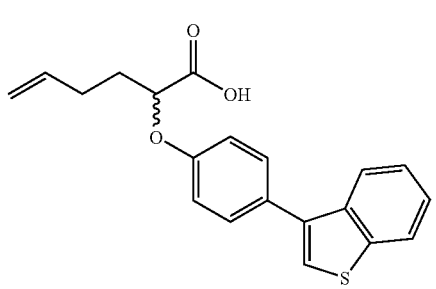
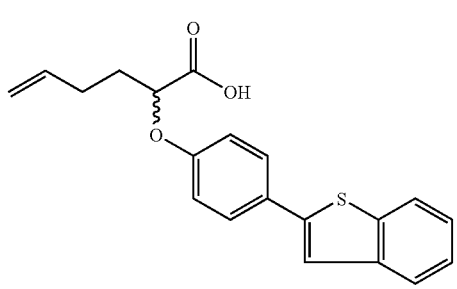

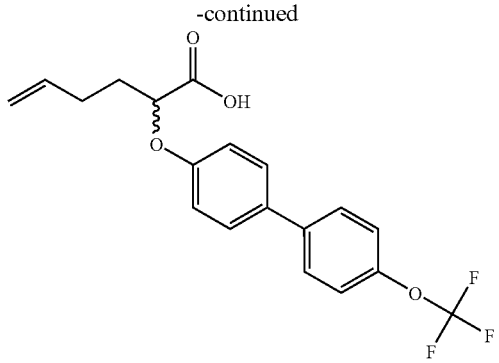
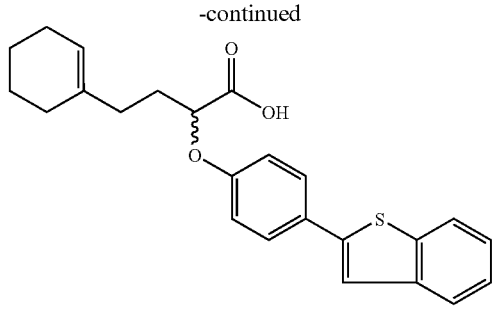
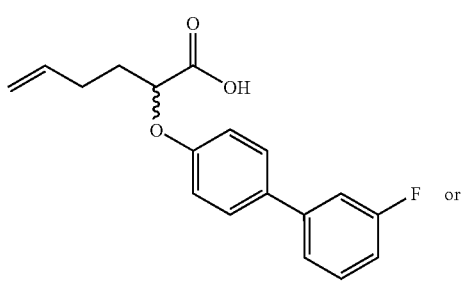
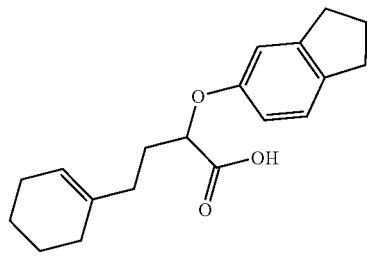
or
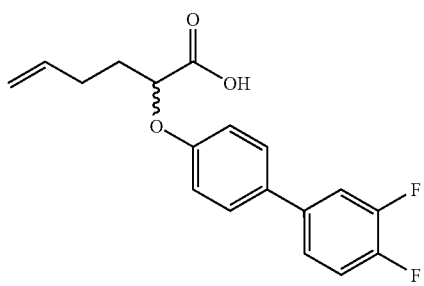
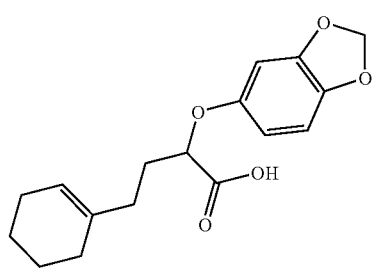
or a pharmaceutically acceptable salt thereof.
7. A compound according to claim 1, which is
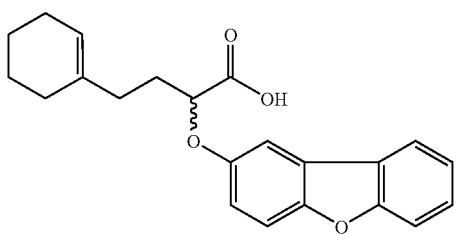
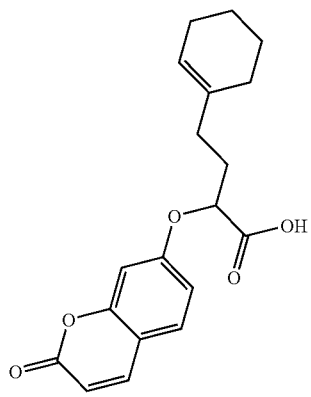
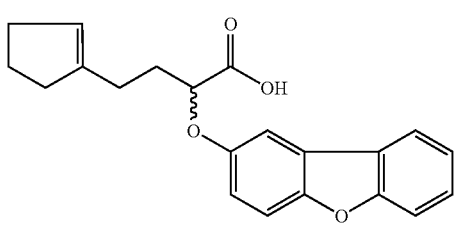
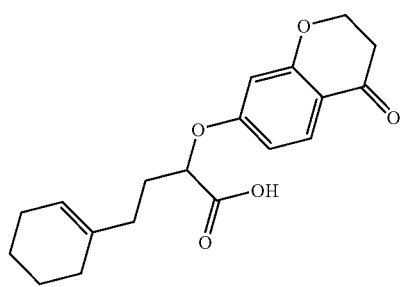

129
-continued
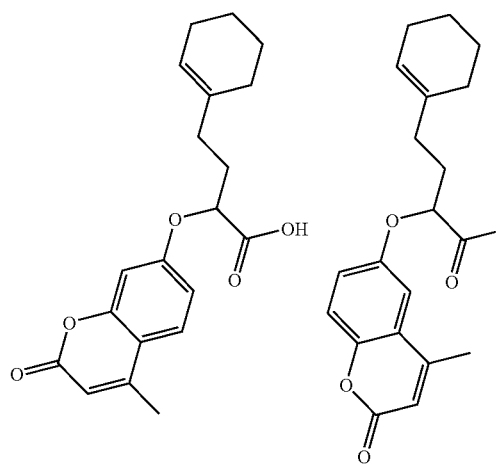
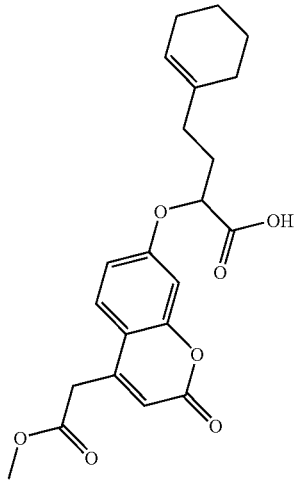
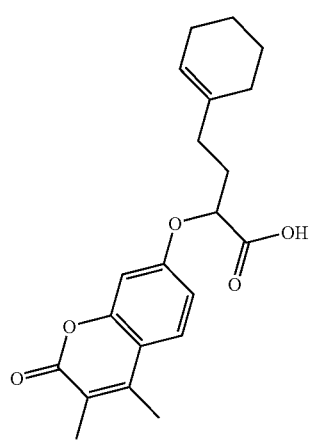
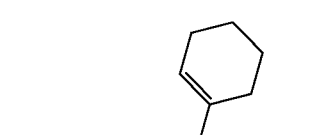
130
-continued
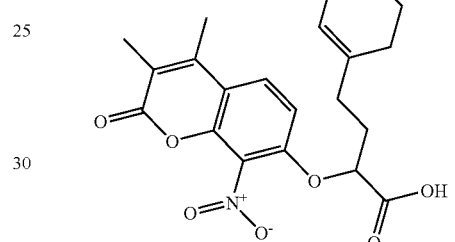
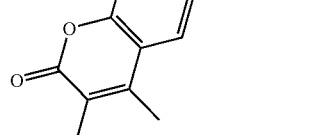
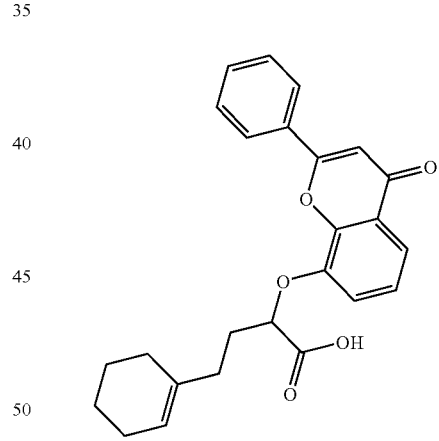
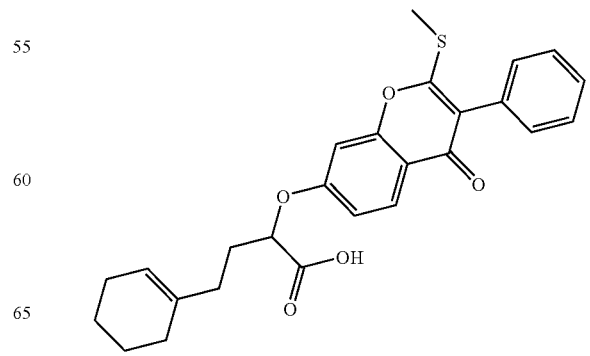

131
-continued
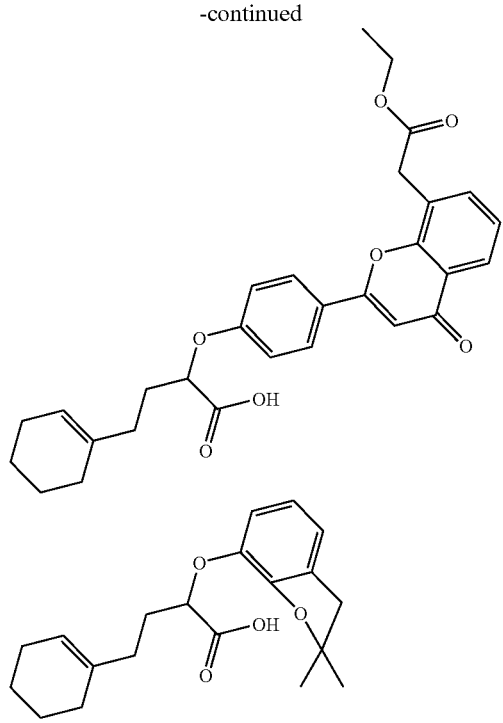
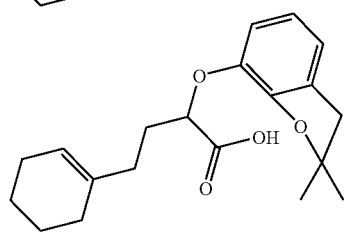
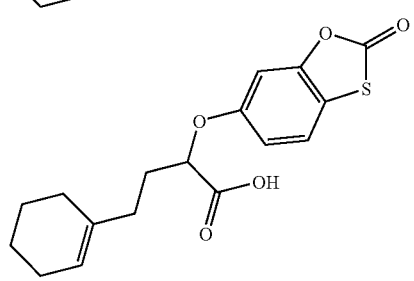
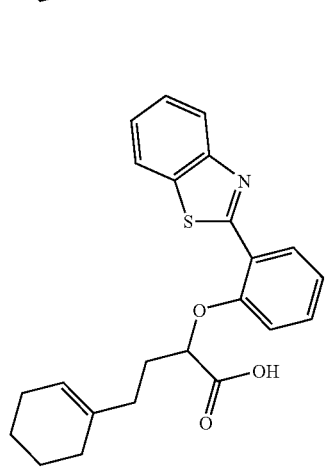
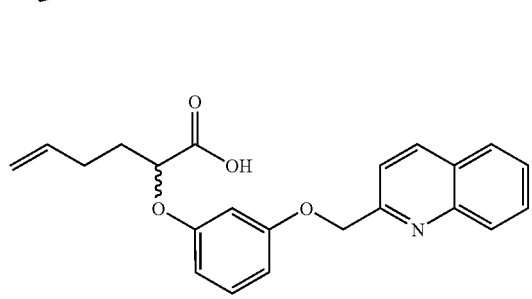
132
-continued
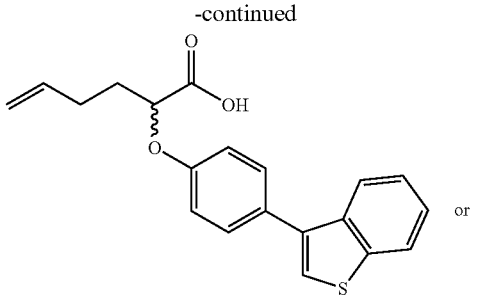
or
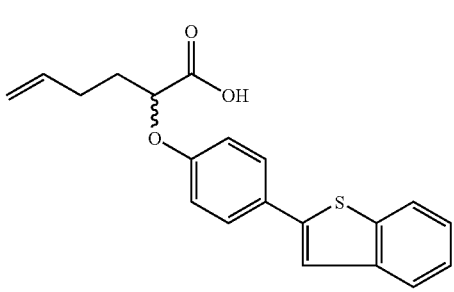
or a pharmaceutically acceptable salt thereof.
8. A compound according to claim 1, which is
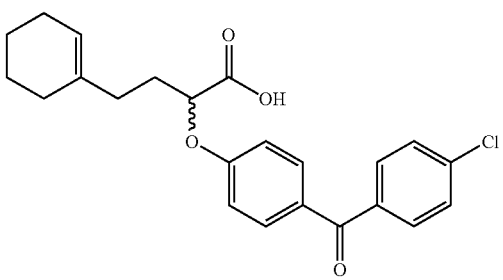
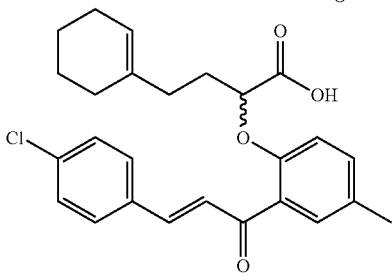
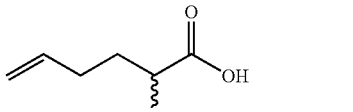
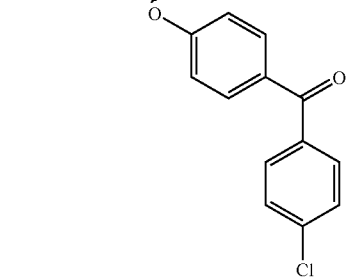

133
-continued
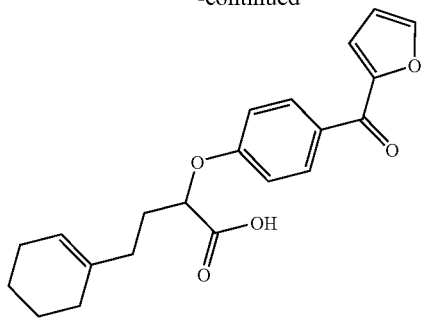
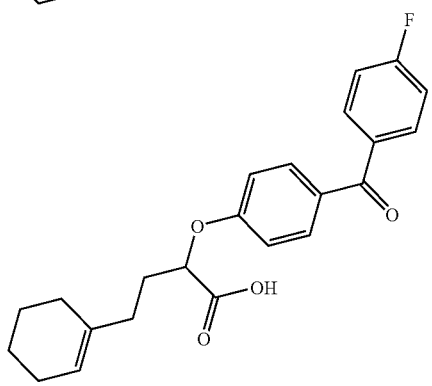
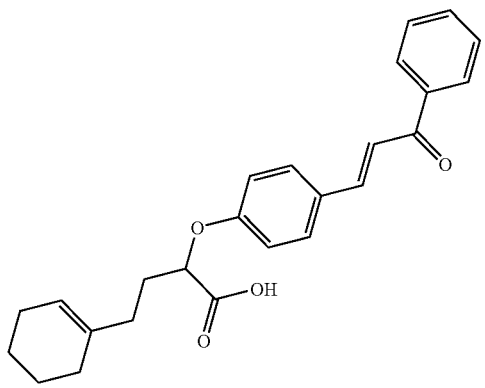
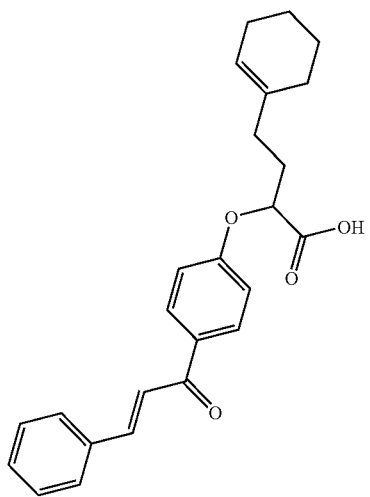
134
-continued
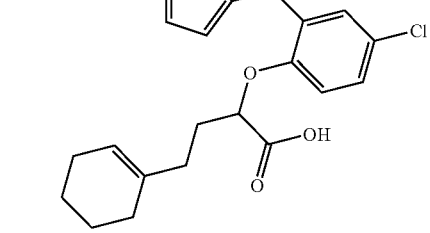
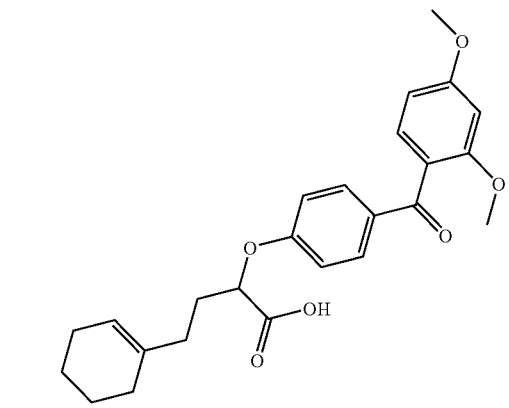
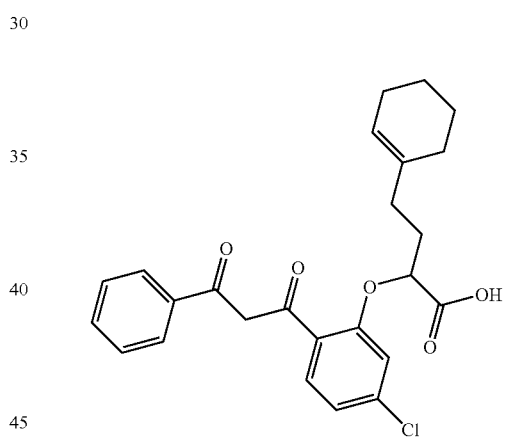
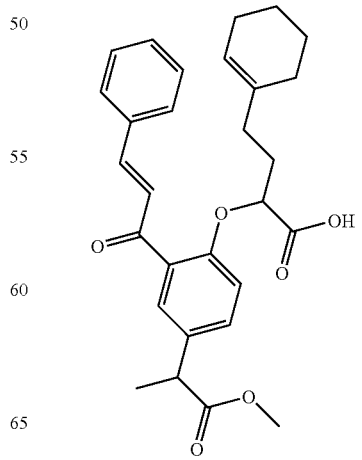

-continued
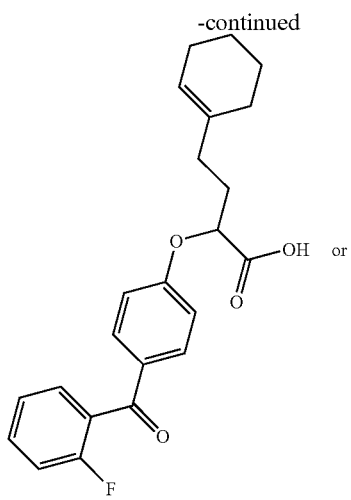
or a pharmaceutically acceptable salt thereof.
9. A compound according to claim 1, which is
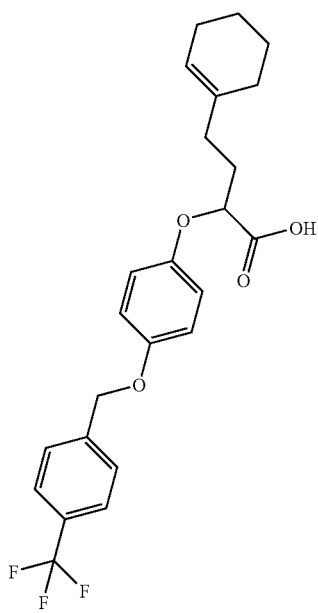
-continued
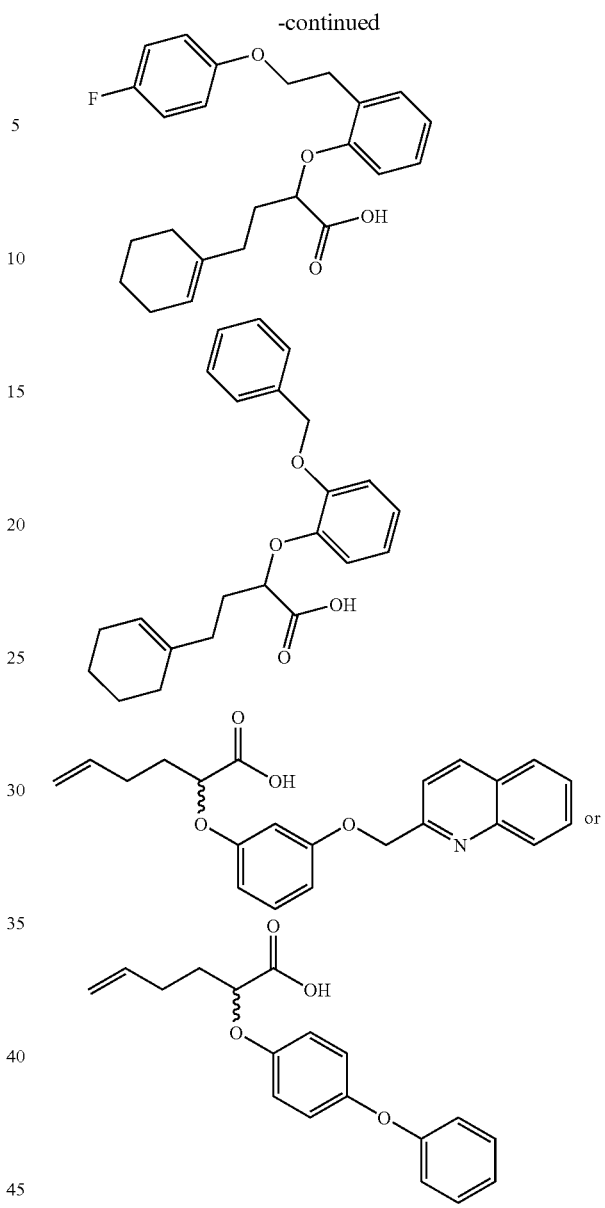
or a pharmaceutically acceptable salt thereof.
10. A compound according to claim 1, which is
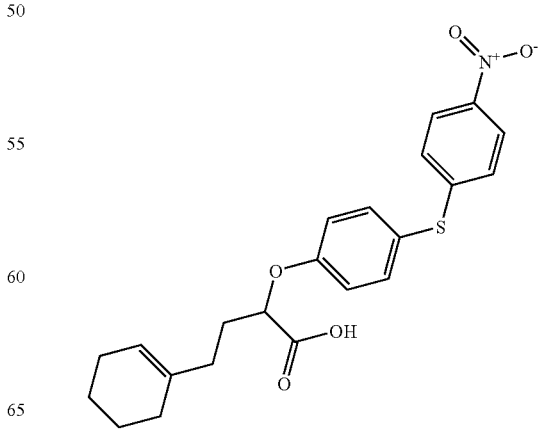
or a pharmaceutically acceptable salt thereof,

11. A compound according to claim 1, which is

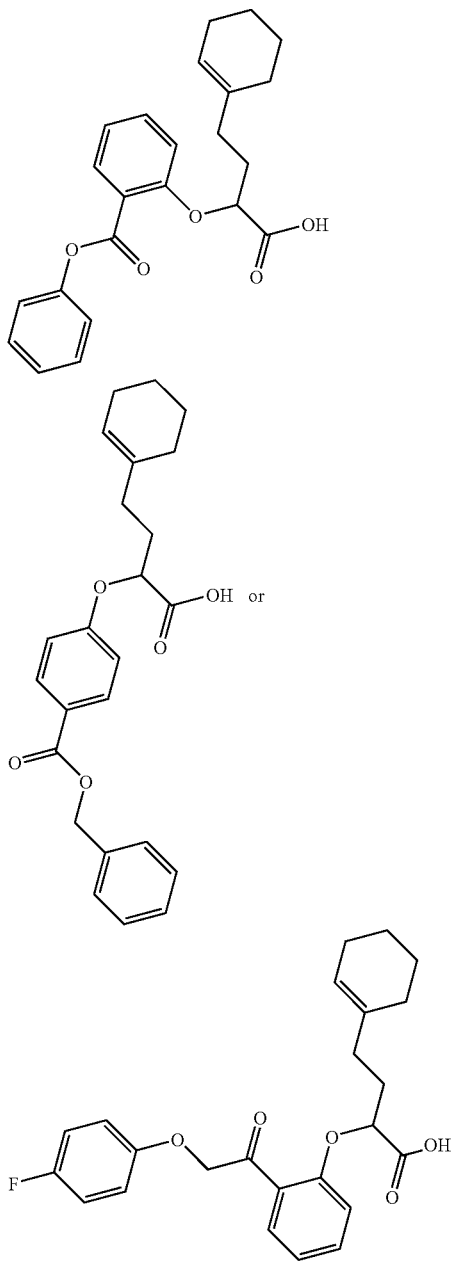

or a pharmaceutically acceptable salt thereof.

12. A compound according to claim 1, which is
ethyl 2-[(4-trifluoromethylphenyl)oxy]-4-cyclohex-1-en-1-ylbutanoate
4-cyclohex-1-enyl-2-[4-(trifluoromethyl)phenoxy]butanoic acid
ethyl 2-[4-(5-chlorothiophen-2-yl)-phenoxy]-4-cyclohex-1-enylbutanoate
2-[4-(5-chlorothiophen-2-yl)phenoxy]-4-cyclohex-1-enylbutanoic acid
methyl 4-cyclohex-1-en-1-yl-2-[(4'-methoxy-1,1'-biphenyl-4-yl)oxy]butanoate
4-cyclohex-1-enyl-2-(4'-methoxy-1,1'-biphenyl-4-yloxy)butanoic acid
4-cyclohex-1-enyl-2-[4-(2-methoxycarbonylvinyl)phenoxy]butanoic acid

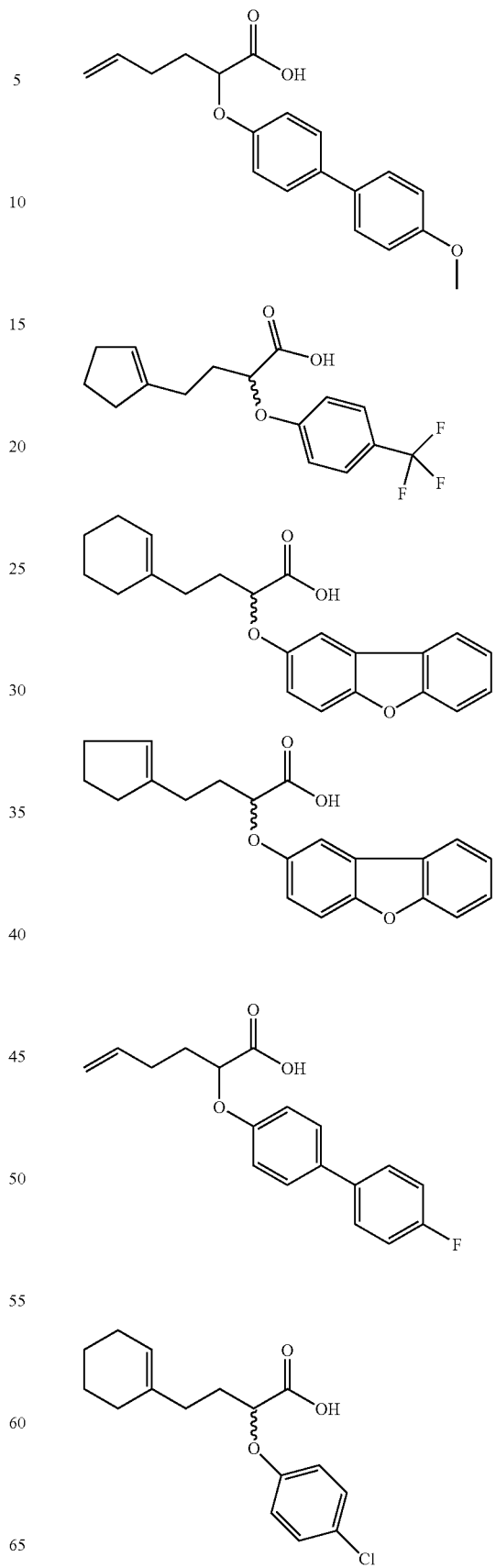

139
-continued
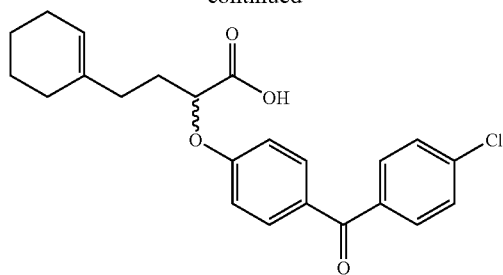
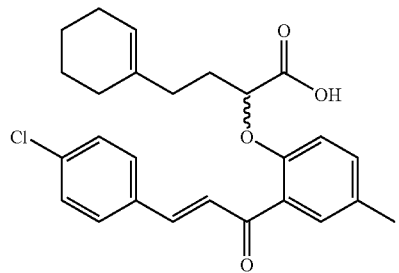
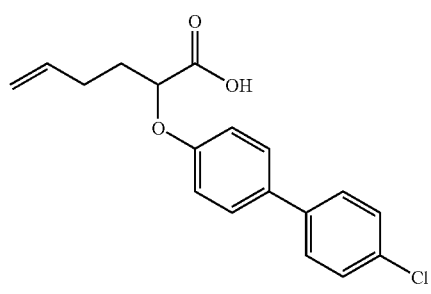
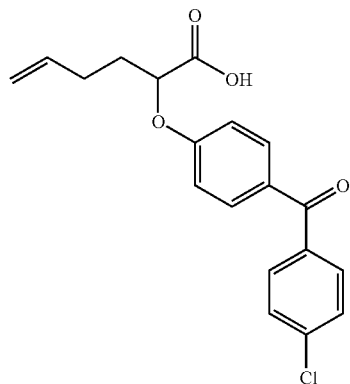
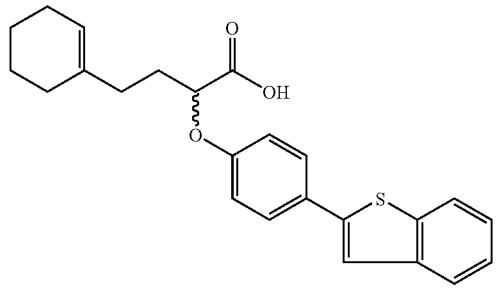
140
-continued
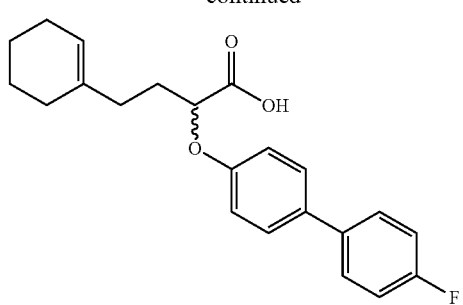
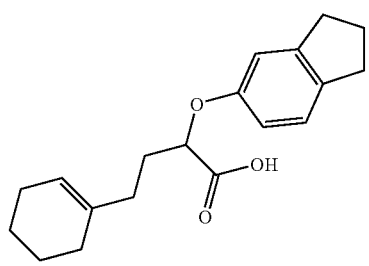
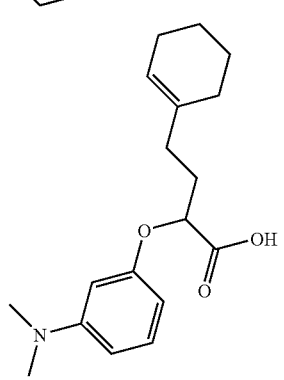
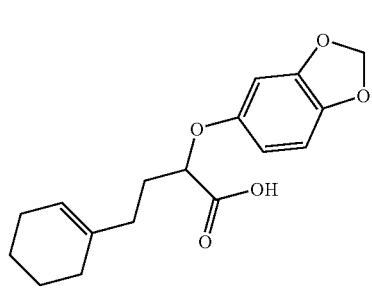
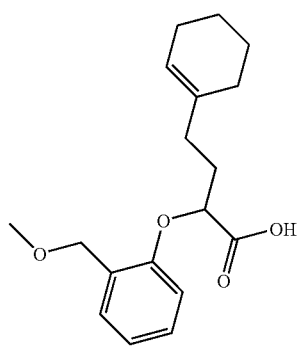

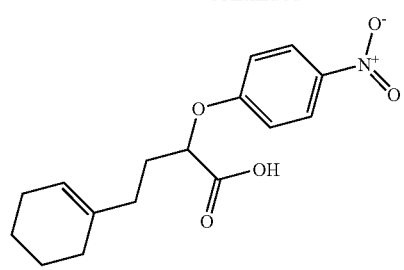
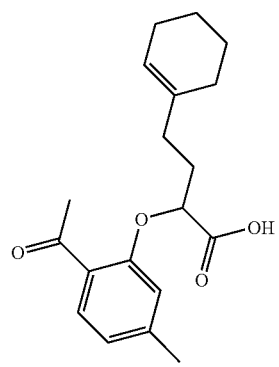
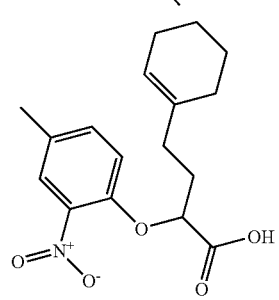
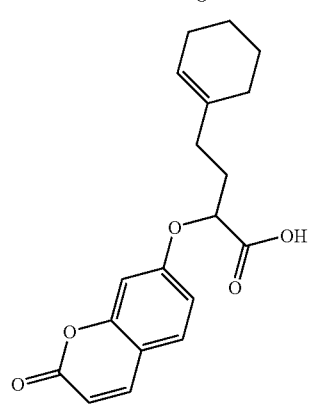
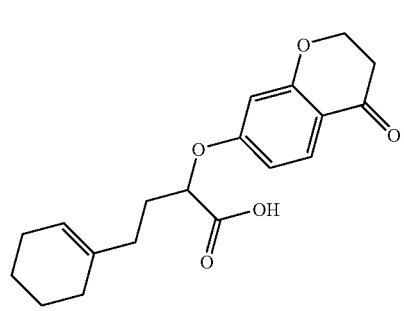
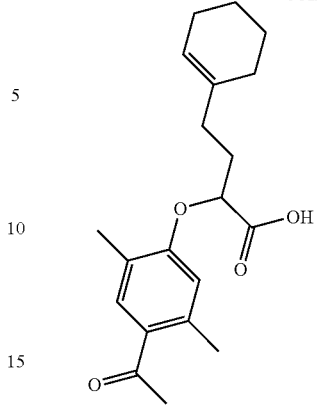
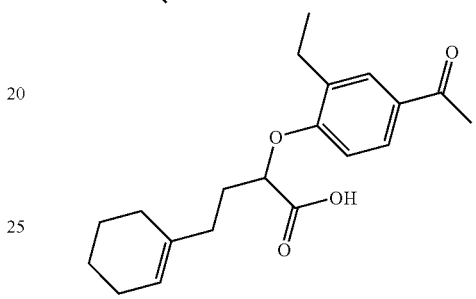
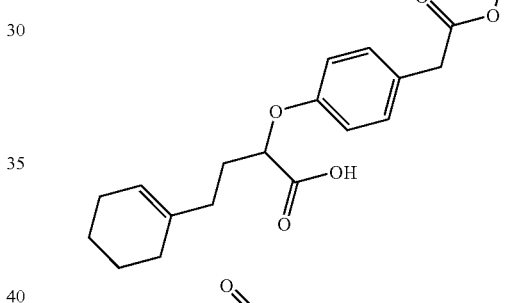
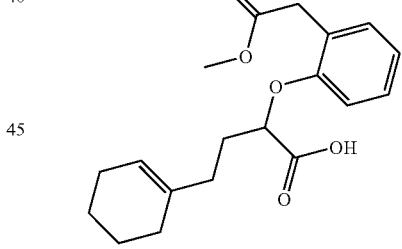
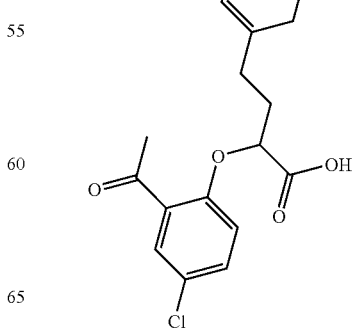

143
-continued
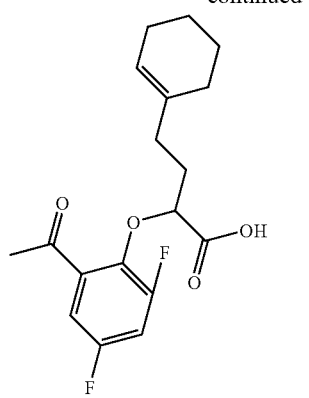
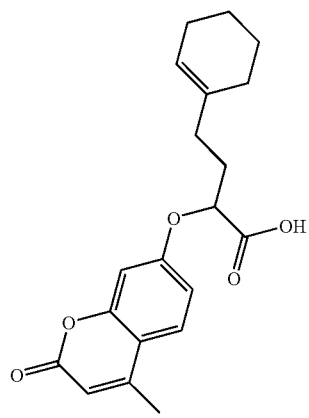
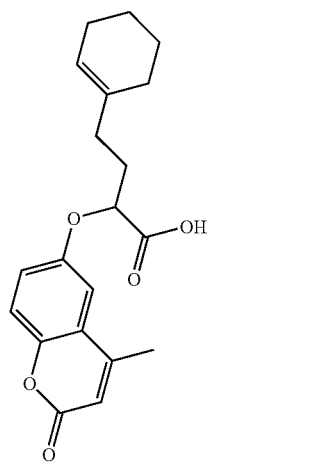
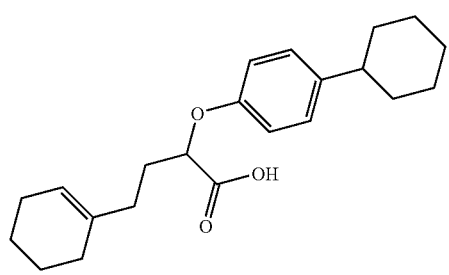
144
-continued
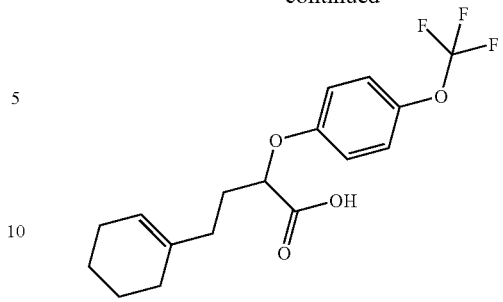
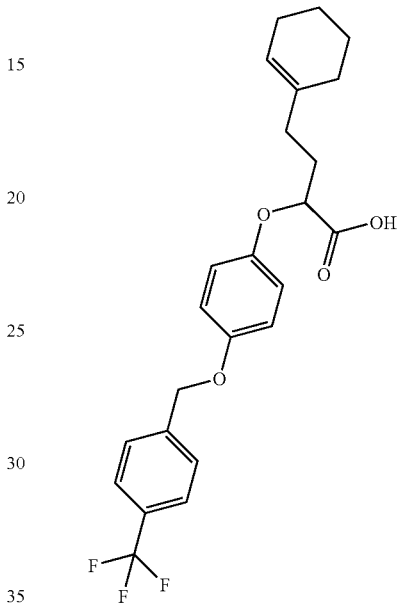
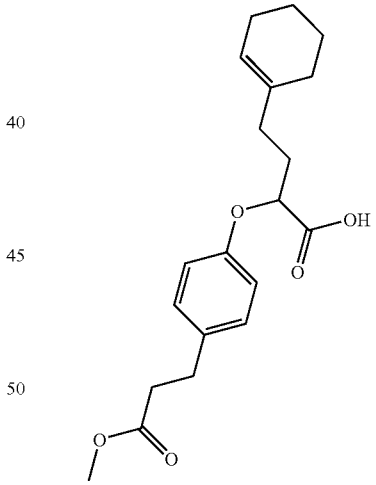
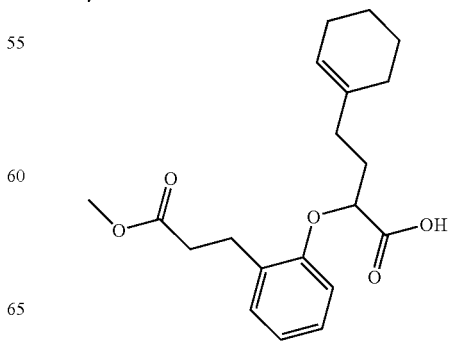

145
-continued
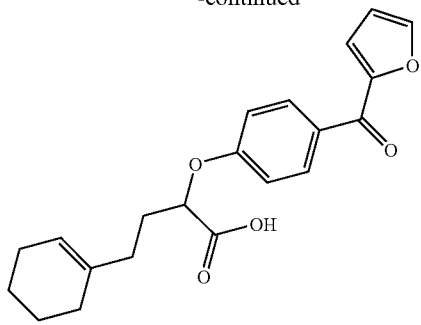
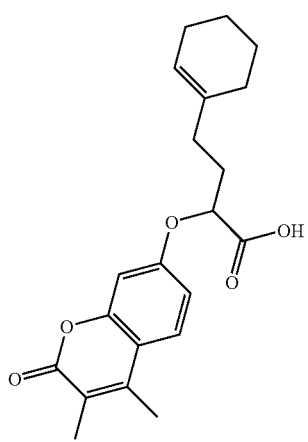
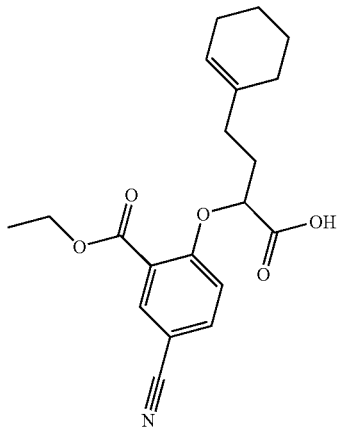
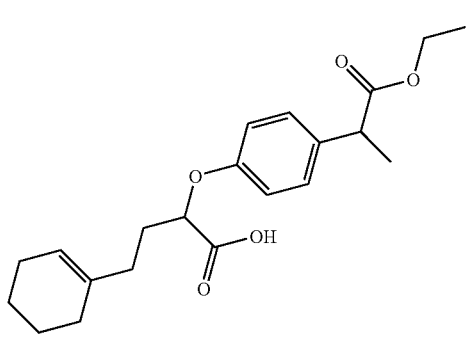
146
-continued
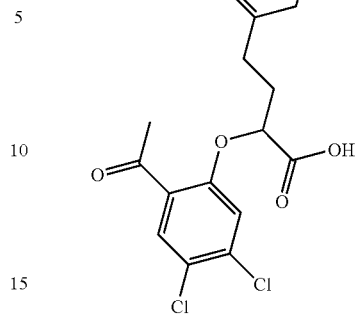
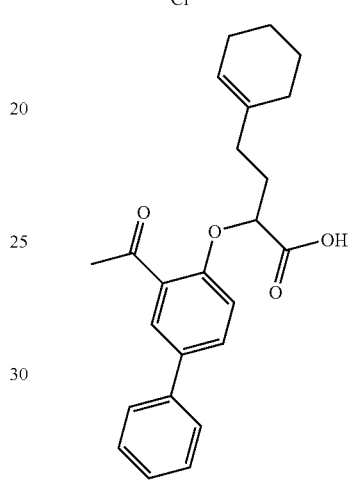
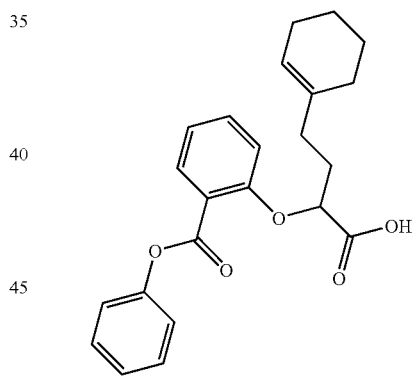
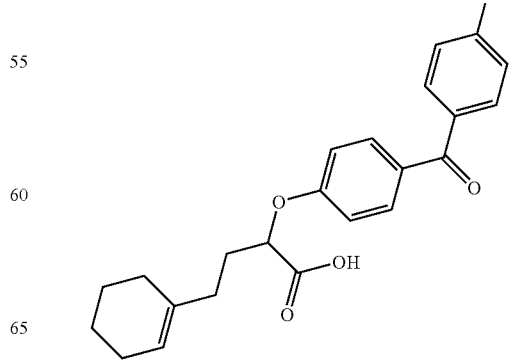

147
-continued
148
-continued
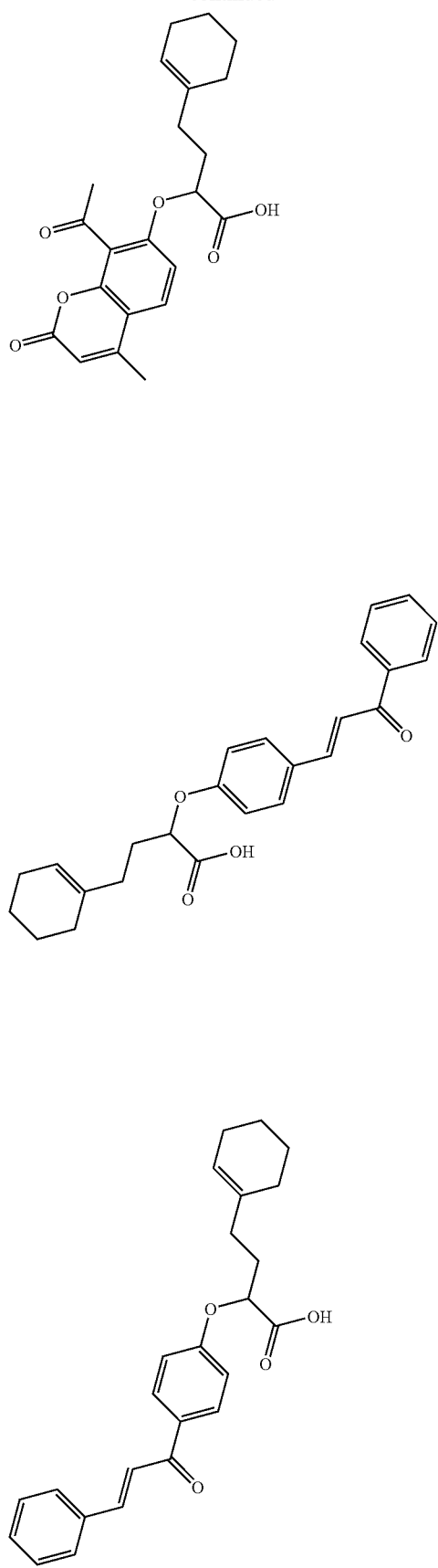
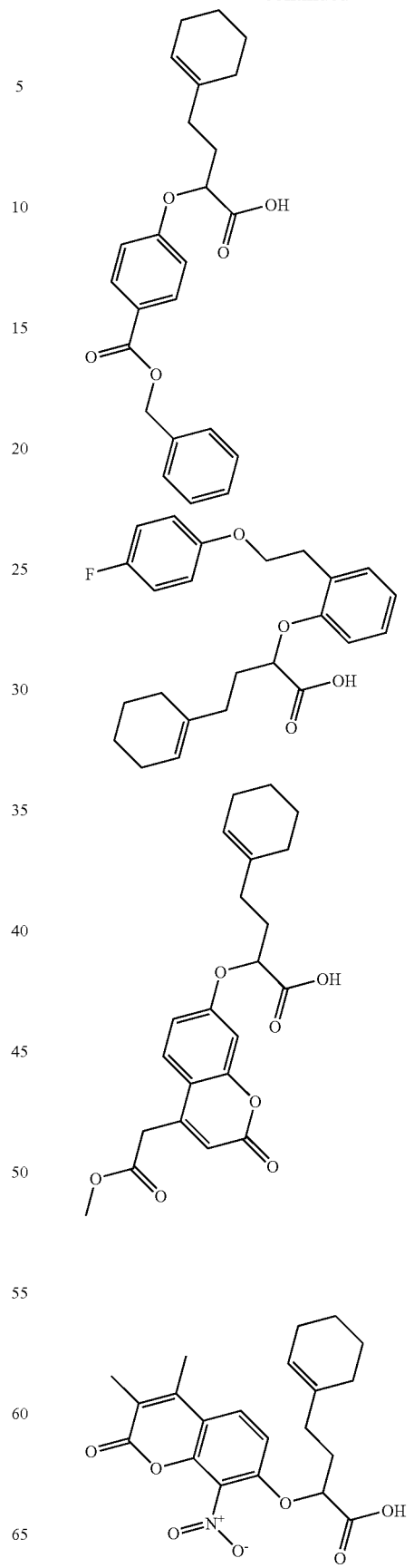

149
-continued
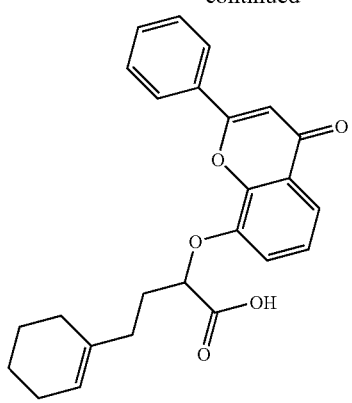
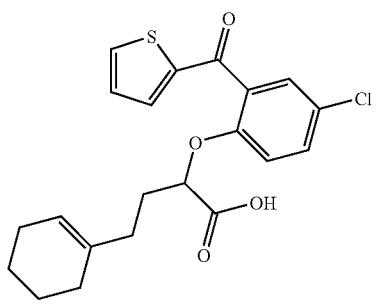
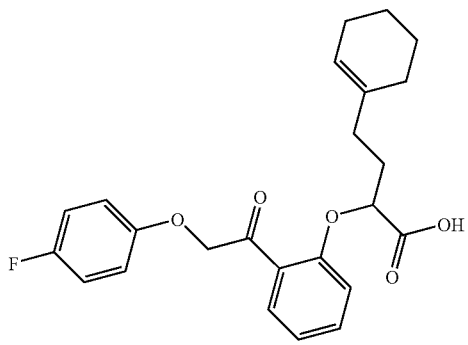
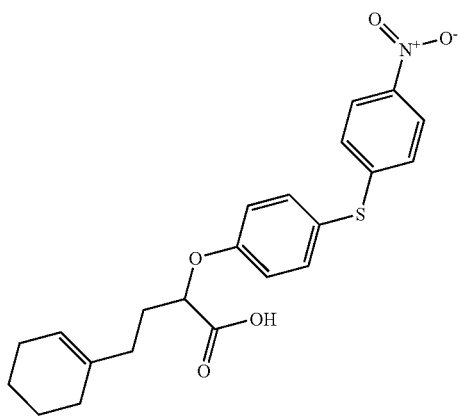
150
-continued
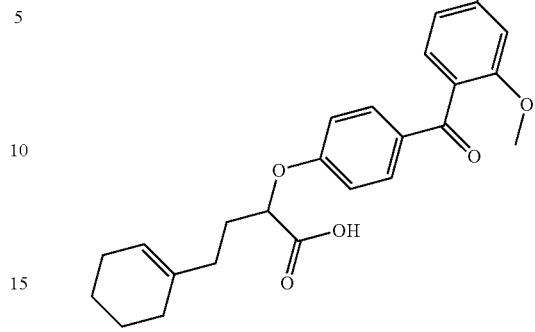
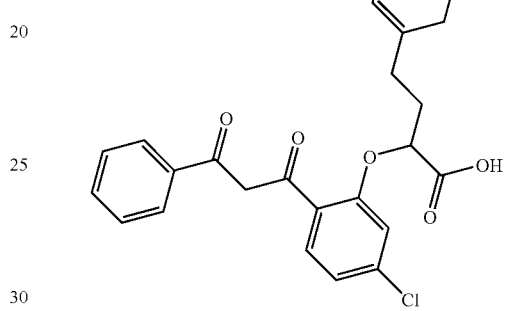
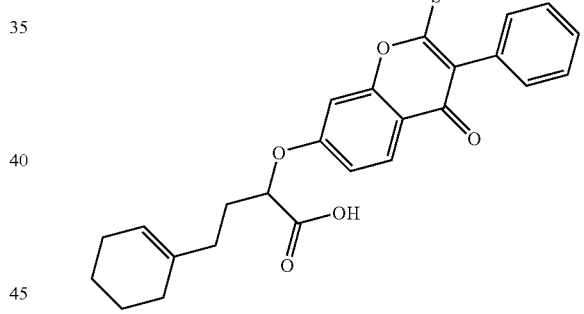
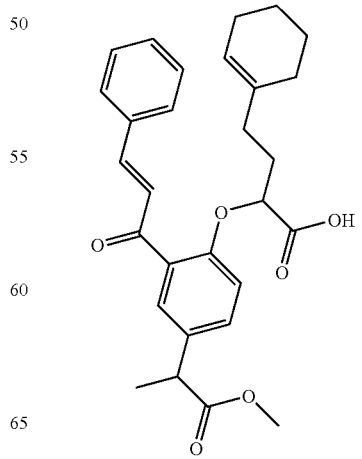

151
-continued
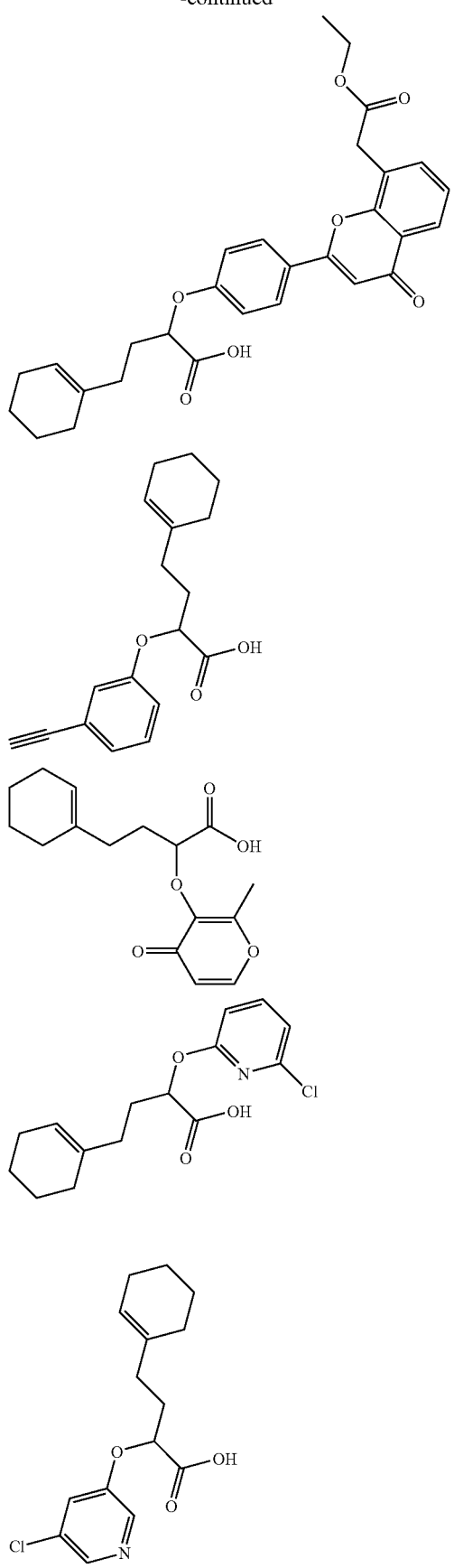
152
-continued
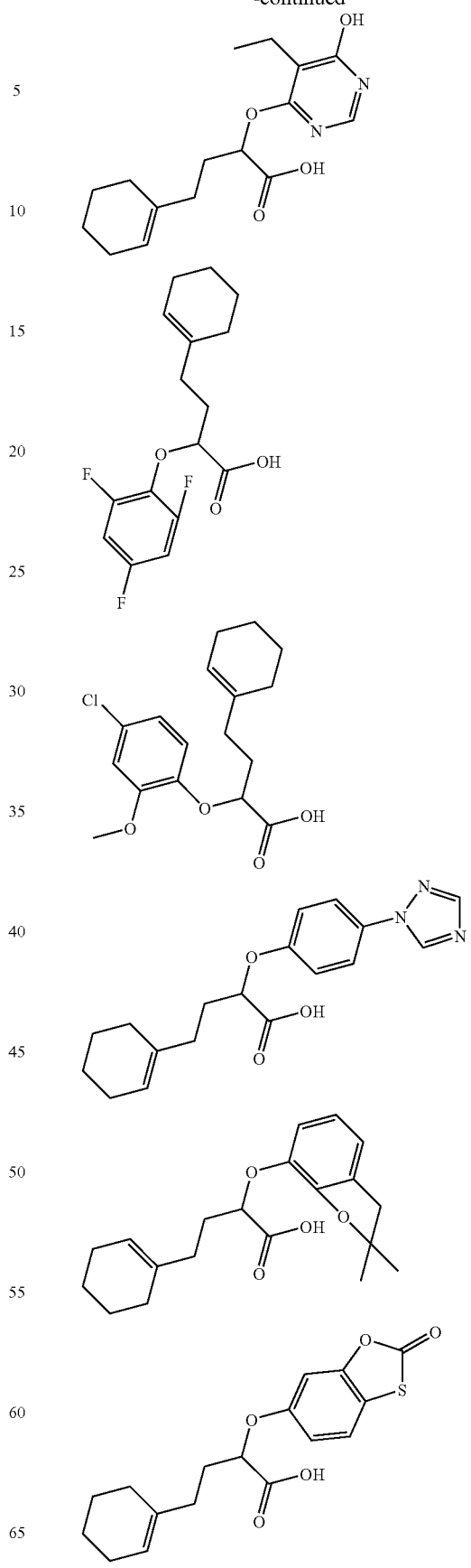

153
-continued
154
-continued
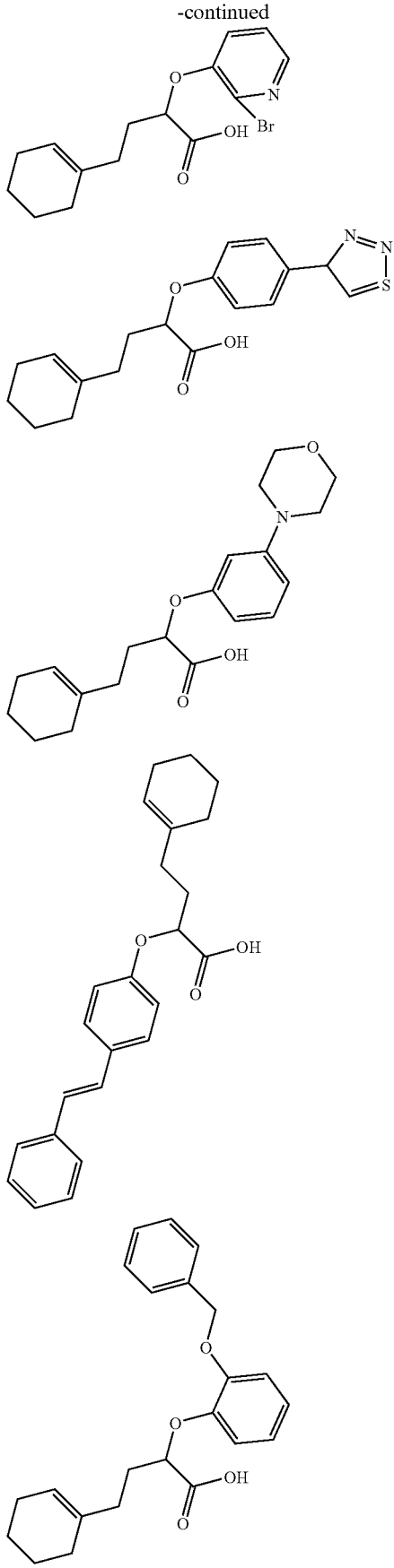
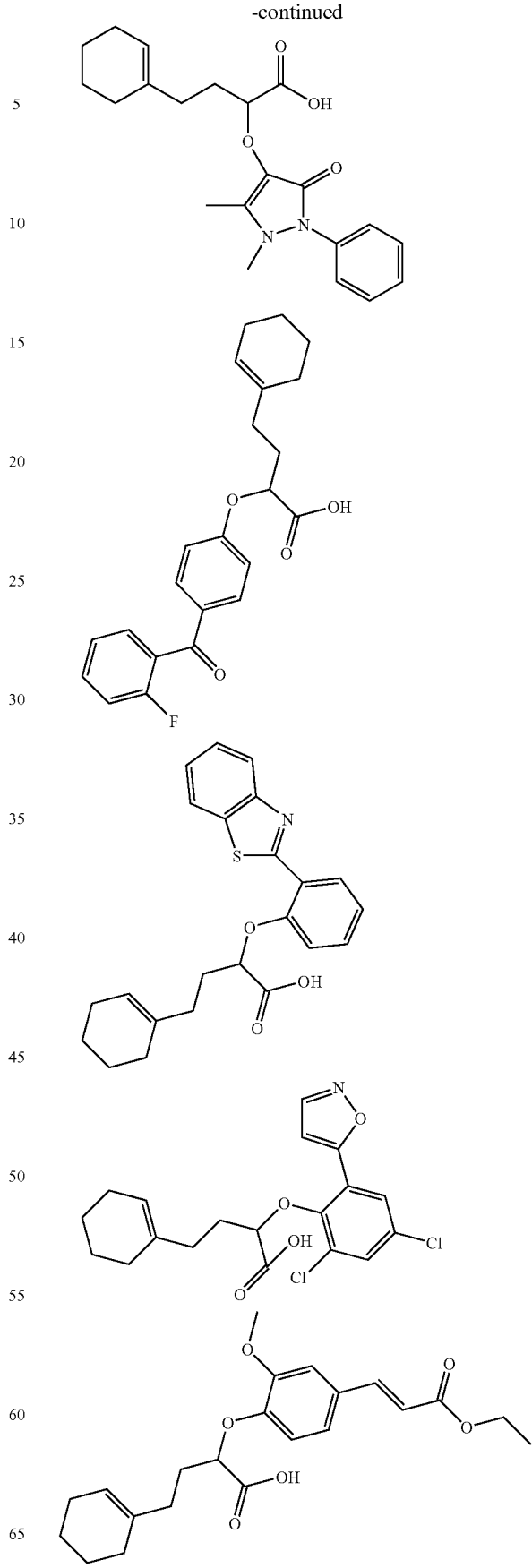

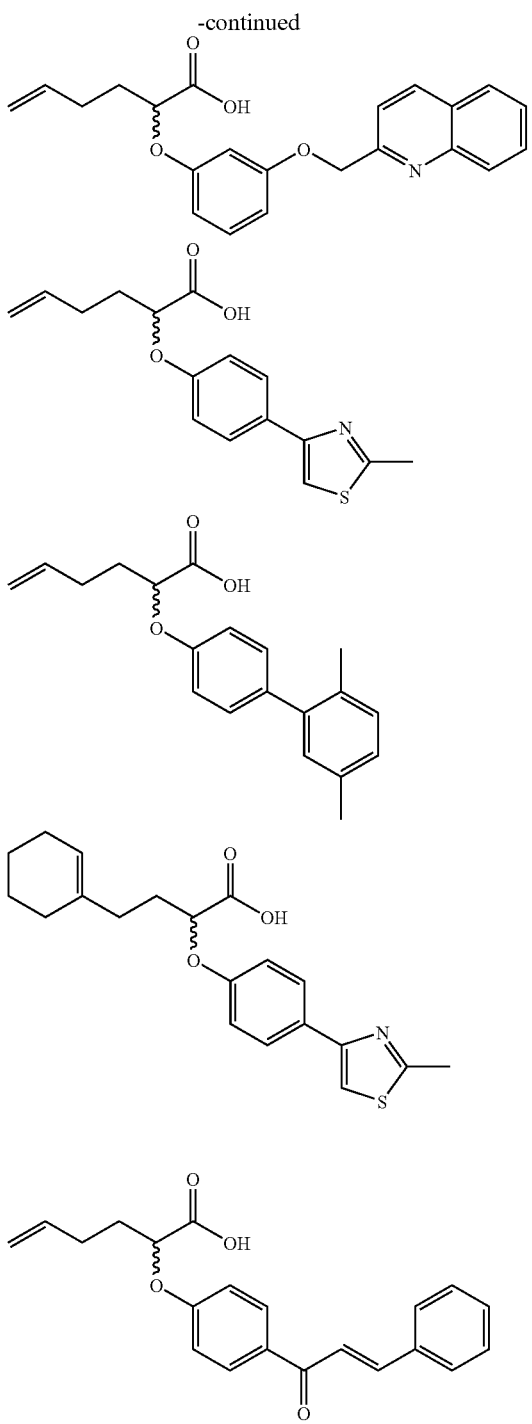
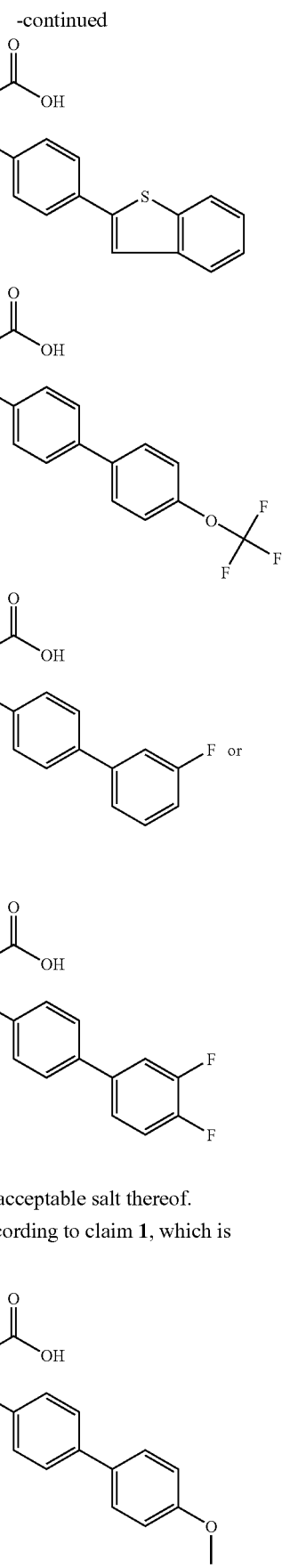
or a pharmaceutically acceptable salt thereof.
13. A compound according to claim 1, which is 157
-continued
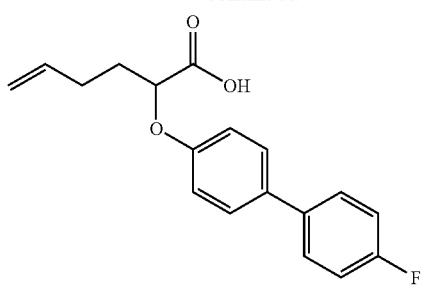
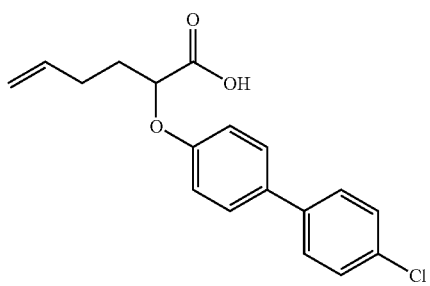
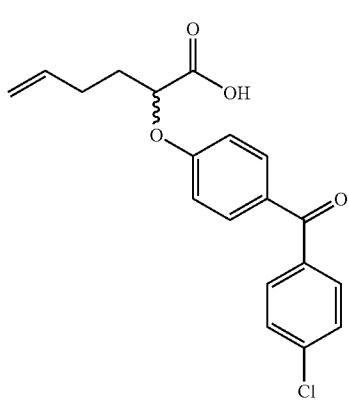
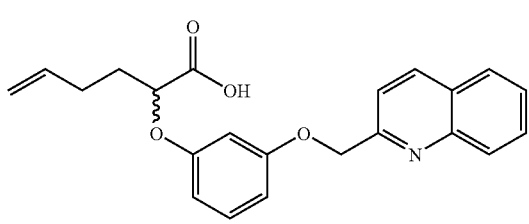
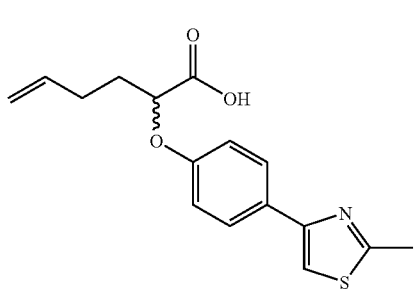
158
-continued
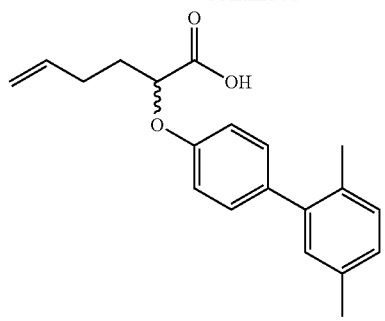
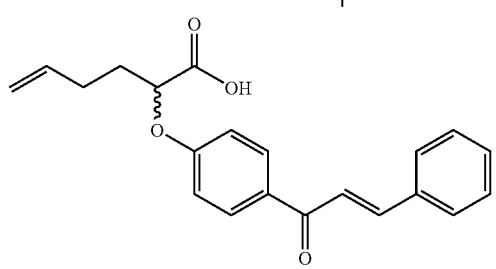
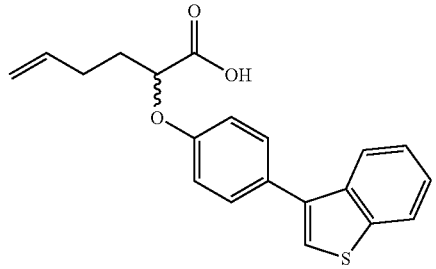
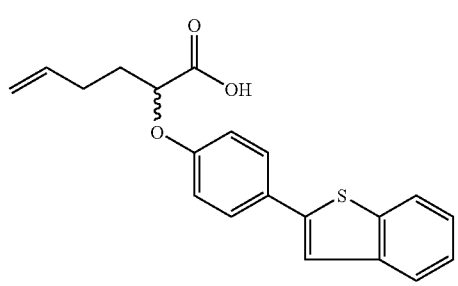
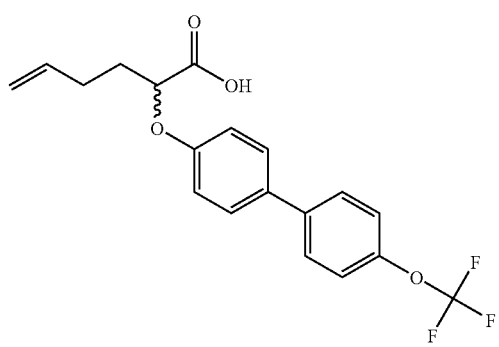

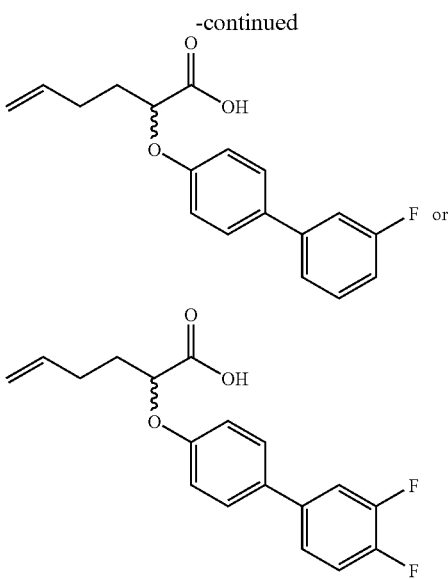

or a pharmaceutically acceptable salt thereof.

14. A pharmaceutical composition comprising a compound according to claim 1 and a pharmaceutically acceptable carrier.

15. A method of treating dyslipidaemia, atherosclerosis or diabetes, comprising administering to a subject in need thereof an effective amount of a pharmaceutical composition that comprises a compound according to claim 1 and a pharmaceutically acceptable carrier.

16. A compound of formula (I):

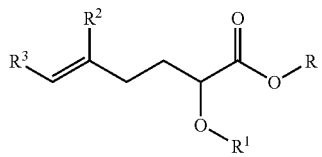

in which:

$R^1$ is a $(C_6\text{-}C_{18})$aryl radical optionally substituted by and/or optionally fused to a saturated or unsaturated monocyclic or polycyclic 5- to 8-membered nucleus optionally containing one or more hetero atoms chosen from O, N and S, said nucleus itself being optionally substituted;

$R^2$ and $R^3$ together form a $C_3\text{-}C_7$ alkylene chain; and

R is hydrogen;

or a pharmaceutically acceptable salt thereof.

17. A pharmaceutical composition comprising a compound according to claim 16 and a pharmaceutically acceptable carrier.

18. A method of treating dyslipidaemia, atherosclerosis or diabetes, comprising administering to a subject in need thereof an effective amount of a pharmaceutical composition that comprises a compound according to claim 16 and a pharmaceutically acceptable carrier.

* * * * *

UNITED STATES PATENT AND TRADEMARK OFFICE
CERTIFICATE OF CORRECTION

PATENT NO.        : 8,063,067 B2
APPLICATION NO.   : 12/507880
DATED             : November 22, 2011
INVENTOR(S)       : Zeiller et al.

It is certified that error appears in the above-identified patent and that said Letters Patent is hereby corrected as shown below:

Column 89, Line 55, delete:

" 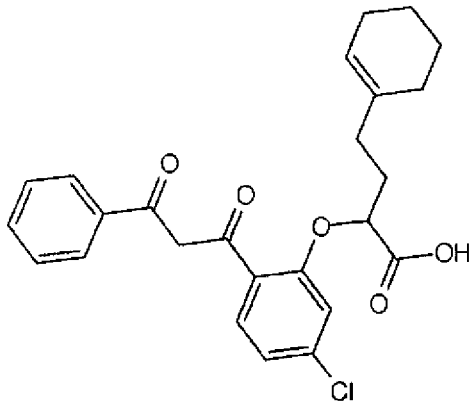 ".

Column 90, Line 1, delete:

" 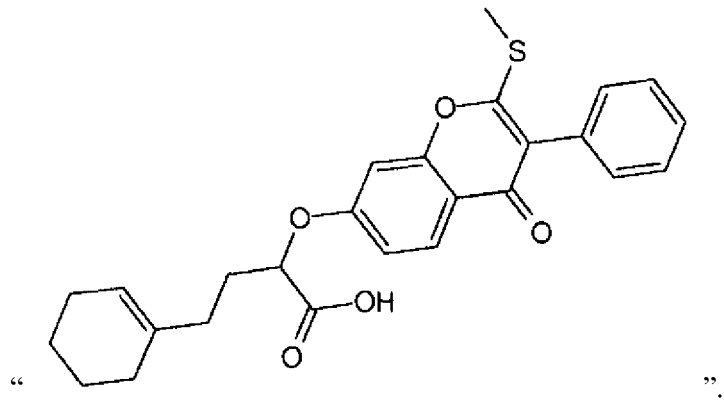 ".

Signed and Sealed this
Twenty-ninth Day of May, 2012

David J. Kappos
*Director of the United States Patent and Trademark Office*

CERTIFICATE OF CORRECTION (continued)
U.S. Pat. No. 8,063,067 B2

Column 90, Line 20, delete:

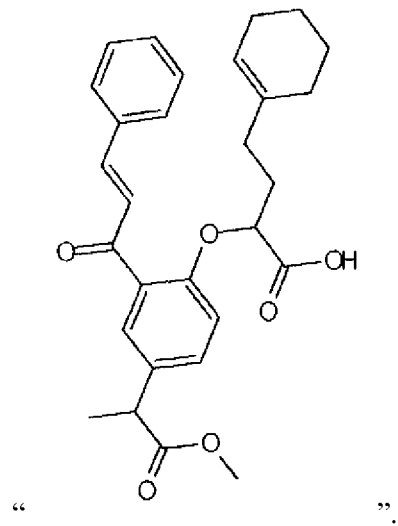

"                    ".